US007060484B1

(12) United States Patent
Gibbs et al.

(10) Patent No.: US 7,060,484 B1
(45) Date of Patent: Jun. 13, 2006

(54) POLYPEPTIDES AND COAGULATION THERAPY

(75) Inventors: Craig S. Gibbs, San Francisco, CA (US); Lawrence L. K. Leung, Hillsborough, CA (US); Manuel Tsiang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/504,735

(22) Filed: Feb. 16, 2000

Related U.S. Application Data

(60) Division of application No. 08/338,368, filed on Nov. 14, 1994, now Pat. No. 6,110,721, which is a continuation-in-part of application No. 08/258,038, filed on Jun. 10, 1994, now abandoned, which is a continuation-in-part of application No. 08/152,657, filed on Nov. 12, 1993, now abandoned.

(51) Int. Cl.
 *C12N 9/74* (2006.01)
(52) U.S. Cl. ............... 435/214; 435/183; 536/23.1; 536/23.2
(58) Field of Classification Search ............. 435/183, 435/214; 536/23.1, 23.2
See application file for complete search history.

(56) References Cited

U.S. PATENT DOCUMENTS

| 4,303,592 A | 12/1981 | Laura et al. |
| 4,775,624 A | 10/1988 | Bang et al. ............. 435/226 |
| 4,849,403 A | 7/1989 | Stocker et al. ............. 514/2 |
| 4,959,314 A | 9/1990 | Mark et al. ............. 435/69 |
| 5,093,117 A | 3/1992 | Lawrence et al. |
| 5,116,943 A | 5/1992 | Koths et al. ............. 530/351 |
| 5,147,638 A | 9/1992 | Esmon et al. |
| 5,223,408 A | 6/1993 | Goeddel et al. ............. 435/69 |
| 5,304,482 A | 4/1994 | Sambrook et al. |
| 5,338,546 A | 8/1994 | Bennett et al. ............. 424/94 |
| 5,352,664 A | 10/1994 | Carney et al. ............. 514/13 |

FOREIGN PATENT DOCUMENTS

| EP | 0 512 011 B1 | 4/1994 |
| WO | WO 93/09807 | 5/1993 |
| WO | WO 93/15755 | 8/1993 |
| WO | WO 93/24635 | 12/1993 |

OTHER PUBLICATIONS

Alberts et al., "Most Mutations in Proteins Are Deleterious and Are Eliminated by Natural Selection", pp. 215, Molecular Biology of the Cell, 1983.
Banfield et al, "Partial characterization of vertebrate prothrombin cDNAs: Amplification and sequence analysis of the B chain of thrombin from nine different species", 89:2779-2783, Proc Natl Acad Sci, 1992.
Bar-Shavit et al, "An Arg-Gly-Asp Sequence Within Thrombin Promotes Endothelial Cell Adhesion", 112(2):335-344, J Cell Biol, 1991.
Bar-Shavit et al, "Localization of a Chemotactic Domain in Human Thrombin", 23(3).397-399, BIOCHEM, 1984.
Bar-Shavit et al, "Identification of a thrombin sequence with growth factor activity on macrophages", 83:976-980, Proc Natl Acad Sci, 1986.
Barnhart, Marion I., "Immunochemistry", , Blood Clotting Enzymology (W. H. Segers, Ed ), 1967
Baum, R., "Mutated Proteins Unlocking Secrets of How Native Proteins Function", 69:23-30, C&E News, 1991.
Baum, R. M., "Enzyme Chemistry Set To Advance As New Techniques Are Applied", pp. 7-14, C&E News, Jul. 14, 1986.
Bode et al, "The refined 1 9 Angstrom crystal structure of human alpha-thrombin: interaction with D-Phe-Pro-Arg chloromethylketone and significance of the Tyr-Pro-Pro-Trp insertion segment", 8(11):3467-3475, EMBO J, 1989.
Borowski et al, "Metal and Phospholipid Binding Properties of Partially Carboxylated Human Prothrombin Variants", 260(16):9258-9264, J Biol Chem, 1985.
Borowski et al, "Distribution of Gamma-Carboxyglutamic Acid Residues in Partially Carboxylated Human Prothrombins", 261(4) 1624-1628, J Biol Chem, 1986.
Bowie et al, "Deciphering the Message in Protein Sequences. Tolerance to Amino Acid Substitutions", 247 1306-1310, SCIENCE, 1990.
Carter et al, "Engineering Enzyme Specificity by Substrate-Assisted Catalysis", 237:394-399, SCIENCE, 1987.
Chang, Jui-Yoa, "Deciphering the structural elements of hirudin C-terminal peptide that bind to the fibrinogen recognition site of alpha-thrombin", 30 6656-6661, BIOCHEM, 1991.

(Continued)

*Primary Examiner*—Ponnathapu Achutamurthy
*Assistant Examiner*—Christian L. Fronda
(74) *Attorney, Agent, or Firm*—Mark L. Bosse

(57) ABSTRACT

Novel polypeptides (NPs) are provided which are capable of protein C activation without significant fibrinogen clotting activity, and vice versa. NPs having enhanced protein C activating properties in relation to fibrinogen clotting are useful in particular as anticoagulants and in screening for substances that agonize or antagonize this property and in diagnostic procedures to determine the status of patients' activated protein C-mediated anticoagulant pathway. Procoagulant NPs are useful to promote clotting in the course of therapy of solid tumors, as an impregnate for bandages, or in diagnostic assays. The NPs are produced in recombinant cell culture or by in vitro methods.

53 Claims, 10 Drawing Sheets

OTHER PUBLICATIONS

Comp et al., "Activation of Protein C in Vivo", 70.127-134, J Clin Invest, 1982.

Craik et al, "Redesigning Trypsin: Alteration of Substrate Specificity", 228 291-297, SCIENCE, 1985.

Dang et al , "Rational engineering of activity and specificity in a serine protease", 15(2):146-149, Nature Biotechnology, 1997.

Degen et al, "Characterization of the Complementary Deoxyribonucleic Acid and Gene Coding for Human Prothrombin", 22 2087-2097, BIOCHEM, 1983.

Ehrlich et al, "Recombinant Human Protein C Derivatives: Altered Response to Calcium Resulting in Enhanced Activation by Thrombin", 9(8):2367-2373, EMBO J, 1990.

Esmon et al., "Inflammation and Coagulation. Linked Processes Potentially Regulated Through A Common Pathway Mediated by Protein C", 66(1):160-165, Thromb Haemo, 1991.

Estell et al, "Probing Steric and Hydrophobic Effects on Enzyme-Substrate Interactions by Protein Engineering", 233:659-663, SCIENCE, 1986.

Estell et al, "Engineering an Enzyme by Site-directed Mutagenesis to Be Resistant to Chemical Oxidation", 260(11):6518-6521, J Biol Chem, 1985.

Fenton II, et al, "Regulation of Thrombin Generation and Functions", 14(3):234-240, Seminars in Thrombosis and Hemostasis, 1988.

Furie et al, "Computer-generated Models of Blood Coagulation Factor Xa, Factor IXa, and Thrombin Based upon Structural Homology with Other Serine Proteases", 257(7):3875-3882, J Biol Chem, 1982.

Gan et al, "Characterization of the Heparin Binding Exosite of Thrombin", 69:1044, Thromb Haemo, 1993.

Gibbs et al, "Conversion of Thrombin into an Anticoagulant by Protein Engineering", 378:413-416, NATURE, 1995.

Gibbs et al, "Functional Mapping of the Surface Residues of Human Thrombin", 82(10):206A, BLOOD, 1993.

Gomi et al, "Antithrombotic Effect of Recombinant Human Thrombomodulin on Thrombin-Induced Thromboembolism in Mice", 75(7):1396-1398, BLOOD, 1990.

Grutter et al, "Crystal structure of the thrombin—hirudin complex: a novel mode of serine protease inhibition", 9(8):2361-2365, EMBO J, 1990.

Hanson et al, "Antithrombotic Effects of Thrombin-induced Activation of Endogenous Protein C in Primates", 92:2003-2012, J Clin Invest, 1993.

Hedner et al, "Chapter 84: Introduction to Hemostasis and the Vitamin K-Dependent Coagulation Factors", pp. 2107-2373, The Metabolic Basis of Inherited Disease II (6th Ed ), 1989.

Hedstrom et al, "Converting Trypsin to Chymotrypsin: The Role of Surface Loops", 255:1249-1253, SCIENCE, 1992.

Henriksen et al, "Identification of the Primary Structural Defect in the Dysthrombin Thrombin Quick I: Substitution of Cysteine for Arginine-382", 27 9160-9165, BIOCHEM, 1988.

Henriksen et al, "Substitution of Valine for Glycine-558 in the Congenital Dysthrombin Thrombin Quick II Alters Primary Substrate Specificity", 28:2078-2082, BIOCHEM, 1989.

Hofsteenge et al, "Enzymatic Properties of Proteolytic Derivatives of Human Alpha-Thrombin", 27:2144-2151, BIOCHEM, 1988.

Horrevoets et al, "Thrombin-Vanable Region 1 (VR1)", 268(2):779-782, J Biol Chem, 1993.

Hung et al, "Mirror Image Antagonists of Thrombin-induced Platelet Activation Based on Thrombin Receptor Structure", 89 444-450, J Clin Invest, 1992.

Hyde et al., "Isolation and Characterization of an in vivo Thrombin-Induced Anticoagulant Activity", 13 121-128, Scand. J. Haemat , 1974.

Jorgensen et al, "Expression of Completely Gamma-Carboxylated Recombinant Human Prothrombin", 262(14):6729-6734, J Biol Chem, 1987.

Kogan et al, "Protein C Activator from the Venom of Agkistrodon blomhoffi ussuriensis Retards Thrombus Formation in the Arterio-Venous Shunt in Rats", 70(5):385-393, Thrombosis Research, 1993.

Le Bonniec et al, "Thrombin Glu-39 Restricts the P'3 Specificity to Nonacidic Residues", 266(21):13796-13803, J Biol Chem, 1991.

Le Bonniec et al, "The Role of Thrombins's Tyr-Pro-Pro-Trp motif in the Interaction with Fibrinogen, Thrombomodulin, Protein C. Antithrombin III, and the Kunitz Inhibitors", 268(25):19055-19061, J Biol Chem, 1993.

Le Bonniec et al, "Glu-192→Gln substitution in thrombin mimics the catalytic switch induced by thrombomodulin", 88:7371-7375, Proc Natl Acad Sci, 1991.

Li et al, "Mutagenesis On The Loop Thr147 To Ser158 Of Human Thrombin Does Not Abolish Thrombomodulin Binding Site", 69:1045, Thromb Haemo, 1993.

Lundblad et al., "The reaction of bovine alpha-thrombin with tetranitromethane", 263(8):3729-3734, J Biol Chem, 1988.

MacGillivray et al, "Recombinant Genetic Approaches to Functional Mapping of Thrombin",485 73-79, Ann NY Acad Sci, 1986.

Magnusson et al, "Complete Primary Structure of Prothrombin, Isolation, Structure and Reactivity of Ten Carboxylated Glutamic Acid Residues and Regulation of Prothrombin Activation by Thrombin", 2:123-149, Prot & Biol Control, 1975.

Mann et al, "Biochemistry of Thrombin", 2 ed., Chapter 10, pp. 148-161, Hemo Thromb, 1987.

Mann et al, "The Molecular Weights of Bovine Thrombin and Its Primary Autolysis Products", 244(23):6555-6557, Thromb Pept, 1969.

Martin et al., "The structure of residues 7-16 of the A-alpha-chain of human fibrinogen bound to bovine thrombin at 2.3-angstroms resolution", 267(11):7911-7920, J Biol Chem, 1992.

Meier, J. et al, "Snake Venom Protein C Activators", 5:265-279, Handbook of Natural Toxins, 1991.

Miyata et al, "Prothrombin Tokushima, a Replacement of Arginine-418 by Tryptophan That Impairs the Fibrinogen Clotting Activity of Derived Thrombin Tokushima", 26:1117-1122, BIOCHEM, 1987.

Miyata et al., "Prothrombin Salakta: substitution of glutamic acid-466 by alanine reduces the fibrinogen clotting activity and the esterase activity", 31:7457-7462, BIOCHEM, 1992.

Nakagaki et al, "Isolation and Characterization of a Protein C Activator from Tropical Moccasin Venom", 58:593-602, Thrombosis Research, 1990.

Naray-Szabo et al, "Rational Design In Genetic Engineering: Dream or Reality? A Priori Predictions For Thrombin And Ribonuclease A Mutants", 200:401-412, J Mol Struct, 1989.

Neurath, Hans, "Evolution of Proteolytic Enzymes", 224 350-357, SCIENCE, 1984.

Ni et al., "High Resolution NMR Studies of Fibrinogen-like Peptides in Solution. Structural Basis for the Bleeding Disorder Caused by a Single Mutation of Gly(12) to Val(12) in the A alpha Chain of Human Fibrinogen Rouen", 28:3106-3119, Biochemistry (2nd Ed.), 1989.

Noe et al, "The Use of Sequence-specific Antibodies to Identify a Secondary Binding Site in Thrombin", 263(24):11729-11735, J Biol Chem, 1988.

Paborsky et al., "The Single-Stranded DNA Aptamer-binding Site of Human Thrombin", 268(28):20808-20811, J Biol Chem, 1993.

Padmanabhan et al, "The Structure of alpha-Thrombin Inhibited by a 15-Mer Single-stranded DNA Aptamer", 268(24):17651-16754, J Biol Chem, 1993.

Rabiet et al, "Molecular Defect of Prothrombin Barcelona", 261(32).15045-15048, J Biol Chem, 1986.

Richardson et al, "Enhancing protein C interaction with thrombin results in a clot-activated anticoagulant", 360:261-264, NATURE, 1992.

Rosenberg et al, "Multiple Bovine Thrombin Components", 245(19):5049-5056, J Biol Chem, 1970.

Rydel et al, "The Structure of a Complex of Recombinant Hirudin and Human Alpha-Thrombin", 249:277-280, SCIENCE, 1990.

Seegers et al, "Preparation and Properties of Thrombin", 128 194-201, Arch Biochem & Biophys, 1968.

Sheehan et al, "Mutagenesis of Thrombin Selectively Modulates Inhibition by Serpins Heparin Cofactor II and Antithrombin III", 268(5):3639-3645, J Biol Chem, 1993.

Sheehan et al, "Identification of the Heparin-Binding Exosite of Thrombin By Site-Directed Mutagenesis", 69:1044, Thromb Haemo, 1993.

Sheehan et al, "Molecular Mapping of the Heparin Binding Exosite of Thrombin", 82.206a, Abstract No. 809, BLOOD, 1993.

Sheehan et al, "Molecular mapping of the heparin-binding exosite of thrombin", 91:5518-5522, Proc Natl Acad Sci, 1994.

Stocker et al, "Practical Application of the Protein C Activator Protac from Agkistrodon Contrortix Venom", 115(3,S) 260-264, Folia Haematol., Leipzig, 1988.

Stocker et al, "Protein C Activators in Snake Venoms", 79 37-47, Behring Inst. Mitt., 1986.

Strukova et al, "Anticoagulant Effect of the Protease from Agkistrodon Venom Mediated by Protein C Activation in Rats", 55(1) 149-153, Thrombosis Research, 1989.

Stryer et al., "Biochemistry", 3rd ed ,pp. 136-138, , 1988.

Suzuki et al, "Localization of Thrombomodulin-binding Site within Human Thrombin", 265(22):13263-13267, J Biol Chem, 1990.

Suzuki et al, "A Thrombin-based peptide Corresponding to the Sequence of the Thrombomodulin-binding Site Blocks the Procoagulant Activities of Thrombin", 266(28):18498-18501, J Biol Chem, 1991.

Tsiang et al, "Equilibrium Binding of Thrombin to Recombinant Human Thrombomodulin. Effect of Hirudin, Fibrinogen, Factor Va, and Peptide Analogues", 29 10602-10612, BIOCHEM, 1990.

Tsiang et al., "Functional Mapping of the Surface Residues of Human Thrombin", 270(28):16854-16863, J Biol Chem, 1995.

Valenzuela et al, "Is sequence conservation in interferons due to selection for functional proteins?", 313(21):698-700, NATURE, 1985.

Wells et al, "Designing substrate specificity by protein engineering of electrostatic interactions", 84 1219-1223, Proc Natl Acad Sci, 1987.

Wells et al, "Recruitment of substrate-specificity properties from one enzyme into a related one by protein engineering", 84 5167-5171, Proc Natl Acad Sci, 1987.

Wells et al., "In Vivo Formation and Stabiity of Engineered Disulfide Bonds in Subtilisin", 261(14):6564-6570, J Biol Chem, 1986.

White et al, "Structure-Function Relations in Platelet-Thrombin Reactions", 256(4).1763-1766, J Biol Chem, 1981.

Wu et al, "Single amino acid substitutions dissociate fibrinogen-clotting and thrombomodulin-binding activities of human thrombin", 88:6775-6779, Proc Natl Acad Sci, 1991.

Ye et al, "Glycosaminoglycan contributions to both Protein C activation and thrombin inhibition involve a common arginini-rich site in thrombin", 269(8):17965-17970, J Biol Chem, 1994.

FIG. 1A

| | | | | | | | | | | | | |
|---|---|---|---|---|---|---|---|---|---|---|---|---|
| 1a | 2a | 3a | 4a | 5a | 6a | 7a | 8a | 9a | 10a | 11a | 12a | 13a |
| Thr | Phe | Gly | Ser | Gly | Glu | Ala | Asp | Cys | Gly | Leu | Arg | Pro |
| ACC | TTT | GGC | TCG | GGA | GAG | GCA | GAC | TGT | GGG | CTG | CGA | CCT |
| TGG | AAA | CCG | AGC | CCT | CTC | CGT | CTG | ACA | CCC | GAC | GCT | GGA |

| | | | | | | | | | | | | |
|---|---|---|---|---|---|---|---|---|---|---|---|---|
| 14a | 15a | 16a | 17a | 18a | 19a | 20a | 21a | 22a | 23a | 24a | 25a | 26a |
| Leu | Phe | Glu | Lys | Lys | Ser | Leu | Glu | Asp | Lys | Thr | Glu | Arg |
| CTG | TTC | GAG | AAG | AAG | TCG | CTG | GAG | GAC | AAA | ACC | GAA | AGA |
| GAC | AAG | CTC | TTC | TTC | AGC | GAC | CTC | CTG | TTT | TGG | CTT | TCT |

| | | | | | | | | | | | | |
|---|---|---|---|---|---|---|---|---|---|---|---|---|
| 27a | 28a | 29a | 30a | 31a | 32a | 33a | 34a | 35a | 36a | 1 | 2 | 3 |
| Glu | Leu | Leu | Glu | Ser | Tyr | Ile | Asp | Gly | Arg | Ile | Val | Glu |
| GAG | CTC | CTG | GAA | TCC | TAC | ATC | GAC | GGG | CGC | ATT | GTG | GAG |
| CTC | GAG | GAC | CTT | AGG | ATG | TAG | CTG | CCC | GCG | TAA | CAC | CTC |

| | | | | | | | | | | | | |
|---|---|---|---|---|---|---|---|---|---|---|---|---|
| 4 | 5 | 6 | 7 | 8 | 9 | 10 | 11 | 12 | 13 | 14 | 15 | 16 |
| Gly | Ser | Asp | Ala | Glu | Ile | Gly | Met | Ser | Pro | Trp | Gln | Val |
| GGC | TCG | GAT | GCA | GAG | ATC | GGC | ATG | TCA | CCT | TGG | CAG | GTG |
| CCG | AGC | CTA | CGT | CTC | TAG | CCG | TAC | AGT | GGA | ACC | GTC | CAC |

| | | | | | | | | | | | | |
|---|---|---|---|---|---|---|---|---|---|---|---|---|
| 17 | 18 | 19 | 20 | 21 | 22 | 23 | 24 | 25 | 26 | 27 | 28 | 29 |
| Met | Leu | Phe | Arg | Lys | Ser | Pro | Gln | Gln | Leu | Leu | Cys | Gly |
| ATG | CTT | TTC | CGG | AAG | AGT | CCC | CAG | GAG | CTG | CTG | TGT | GGG |
| TAC | GAA | AAG | GCC | TTC | TCA | GGG | GTC | CTC | GAC | GAC | ACA | CCC |

| | | | | | | | | | | | | |
|---|---|---|---|---|---|---|---|---|---|---|---|---|
| 30 | 31 | 32 | 33 | 34 | 35 | 36 | 37 | 38 | 39 | 40 | 41 | 42 |
| Ala | Ser | Leu | Ile | Ser | Asp | Arg | Trp | Val | Leu | Thr | Ala | Ala |
| GCC | AGC | CTC | ATC | AGT | GAC | CGC | TGG | GTC | CTC | ACC | GCC | GCC |
| CGG | TCG | GAG | TAG | TCA | CTG | GCG | ACC | CAG | GAG | TGG | CGG | CGG |

| | | | | | | | | | | | | |
|---|---|---|---|---|---|---|---|---|---|---|---|---|
| 43 | 44 | 45 | 46 | 47 | 48 | 49 | 50 | 51 | 52 | 53 | 54 | 55 |
| His | Cys | Leu | Leu | Tyr | Pro | Pro | Trp | Asp | Lys | Asn | Phe | Thr |
| CAC | TGC | CTC | CTG | TAC | CCG | CCC | TGG | GAC | AAG | AAC | TTC | ACC |
| GTG | ACG | GAG | GAC | ATG | GGC | GGG | ACC | CTG | TTC | TTG | AAG | TGG |

| | | | | | | | | | | | | |
|---|---|---|---|---|---|---|---|---|---|---|---|---|
| 56 | 57 | 58 | 59 | 60 | 61 | 62 | 63 | 64 | 65 | 66 | 67 | 68 |
| Glu | Asn | Asp | Leu | Leu | Val | Arg | Ile | Gly | Lys | His | Ser | Arg |
| GAG | AAT | GAC | CTT | CTG | GTG | CGC | ATT | GGC | AAG | CAC | TCC | CGC |
| CTC | TTA | CTG | GAA | GAC | CAC | GCG | TAA | CCG | TTC | GTG | AGG | GCG |

FIG. 1B

| 69 | 70 | 71 | 72 | 73 | 74 | 75 | 76 | 77 | 78 | 79 | 80 | 81 |
|---|---|---|---|---|---|---|---|---|---|---|---|---|
| Thr | Arg | Tyr | Glu | Arg | Asn | Ile | Glu | Lys | Ile | Ser | Met | Leu |
| ACC | AGG | TAC | GAG | CGA | AAC | ATT | GAA | AAG | ATA | TCC | ATG | TTG |
| TGG | TCC | ATG | CTC | GCT | TTG | TAA | CTT | TTC | TAT | AGG | TAC | AAC |

| 82 | 83 | 84 | 85 | 86 | 87 | 88 | 89 | 90 | 91 | 92 | 93 | 94 |
|---|---|---|---|---|---|---|---|---|---|---|---|---|
| Glu | Lys | Ile | Tyr | Ile | His | Pro | Arg | Tyr | Asn | Trp | Arg | Glu |
| GAA | AAG | ATC | TAC | ATC | CAC | CCC | AGG | TAC | AAC | TGG | CGG | GAG |
| CTT | TTC | TAG | ATG | TAG | GTG | GGG | TCC | ATG | TTG | ACC | GCC | CTC |

| 95 | 96 | 97 | 98 | 99 | 100 | 101 | 102 | 103 | 104 | 105 | 106 | 107 |
|---|---|---|---|---|---|---|---|---|---|---|---|---|
| Asn | Leu | Asp | Arg | Asp | Ile | Ala | Leu | Met | Lys | Leu | Lys | Lys |
| AAC | CTG | GAC | CGG | GAC | ATT | GCC | CTG | ATG | AAG | CTG | AAG | AAG |
| TTG | GAC | CTG | GCC | CTG | TAA | CGG | GAC | TAC | TTC | GAC | TTC | TTC |

| 108 | 109 | 110 | 111 | 112 | 113 | 114 | 115 | 116 | 117 | 118 | 119 | 120 |
|---|---|---|---|---|---|---|---|---|---|---|---|---|
| Pro | Val | Ala | Phe | Ser | Asp | Tyr | Ile | His | Pro | Val | Cys | Leu |
| CCT | GTT | GCC | TTC | AGT | GAC | TAC | ATT | CAC | CCT | GTG | TGT | CTG |
| GGA | CAA | CGG | AAG | TCA | CTG | ATG | TAA | GTG | GGA | CAC | ACA | GAC |

| 121 | 122 | 123 | 124 | 125 | 126 | 127 | 128 | 129 | 130 | 131 | 132 | 133 |
|---|---|---|---|---|---|---|---|---|---|---|---|---|
| Pro | Asp | Arg | Glu | Thr | Ala | Ala | Ser | Leu | Leu | Gln | Ala | Gly |
| CCC | GAC | AGG | GAG | ACG | GCA | GCC | AGC | TTG | CTC | CAG | GCT | GGA |
| GGG | CTG | TCC | CTC | TGC | CGT | CGG | TCG | AAC | GAG | GTC | CGA | CCT |

| 134 | 135 | 136 | 137 | 138 | 139 | 140 | 141 | 142 | 143 | 144 | 145 | 146 |
|---|---|---|---|---|---|---|---|---|---|---|---|---|
| Tyr | Lys | Gly | Arg | Val | Thr | Gly | Trp | Gly | Asn | Leu | Lys | Glu |
| TAC | AAG | GGG | CGG | GTG | ACA | GGC | TGG | GGC | AAC | CTG | AAG | GAG |
| ATG | TTC | CCC | GCC | CAC | TGT | CCG | ACC | CCG | TTG | GAC | TTC | CTC |

| 147 | 148 | 149 | 150 | 151 | 152 | 153 | 154 | 155 | 156 | 157 | 158 | 159 |
|---|---|---|---|---|---|---|---|---|---|---|---|---|
| Thr | Trp | Thr | Ala | Asn | Val | Gly | Lys | Gly | Gln | Pro | Ser | Val |
| ACG | TGG | ACA | GCC | AAC | GTT | GGT | AAG | GGG | CAG | CCC | AGT | GTC |
| TGC | ACC | TGT | CGG | TTG | CAA | CCA | TTC | CCC | GTC | GGG | TCA | CAG |

| 160 | 161 | 162 | 163 | 164 | 165 | 166 | 167 | 168 | 169 | 170 | 171 | 172 |
|---|---|---|---|---|---|---|---|---|---|---|---|---|
| Leu | Gln | Val | Val | Asn | Leu | Pro | Ile | Val | Glu | Arg | Pro | Val |
| CTG | CAG | GTG | GTG | AAC | CTG | CCC | ATT | GTG | GAG | CGG | CCG | GTC |
| GAC | GTC | CAC | CAC | TTG | GAC | GGG | TAA | CAC | CTC | GCC | GGC | CAG |

FIG. 1C

| 173 | 174 | 175 | 176 | 177 | 178 | 179 | 180 | 181 | 182 | 183 | 184 | 185 |
|---|---|---|---|---|---|---|---|---|---|---|---|---|
| Cys | Lys | Asp | Ser | Thr | Arg | Ile | Arg | Ile | Thr | Asp | Asn | Met |
| TGC | AAG | GAC | TCC | ACC | CGG | ATC | CGC | ATC | ACT | GAC | AAC | ATG |
| ACG | TTC | CTG | AGG | TGG | GCC | TAG | GCG | TAG | TGA | CTG | TTG | TAC |

| 186 | 187 | 188 | 189 | 190 | 191 | 192 | 193 | 194 | 195 | 196 | 197 | 198 |
|---|---|---|---|---|---|---|---|---|---|---|---|---|
| Phe | Cys | Ala | Gly | Tyr | Lys | Pro | Asp | Glu | Gly | Lys | Arg | Gly |
| TTC | TGT | GCT | GGT | TAC | AAG | CCT | GAT | GAA | GGG | AAA | CGA | GGG |
| AAG | ACA | CGA | CCA | ATG | TTC | GGA | CTA | CTT | CCC | TTT | GCT | CCC |

| 199 | 200 | 201 | 202 | 203 | 204 | 205 | 206 | 207 | 208 | 209 | 210 | 211 |
|---|---|---|---|---|---|---|---|---|---|---|---|---|
| Asp | Ala | Cys | Glu | Gly | Asp | Ser | Gly | Gly | Pro | Phe | Val | Met |
| GAT | GCC | TGT | GAA | GGT | GAC | AGT | GGG | GGA | CCC | TTT | GTC | ATG |
| CTA | CGG | ACA | CTT | CCA | CTG | TCA | CCC | CCT | GGG | AAA | CAG | TAC |

| 212 | 213 | 214 | 215 | 216 | 217 | 218 | 219 | 220 | 221 | 222 | 223 | 224 |
|---|---|---|---|---|---|---|---|---|---|---|---|---|
| Lys | Ser | Pro | Phe | Asn | Asn | Arg | Trp | Tyr | Gln | Met | Gly | Ile |
| AAG | AGC | CCC | TTT | AAC | AAC | CGC | TGG | TAT | CAA | ATG | GGC | ATC |
| TTC | TCG | GGG | AAA | TTG | TTG | GCG | ACC | ATA | GTT | TAC | CCG | TAG |

| 225 | 226 | 227 | 228 | 229 | 230 | 231 | 232 | 233 | 234 | 235 | 236 | 237 |
|---|---|---|---|---|---|---|---|---|---|---|---|---|
| Val | Ser | Trp | Gly | Glu | Gly | Cys | Asp | Arg | Asp | Gly | Lys | Tyr |
| GTC | TCA | TGG | GGT | GAA | GGC | TGT | GAC | CGG | GAT | GGG | AAA | TAT |
| CAG | AGT | ACC | CCA | CTT | CCG | ACA | CTG | GCC | CTA | CCC | TTT | ATA |

| 238 | 239 | 240 | 241 | 242 | 243 | 244 | 245 | 246 | 247 | 248 | 249 | 250 |
|---|---|---|---|---|---|---|---|---|---|---|---|---|
| Gly | Phe | Tyr | Thr | His | Val | Phe | Arg | Leu | Lys | Lys | Trp | Ile |
| GGC | TTC | TAC | ACA | CAT | GTG | TTC | CGC | CTG | AAG | AAG | TGG | ATA |
| CCG | AAG | ATG | TGT | GTA | CAC | AAG | GCG | GAC | TTC | TTC | ACC | TAT |

| 251 | 252 | 253 | 254 | 255 | 256 | 257 | 258 | 259 |
|---|---|---|---|---|---|---|---|---|
| Gln | Lys | Val | Ile | Asp | Gln | Phe | Gly | Glu |
| CAG | AAG | GTC | ATT | GAT | CAG | TTT | GGA | GAG |
| GTC | TTC | CAG | TAA | CTA | GTC | AAA | CCT | CTC |

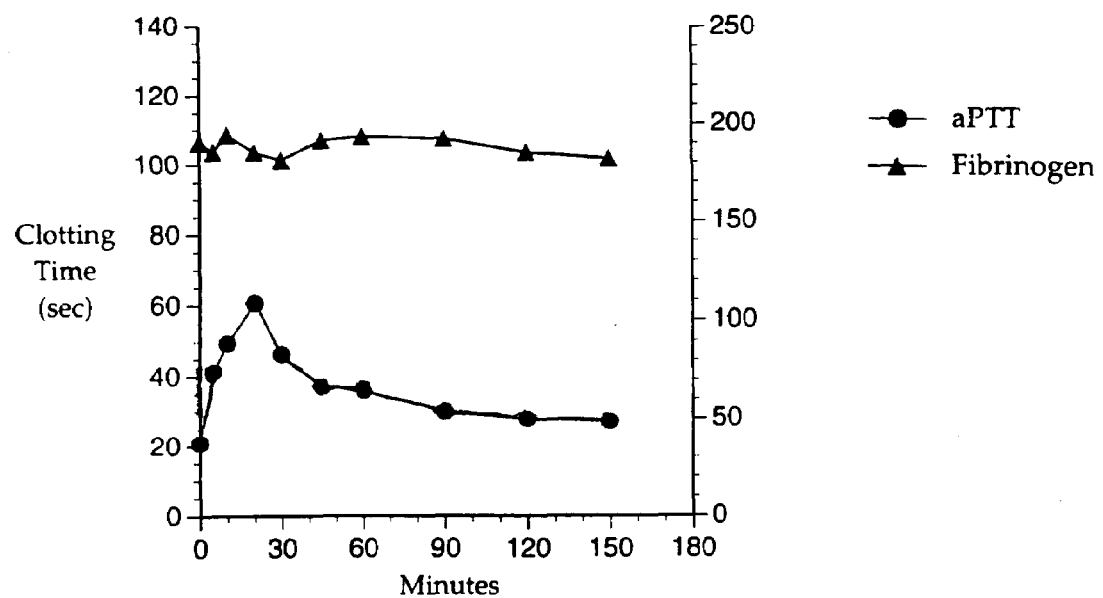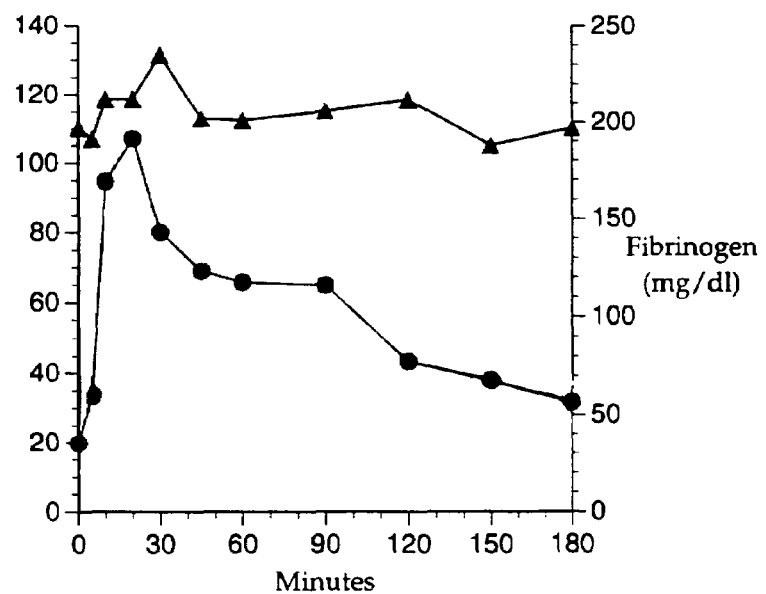
Figure 4

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 885 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 1..885

(xi) SEQUENCE DESCRIPTION: SEQ ID NO: 1:

```
ACC TTT GGC TCG GGA GAG GCA GAC TGT GGG CTG CGA CCT CTG TTC GAG       48
Thr Phe Gly Ser Gly Glu Ala Asp Cys Gly Leu Arg Pro Leu Phe Glu
 1               5                  10                  15

AAG AAG TCG CTG GAG GAC AAA ACC GAA AGA GAG CTC CTG GAA TCC TAC       96
Lys Lys Ser Leu Glu Asp Lys Thr Glu Arg Glu Leu Leu Glu Ser Tyr
             20                  25                  30

ATC GAC GGG CGC ATT GTG GAG GGC TCG GAT GCA GAG ATC GGC ATG TCA      144
Ile Asp Gly Arg Ile Val Glu Gly Ser Asp Ala Glu Ile Gly Met Ser
         35                  40                  45

CCT TGG CAG GTG ATG CTT TTC CGG AAG AGT CCC CAG GAG CTG CTG TGT      192
Pro Trp Gln Val Met Leu Phe Arg Lys Ser Pro Gln Glu Leu Leu Cys
 50                  55                  60

GGG GCC AGC CTC ATC AGT GAC CGC TGG GTC CTC ACC GCC GCC CAC TGC      240
Gly Ala Ser Leu Ile Ser Asp Arg Trp Val Leu Thr Ala Ala His Cys
 65                  70                  75                  80

CTC CTG TAC CCG CCC TGG GAC AAG AAC TTC ACC GAG AAT GAC CTT CTG      288
Leu Leu Tyr Pro Pro Trp Asp Lys Asn Phe Thr Glu Asn Asp Leu Leu
                 85                  90                  95

GTG CGC ATT GGC AAG CAC TCC CGC ACC AGG TAC GAG CGA AAC ATT GAA      336
Val Arg Ile Gly Lys His Ser Arg Thr Arg Tyr Glu Arg Asn Ile Glu
            100                 105                 110

AAG ATA TCC ATG TTG GAA AAG ATC TAC ATC CAC CCC AGG TAC AAC TGG      384
Lys Ile Ser Met Leu Glu Lys Ile Tyr Ile His Pro Arg Tyr Asn Trp
        115                 120                 125

CGG GAG AAC CTG GAC CGG GAC ATT GCC CTG ATG AAG CTG AAG AAG CCT      432
Arg Glu Asn Leu Asp Arg Asp Ile Ala Leu Met Lys Leu Lys Lys Pro
    130                 135                 140

GTT GCC TTC AGT GAC TAC ATT CAC CCT GTG TGT CTG CCC GAC AGG GAG      480
Val Ala Phe Ser Asp Tyr Ile His Pro Val Cys Leu Pro Asp Arg Glu
145                 150                 155                 160

ACG GCA GCC AGC TTG CTC CAG GCT GGA TAC AAG GGG CGG GTG ACA GGC      528
Thr Ala Ala Ser Leu Leu Gln Ala Gly Tyr Lys Gly Arg Val Thr Gly
                165                 170                 175

TGG GGC AAC CTG AAG GAG ACG TGG ACA GCC AAC GTT GGT AAG GGG CAG      576
Trp Gly Asn Leu Lys Glu Thr Trp Thr Ala Asn Val Gly Lys Gly Gln
            180                 185                 190

CCC AGT GTC CTG CAG GTG GTG AAC CTG CCC ATT GTG GAG CGG CCG GTC      624
Pro Ser Val Leu Gln Val Val Asn Leu Pro Ile Val Glu Arg Pro Val
        195                 200                 205

TGC AAG GAC TCC ACC CGG ATC CGC ATC ACT GAC AAC ATG TTC TGT GCT      672
Cys Lys Asp Ser Thr Arg Ile Arg Ile Thr Asp Asn Met Phe Cys Ala
    210                 215                 220

GGT TAC AAG CCT GAT GAA GGG AAA CGA GGG GAT GCC TGT GAA GGT GAC      720
```

-continued

```
Gly Tyr Lys Pro Asp Glu Gly Lys Arg Gly Asp Ala Cys Glu Gly Asp
225                 230                 235                 240

AGT GGG GGA CCC TTT GTC ATG AAG AGC CCC TTT AAC AAC CGC TGG TAT      768
Ser Gly Gly Pro Phe Val Met Lys Ser Pro Phe Asn Asn Arg Trp Tyr
                    245                 250                 255

CAA ATG GGC ATC GTC TCA TGG GGT GAA GGC TGT GAC CGG GAT GGG AAA      816
Gln Met Gly Ile Val Ser Trp Gly Glu Gly Cys Asp Arg Asp Gly Lys
                260                 265                 270

TAT GGC TTC TAC ACA CAT GTG TTC CGC CTG AAG AAG TGG ATA CAG AAG      864
Tyr Gly Phe Tyr Thr His Val Phe Arg Leu Lys Lys Trp Ile Gln Lys
            275                 280                 285

GTC ATT GAT CAG TTT GGA GAG                                          885
Val Ile Asp Gln Phe Gly Glu
290                 295
```

(2) INFORMATION FOR SEQ ID NO: 2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO: 2:

```
Thr Phe Gly Ser Gly Glu Ala Asp Cys Gly Leu Arg Pro Leu Phe Glu
1               5                   10                  15

Lys Lys Ser Leu Glu Asp Lys Thr Glu Arg Glu Leu Leu Glu Ser Tyr
                20                  25                  30

Ile Asp Gly Arg Ile Val Glu Gly Ser Asp Ala Glu Ile Gly Met Ser
            35                  40                  45

Pro Trp Gln Val Met Leu Phe Arg Lys Ser Pro Gln Glu Leu Leu Cys
        50                  55                  60

Gly Ala Ser Leu Ile Ser Asp Arg Trp Val Leu Thr Ala Ala His Cys
65                  70                  75                  80

Leu Leu Tyr Pro Pro Trp Asp Lys Asn Phe Thr Glu Asn Asp Leu Leu
                85                  90                  95

Val Arg Ile Gly Lys His Ser Arg Thr Arg Tyr Glu Arg Asn Ile Glu
                100                 105                 110

Lys Ile Ser Met Leu Glu Lys Ile Tyr Ile His Pro Arg Tyr Asn Trp
            115                 120                 125

Arg Glu Asn Leu Asp Arg Asp Ile Ala Leu Met Lys Leu Lys Lys Pro
130                 135                 140

Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
                165                 170                 175

Trp Gly Asn Leu Lys Glu Thr Trp Thr Ala Asn Val Gly Lys Gly Gln
            180                 185                 190

Pro Ser Val Leu Gln Val Val Asn Leu Pro Ile Val Glu Arg Pro Val
        195                 200                 205

Cys Lys Asp Ser Thr Arg Ile Arg Ile Thr Asp Asn Met Phe Cys Ala
210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
                245                 250                 255
```

-continued

```
Gln Met Gly Ile Val Ser Trp Gly Glu Gly Cys Asp Arg Asp Gly Lys
            260                 265                 270

Tyr Gly Phe Tyr Thr His Val Phe Arg Leu Lys Lys Trp Ile Gln Lys
        275                 280                 285

Val Ile Asp Gln Phe Gly Glu
    290             295
```

POLYPEPTIDES AND COAGULATION THERAPY

This is a divisional of U.S. Ser. No. 08/338,368, filed Nov. 14, 1994, U.S. Pat. No. 6,110,721, which is a continuation-in-part of U.S. Ser. No. 08/258,038, filed Jun. 10, 1994, abandoned, which in turn is a continuation-in-part of U.S. Ser. No. 08/152,657, filed Nov. 12, 1993, abandoned.

BACKGROUND OF THE INVENTION

Thrombin, a key enzyme in hemostasis, has both procoagulant and anticoagulant properties, based on its different substrate specificities. Thrombin is secreted from the liver as an inactive zymogen, prothrombin, that is activated by coagulation factors Va and Xa to yield mature α-thrombin. This process can be mimicked in vitro by the proteolytic cleavage of prothrombin with various snake venoms such as Echis carinatus venom.

Thrombin acts as a procoagulant by the proteolytic cleavage of fibrinogen, ultimately resulting in the formation of an insoluble fibrin clot, the activation of the clotting cofactors factor V and Factor VIII to FVa and FVIIIa, the cleavage of Factor XI to activated Factor XIa (leading to further activation of Factors IX and X and perpetuation of clotting) and the cleavage of the platelet thrombin receptor, resulting in platelet activation. On the other hand, when thrombin binds to thrombomodulin (TM), an integral membrane protein on vascular endothelial cells, thrombin undergoes a conformational change such that thrombin loses its procoagulant activity and instead acquires the ability to convert a plasma protein called protein C (PC) to activated protein C (aPC). aPC, a serine protease, acts as a potent anticoagulant by inactivating activated FV (FVa) and FVIII (FVIIIa), two essential cofactors in the clotting cascade. aPC also inactivates plasminogen activator inhibitor-1 (PAI-1), the major physiologic inhibitor of tPA (tissue plasminogen activator), thus potentiating normal fibrinolysis. This mechanism may serve to ensure that blood coagulation remains localized at the site of injury. Infants completely deficient in PC are essentially incompatible with life, with a fatal thrombotic disorder called neonatal purpura fulminans; some patients with a partial deficiency of PC have recurrent thrombosis. In addition, many recent animal models utilizing aPC infusion have shown that exogenous aPC is an anti-thrombotic and anti-inflammatory molecule.

Human thrombin is generated from a precursor polypeptide, prothrombin, of approximately 579 mature amino acids (subject to potential allelic variation or N-terminal microheterogeneity) plus a presequence of about 43 residues (Degen et al., "Biochemistry" 22:2087 [1993]). The presequence is proteolytically removed by the cell during the process of expression and secretion of prothrombin. Prothrombin is a zymogen, or inactive protease, that is activated by proteolytic cleavage. At least three basic sites are subject to cleavage. In vivo, prothrombin is cleaved between residues R271 and T272 (Degen et al. residue numbers) by Factor Xa in the presence of Factor Va, phospholipid and calcium ions to yield prethrombin 2 and Fragment 1.2. Prothrombin also is proteolytically cleaved by the same system between R320 and I321 to yield meizothrombin, which in turn is cleaved autolytically between R155 and S156 to produce Fragment 1 (1–155) and meizothrombin des 1 (a disulfide linked dipeptide extending from residue 156 to the carboxy terminus of prothrombin, cleaved at R323). Finally, thrombin is generated from prethrombin 2 by proteolytic cleavage between R320 and I321, or from meizothrombin des 1 by proteolytic cleavage between R271 and T272. Thrombin itself then autolyzes cleavage between T284 and T285 to generate the mature A-chain N-terminus. For the purposes herein, the mature N-terminal residue of the thrombin A chain (Degen T285) is designated "T1a" and is then numbered consecutively to the arginine residue at R36a. The B chain is numbered from its N-terminal residue I1 (Degen I321) through E259. The two thrombin peptides are covalently bonded by a disulfide linkage between C9a and C119.

Two distinct numbering systems are in use for thrombin, in addition to the DNA-based system of Degen et al. One is based on alignment with chymotrypsinogen (Bode et al., "EMBO J" 8:3467 (1989). A second is favored by Sadler and coworkers at the University of Washington. The Sadler numbering scheme is used in this specification. Under this protocol, the B chain of thrombin commences with I1 and extends to E259, while the A chain is designated with "a" postscripts as noted above, as in T1a to R36a. This thrombin is termed "reference sequence thrombin," and its entire sequence is shown in FIG. 1. For example, Wu et al., ("PNAS USA" 88:6775, (1991)) disclose several thrombin mutants numbered in accordance with the Sadler scheme. The Wu et al. mutants and the corresponding chymotrypsinogen and Degen et al. residue numbers, respectively, are sequentially shown as follows: H43 (57, 363), K52 (60f, 372), N53 (60 g, 373), R62 (67, 382), R68 (73, 388), R70 (75, 390), D99 (102, 419) and S205 (195, 525). SEQ. ID. NO. 2 uses the Sadler system also, but the first residue is the A-chain residue. Numerically, therefore, the residue numbers of SEQ. ID. NO. 2 (and the claims) are shifted 36 higher than elsewhere in this specification.

It is known in the literature that the thrombin binding sites for fibrinogen and protein C activation are overlapping but not identical. This is based on a small number of thrombin mutants (Wu et al., op cit). Wu et al. reported that a polypeptide having the sequence of thrombin but with glutamic acid substituted at position 52 (K52E) was approximately 2.5 fold more active in producing activated PC than wild-type thrombin and possessed only about 17% of the normal fibrinogen clotting activity of wild-type thrombin. Conversely, a polypeptide having the sequence of thrombin but with glutamic acid substituted at position 70 (R70E) reportedly had the fibrinogen clotting activity of wild-type thrombin but only approximately 7% of the PC activating capability of wild-type thrombin. According to Wu et al., the R68E protein essentially lost both functions.

For other polypeptides having sequence homology to thrombin, see Le Bonniec et al., "JBC" 268(25):19055 (1993); Le Bonniec et al., "JBC" 266(21):13796 (1991); Le Bonniec et al., "PNAS USA" 88:7371 (1991); Sheehan et al., "JBC" 268(5):3639 (1993); Horrevoet et al., "JBC" 268(2):779 (1993); Suzuki et al., "JBC" 266(28):18498 (1991); Sheehan et al., "Thrombosis and Haemostasis" 69:Abstract 1784 (1993); Gan et al., "Thrombosis and Haemostasis" 69:Abstract 1783 (1993); Gan et al., "Thrombosis and Haemostasis" 69:Abstract 1787 (1993), and Naray-Szabo et al., "Theochem" 59:401 (1989).

The pivotal role of thrombin in blood clotting has made this protein a target in the development of agents for the treatment of thrombosis. Most efforts have focused on the direct inhibition of the thrombin proteolytic activity, and in fact numerous inhibitors of the procoagulant activities of thrombin have an anticoagulant effect (Hirsh, 1991; Hirsh, 1991a). However, the potency of these inhibitors may be limited by the concomitant inhibition of the anticoagulant activity of thrombin. Conversely, anticoagulant effect has been achieved by augmenting or stimulating the thrombin anticoagulant pathway, i.e., by administration of soluble TM (Gomi, et al., "Blood" 75:1396–1399, 1990; and Light, D., WO 93/15755) or activated protein C ("aPC") Dreyfus et al., 1991; Gruber et al., 1990; Gruber et al., 1991; Taylor et al., 1987). This strategy does not block ongoing coagulation resulting from previously activated thrombin.

It is an object of this invention to prepare novel polypeptides which possess enhanced physiochemical or biological activities.

A further object of this invention is to prepare novel polypeptides in which the procoagulant and anticoagulant activities of thrombin have been substantially segregated, and which also optionally resist heparin-mediated antithrombin III (AT-III) inhibition.

Another object is to obtain such polypeptides that can be expressed in elevated yields in recombinant cell culture.

An additional object of this invention is to provide novel polypeptides that are substrate specific for protein C activation or fibrinogen, but do not substantially proteolyze polypeptides that normally are not thrombin substrates.

Another object of this invention is to provide novel covalently-modified polypeptides that are useful in screening for substances that are agonists or antagonists of thrombin's procoagulant or anticoagulant activities.

A further object is to provide novel polypeptides that activate protein C but are substantially incapable of, or have reduced proteolytic activity against any one or more of fibrinogen, the thrombin platelet receptor, and/or Factors XIII, V, XI or VIII.

A still further object is to obtain novel polypeptides useful in purifying thrombin-interactive polypeptides such as TM or aPC from cell culture or native sources.

Another object is to identify novel polypeptides retaining at least a substantial degree of the desired proteolytic activity of thrombin, including the kcat and Km of thrombin for the desired substrate.

In a further object, novel polypeptides are provided that exhibit enhanced PAI-1 inactivating activity as compared to wild-type thrombin.

A further object is to provide a method for identifying deficiencies in thrombomodulin function in patients with clotting disorders.

In other objects, novel polypeptides are provided for the treatment of thrombosis, in particular thrombosis associated with septic shock, for the therapy of solid tumors and for the preparation of improved dressings for wounds, or for therapies and diagnostic utilities that rely upon a property of thrombin.

Another object is to identify novel analogues of thrombin that have an enhanced or reduced ability to stimulate cell proliferation (Ben-Sharit et al., "PNAS USA" 83:976–980 (1986)).

These and other objects of the invention will be apparent from consideration of this specification as a whole.

SUMMARY OF THE INVENTION

This invention is concerned with novel polypeptides (hereafter "NPs") in which the properties of thrombin are segregated, i.e., where the polypeptides fail to possess to a substantial degree one or more undesired properties of thrombin yet still retain one or more desirable property of thrombin. In addition, this invention is concerned with NPs in which targeted thrombin residues have been mutagenized.

Specifically excluded from the scope of the NPs are known amino acid sequence variants of thrombin, specifically thrombin R70E, thrombin R68E, thrombin K154A, thrombin K252E, thrombin K174E, thrombin R180E, thrombin D99A, thrombin D99N, thrombin E202Q, thrombin E25K, thrombin R245E, thrombin S205A, R197E, D199E, thrombin N151D, K154E, thrombin desP48,P49, W50, thrombin desE146,T147,W148, thrombin desT147-S158, the thrombins of WO 93/13208 in which at least one amino acid residue within the thrombin activation site has been mutated, and thrombin in which loop F19-E25 is replaced by the equivalent loop from tissue plasminogen activator. However, thrombin K52E is only excluded to the extent that its manufacture is enabled by the prior art. Activation site variant thrombins are excluded only to the extent the term "activation site" is defined and disclosed in WO 93/13208. Also excluded from the scope of the novel polypeptides of this invention are the fusions of such known thrombins with a nonthrombin polypeptide or a prepro-thrombin or prothrombin polypeptide. Not excluded from the scope of NPs, however, are NPs representing known thrombins in which additional amino acid substitutions, insertions or deletions have been made.

Also excluded from the scope of the novel polypeptides are naturally-occurring thrombins, whether from humans or animals (including naturally-occurring alleles), which have not been isolated or purified from blood or other body tissue, i.e., which are products of nature. It will be understood, however, that the NPs of this invention include allelic variations from the thrombin reference sequence in addition to the contemplated mutations herein.

In certain embodiments of this invention, we provide novel, proteolytically active polypeptides which have a ratio of protein C activation to fibrinogen clotting that differs from wild-type thrombin. In particular, we provide two general classes of novel polypeptides. In the first class, called "Protein C Activators", or "PCA", we provide novel polypeptides that possess a ratio of anticoagulant activity to procoagulant activity of great than about 2. PCA polypeptides are able to activate protein C but are substantially unable to cleave fibrinogen. Surprisingly, our experimental studies in animals demonstrate that even residual levels of procoagulant activity in PCA are well-tolerated and do not result in any evidence of disseminated intravascular coagulation or other clinically adverse procoagulant responses. Moreover, we have unexpectedly been able to identify PCA that are devoid of any detectable procoagulant activity in our assay but still are capable of substantial Protein C activation. Thus, an embodiment of this invention comprises administering to a subject in need of anticoagulant therapy a therapeutically effective dose of an PCA.

In an extension of the foregoing embodiment, an PCA is prepared and administered whose anticoagulant activity is substantially resistant to inhibition by a predetermined thrombin inhibitor, for example heparin and AT-III. In one embodiment the PCA is administered in vivo in conjunction with heparin. Heparin inhibits the procoagulant activity of endogenous thrombin without affecting the anticoagulant activity of the PCA, thereby resulting in a potent anticoagulant effect. This embodiment of the invention has the additional advantage in that the administered PCA is expected to be resistant to AT-III—heparin clearance in vivo and thus will exhibit a longer biological half-life.

In other embodiments PCAs are provided that have reduced proteolytic activity towards the platelet thrombin receptor and thus do not activate platelets at therapeutic doses. PCAs are provided that have an EC50 for the stimulation of platelet aggregation of greater than 10 nM, ordinarily greater than 20 nM. EC50s greater than that of wild-type thrombin reduce or eliminate detectable platelet aggregation by the PCA when the PCA is used at doses capable of activating Protein C.

A second group of novel polypeptides of this invention are termed "Fibrinogen Clotting Proteins" or "FCP". These polypeptides possess a ratio of anticoagulant activity to procoagulant activity of less than 05. These NPs contain mutations in the protein C activating domains of thrombin which reduce the anticoagulant activity of the resulting polypeptide to less than about half that of wild-type thrombin, but retain the ability to clot fibrinogen. These polypeptides are useful, for example, in diagnostics, preparative methods and hemostastic surgical articles. A further embodiment of this invention comprises administering to a subject in need of procoagulant therapy a therapeutically effective dose of an FCP.

To the extent that any enabling disclosure of an FCP or PCA has appeared in the prior art literature, such prior art polypeptides are useful in the foregoing therapeutic methods of this invention.

In one embodiment we have provided PCA polypeptides wherein an amino acid residue of a thrombin polypeptide has been substituted, deleted or a residue inserted adjacent to one or more of thrombin residues W50, K52, D58, K65, H66, Y71, N74, K106, K107, S176, T177, W227, D193, K196, E202, E229, R233, D232, D234, K236, Y237 or F239.

In another embodiment we have provided FCP polypeptides wherein an amino acid residue of a thrombin polypeptide has been substituted, deleted or a residue inserted adjacent to one or more of the thrombin residues K21, Q24, R70, R98 or K77.

Another embodiment of this invention facilitates the specific diagnosis of various idiopathic thrombotic disorders. This embodiment is a method comprising contacting a subject's blood and vascular tissue with a diagnostically effective dose of an PCA, and thereafter measuring a hemostatic parameter of the subject's blood to determine whether a defect exists in the subject's aPC pathway.

BRIEF DESCRIPTION OF THE DRAWINGS

FIGS. 1A–1C depicts the nucleotide sequence for DNA encoding reference sequence thrombin (also referred to as wild-type thrombin), its complementary sequence, and the deduced amino acid sequence of reference sequence thrombin.

FIG. 4 compares the anticoagulant activities of two doses of a novel polypeptide of this invention (PCA-2, E229A PCA) in cynomolgus monkeys.

DETAILED DESCRIPTION OF THE INVENTION

Figure 2A:
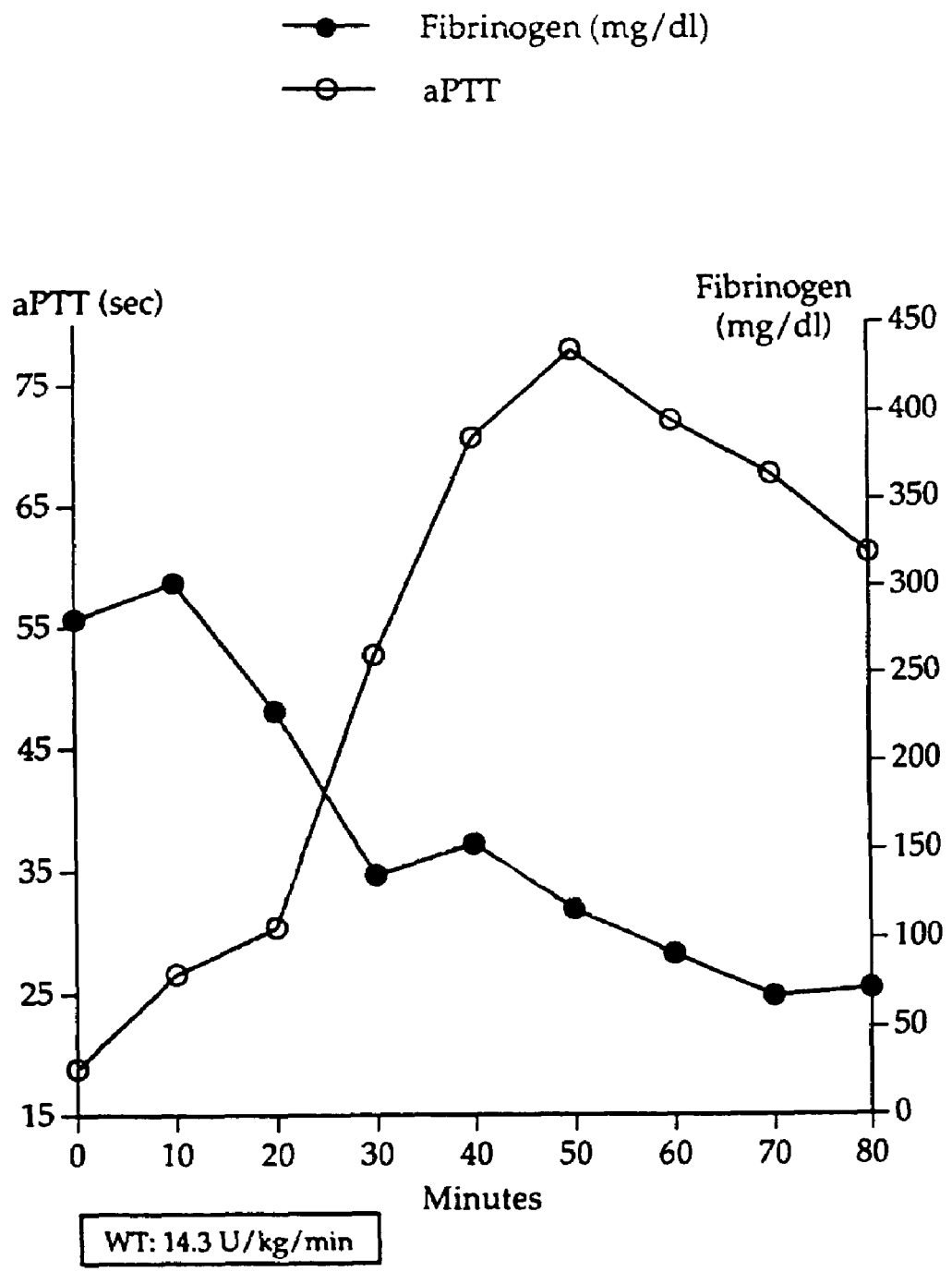
FIGS. 2A and 2B compare the activities in rabbits of recombinant wild-type human thrombin (FIG. 2A) and the K52A PCA (FIG. 2B). This study shows that the novel polypeptide, in comparison to wild-type human thrombin, produces no significant reduction in circulating fibrinogen but is able to induce anticoagulation, as measured by the activated PTT assay.

The novel polypeptides of this invention have a polypeptide sequence that is at least about 80% homologous by amino acid sequence (ordinarily at least about 90%, and preferably at least about 95%) with reference sequence thrombin, but have a significant qualitative or quantitative property not possessed by reference sequence thrombin, as described elsewhere herein.

"Homology" is defined as the percentage of residues in a candidate amino acid sequence that are identical with the residues in the reference sequence thrombin after aligning the two sequences and introducing gaps, if necessary, to achieve the maximum percent homology. Methods and computer programs for the alignment are well known in the art. One computer program which may be used or adapted for purposes of determining whether a candidate sequence falls within this definition is "Align 2", authored by Genentech, Inc., which was filed with user documentation in the United States Copyright Office, Washington, D.C. 20559, on Dec. 10, 1991.

In calculating amino acid sequence homology the candidate and reference sequences are aligned in the fashion that produces the maximum number of aligned residues, with insertions and deletions of residues represented by gaps in the aligned sequences. For example, a 120 residue polypeptide containing a 100 residue thrombin reference sequence fragment fused at its N-terminus to a heterologous 20 residue, bacterial signal sequence, but with a single substitution in the thrombin fragment, is calculated to be 99% homologous to the thrombin reference sequence since the sequence of the fragment corresponds exactly to the maximally aligned thrombin reference sequence except for a single residue substitution and the 20 residue N-terminal fusion. Thus, if the alignment-maximizing comparison of the candidate and reference sequences reveals an insertion (or deletion) of one or more amino acid residues, then these residues are ignored for the purposes of making the homology calculation.

In another example, the designation "E202A NP" as used herein means that the polypeptide so designated includes alanine substitution at thrombin B-chain site 202 including any of the following: mature human thrombin B chain (free of the A chain), human prothrombin containing both A and B chain, a fusion of a bacterial polypeptide with the human B chain thrombin, or a site 202-containing fragment of the human thrombin B chain, so long as each of these derivatives retains the capability of activating protein C or cleaving fibrinogen to produce a clot, or can be processed to do so. Fragments of thrombin A or B chains, in particular of the B chain are included as well, again provided that the polypeptide in its entirety at least is capable of activating protein C or cleaving fibrinogen to produce a clot. Fragments of thrombin range from about 10, 20, 30, 50, 100 or more residues. Generally, NPs that contain more than one substitution in the thrombin sequence also will include the intervening thrombin sequence.

Analysis of homology is based on any one or more of the sequence imputed from the nucleic acid used to express the NP, the sequence of the product as first produced in vitro, or the sequence after any post-translational modification. Thus, if the reference and candidate sequences are identical when expressed, but a glutamine residue is later deaminated to glutamic acid, the first candidate is 100% homologous, but the deaminated sequence is not.

For the purposes herein "procoagulant activity" is defined as the activity determined by the fibrinogen clotting assay of Example 2.3, corrected to normalize the concentration of NP and corresponding wild-type thrombin.

For the purposes herein "anticoagulant activity" is defined as the activity determined by the protein C activation assay of Example 2.4, corrected to normalize the concentration of NP and corresponding wild-type thrombin.

The concentration of NP and thrombin is determined by any suitable assay. Table 1a below reports results in which the concentrations of NP and thrombin proteins are inferred from amidolytic activity. However, an immunoassay also is satisfactory for this purpose. For example, immobilized PPAK can be used to capture the NP and thrombin, and the bound proteins detected by labeled anti-thrombin antibody. If the NP or thrombin is substantially homogeneous then gross protein assays such as the well-known Lowry method can be used to determine their concentration in the test sample.

The "corresponding" wild-type thrombin means a protein that is made by essentially the same method as the analyte NP was made and has the same sequence as the NP except that mutations found in the NP are reverted back to the sequence found in reference sequence thrombin.

In some embodiments novel polypeptides possess (a) at least one immune epitope that is capable of substantial cross-reaction with an antibody raised against reference sequence thrombin, (b) two chains homologous to the A and B chains of the reference sequence thrombin that are bonded by a single disulfide linkage, (c) the thrombin active site residues S205, H43 and D99, (d) a kcat for fibrinogen or protein C, as the case may be, which is at least about 20% of, preferably at least about 75% of and most preferably greater than equal to that of the reference sequence, (e) a Km for fibrinogen or protein C, as the case may be, which is at most about 150%, preferably at most about 100% and most preferably at most about 50%, and preferably at least about 75%, of that of the reference sequence, (f) proteolytic activity as measured by S-2238 hydrolysis that is greater than about 50% of the reference sequence thrombin, preferably greater than about 75% and most preferably greater than about 90% of the reference sequence thrombin, and/or (g) which essentially has no broader substrate specificity than reference sequence thrombin, e.g., which is able to cleave human proteins other than the native thrombin substrates in vivo at a rate of no more than about 150%, and preferably no more than about 120% of the reference sequence.

The PCA of this invention typically possess (a) procoagulant activity that is equal to or less than about 50, 25, 15, 10, 9, 8, 7, 6, 5, 4, 3, 2, or 1% of reference sequence thrombin, (b) a ratio of anticoagulant activity to procoagulant activity that is greater than about 2, 3, 4, 5, 6, 7, 8, 9, 10, 15, 25 or 50 when compared with reference sequence thrombin, and (c) anticoagulant activity that is equal to or greater than about 5, 10, 15, 25, 50, 75 or 100% of the anticoagulant activity of reference sequence thrombin.

The FCP of this invention typically possess (a) anticoagulant activity that is equal to or less than about 50, 25, 15, 10, 9, 8, 7, 6, 5, 4, 3, 2, or 1% of reference sequence thrombin, (b) a ratio of anticoagulant activity to procoagulant activity that is less than about 0.5, 0.25, 0.15, 0.10, 0.09 or 0.08, when compared with reference sequence thrombin, and (c) procoagulant activity that is equal to or greater than about 5, 10, 15, 25, 50, 75 or 100% of the procoagulant activity of reference sequence thrombin.

The novel polypeptides of this invention comprise substitutions for, deletions of, or insertions of any amino acid residue adjacent to, any of the reference sequence amino acid residue sites shown in Table 1 or 1b below. Table 1 depicts the results of a study in which thrombin residues have been substituted with alanine. Substitutional NPs are those in which at least one amino acid residue in the reference sequence has been removed and a different amino acid inserted in its place at the same position. The substitutions may be single, where only one amino acid in the molecule has been substituted, or they may be multiple, where two or more amino acids have been substituted at 2 or more thrombin sites. The Table 1 columns, from left to right, depict our code number, the residues substituted, two columns of S-2238 hydrolysis data (a measure of the proteolytic activity of thrombin and an indicia of the conformational disruption occasioned by the substitution), fibrinogen clotting (a measure of procoagulant activity), protein C activation (a measure of anticoagulant activity), the ratio of protein C activation to fibrinogen clotting activity, and heparin-dependent AT-III inhibition (a measure of the ability of the NP to withstand inactivation by AT-III in the presence of heparin). Expression in our system of NPs Mt3 and Mt37c could not be detected.

TABLE 1

| NPs Unit | Residues Substituted with Alanine | Chymo-trypsinogen Numbering | Sp Amidolytic Ac Slot Blot % of wild type | Sp Amidolytic Ac Western Blot % of wild type | Fibrinogen Clotting (FC) % of wild type | Protein C Activation (PA) % of wild type | PA/FC | Heparin-dependent ATIII Inhibition % Residual Activity |
|---|---|---|---|---|---|---|---|---|
| Wild Type | | | 99.09 | 100.00 | 100.00 | 100.00 | 1.00 | 18.15 |
| Mt1 | S4a, E6a, D8a | 1E, 1C, 1A | 281.58 | 58.32 | 165.45 | 93.07 | 0.56 | |
| Mt2 | K17a, K18a, S19a | 9, 10, 11 | 104.78 | 99.27 | 84.78 | 96.94 | 1.14 | |
| Mt3 | K23a, R26a, E27a | 14A, 14D, 14E | — | — | — | — | — | |
| Mt3a | K23a | 14A | 111.94 | 91.46 | 110.54 | 87.39 | 0.79 | |
| Mt3b | R26a | 14D | 96.42 | 79.02 | 92.48 | 99.36 | 1.07 | |
| Mt3c | E27a | 14E | 61.87 | 70.23 | 46.34 | 59.74 | 1.29 | |
| Mt4 | E30a, D34a | 14H, 14L | 96.97 | 93.86 | 80.08 | 102.71 | 1.28 | |
| Mt5 | E3, D6 | 18, 21 | 101.61 | 93.44 | 85.57 | 97.23 | 1.14 | |
| Mt6 | R20 | 35 | 136.11 | 92.16 | 79.95 | 67.73 | 0.85 | |
| Mt7 | K21 | 36 | 92.13 | 90.77 | 30.91 | 14.24 | 0.46 | |
| Mt8 | S22, Q24, E25 | 37, 38, 39 | 129.96 | 90.30 | 158.49 | 11.85 | 0.07 | |

TABLE 1-continued

| NPs Unit | Residues Substituted with Alanine | Chymo-trypsinogen Numbering | Sp Amidolytic Ac Slot Blot % of wild type | Sp Amidolytic Ac Western Blot % of wild type | Fibrinogen Clotting (FC) % of wild type | Protein C Activation (PA) % of wild type | PA/FC | Heparin-dependent ATIII Inhibition % Residual Activity |
|---|---|---|---|---|---|---|---|---|
| Mt8a | S22 | 37 | 109.65 | 69.36 | 74.82 | 47.90 | 0.64 | |
| Mt8b | Q24 | 38 | 122.15 | 70.13 | 135.51 | 12.54 | 0.09 | |
| Mt8c | E25 | 39 | 101.06 | 81.87 | 119.98 | 104.42 | 0.87 | |
| Mt9 | D35 | 49 | 233.65 | 92.52 | 133.46 | 112.81 | 0.85 | |
| Mt10 | W50, D51 | 60D, 60E | 43.73 | 76.57 | 12.68 | 24.98 | 1.97 | |
| Mt10a | W50 | 60D | 49.37 | 71.40 | 5.15 | 35.56 | 6.90 | |
| Mt10b | D51 | 60E | 110.80 | 75.17 | 96.50 | 69.08 | 0.72 | |
| Mt11 | K52 | 60F | 122.22 | 85.22 | 38.17 | 134.70 | 3.53 | |
| Mt12 | N53, T55 | 60G, 60I | 76.22 | 70.51 | 42.60 | 99.58 | 2.34 | |
| Mt13 | N57, D58 | 62, 63 | 83.94 | 90.14 | 47.90 | 71.77 | 1.50 | |
| Mt13a | N57 | 62 | 96.64 | 92.93 | 75.17 | 100.14 | 1.33 | |
| Mt13b | D58 | 63 | 93.34 | 71.98 | 58.11 | 87.75 | 1.51 | |
| Mt14 | K65 | 70 | 110.97 | 100.76 | 1.85 | 5.64 | 3.04 | |
| Mt14.5 | H66 | 71 | 55.45 | 103.45 | 2.00 | 12.30 | 6.14 | |
| Mt15 | R68 | 73 | 99.53 | 78.01 | 20.25 | 34.12 | 1.68 | |
| Mt16 | T69 | 74 | 120.84 | 107.33 | 77.04 | 58.26 | 0.76 | |
| Mt17 | R70A | 75 | 108.39 | 93.34 | 77.51 | 14.01 | 0.18 | |
| Mt17a | R70E | 75 | 105.69 | 95.31 | 76.86 | 63.29 | 0.82 | |
| Mt17b | R68, R70 | 73, 75 | 109.32 | 69.25 | 6.70 | 13.31 | 1.99 | |
| Mt18 | Y71 | 76 | 87.95 | 102.03 | 0.31 | 5.28 | 17.11 | |
| Mt19 | R73 | 77A | 91.74 | 99.34 | 16.65 | 26.38 | 1.58 | |
| Mt20 | N74, K77 | 78, 81 | 127.70 | 124.90 | 10.59 | 12.92 | 1.22 | |
| Mt20a | N74 | 78 | 94.97 | 86.47 | 59.33 | 82.47 | 1.39 | |
| Mt20b | K77 | 81 | 80.46 | 82.47 | 27.05 | 12.71 | 0.47 | |
| Mt21 | E82, K83 | 86, 87 | 124.83 | 139.61 | 71.83 | 62.45 | 0.87 | |
| Mt22 | R89, R93, E94 | 93, 97, 97A | 142.67 | 95.11 | 54.92 | 61.10 | 1.11 | 59.24 |
| Mt22.5 | R98 | 101 | 186.13 | 46.67 | 124.06 | 62.50 | 0.50 | |
| Mt23 | K106, K107 | 109, 110 | 107.35 | 102.01 | 13.15 | 31.42 | 2.39 | |
| Mt23a | K106 | 109 | 86.92 | 93.24 | 50.25 | 72.35 | 1.44 | |
| Mt23b | K107 | 110 | 106.96 | 92.38 | 46.93 | 44.92 | 0.96 | |
| Mt24 | D113 | 116 | 122.36 | 90.97 | 80.15 | 88.41 | 1.10 | |
| Mt25 | D122, R123, E124 | 125, 126, 127 | 92.57 | 71.47 | 84.21 | 84.44 | 1.00 | |
| Mt26 | S128, Q131 | 129B, 131 | 75.74 | 109.30 | 85.40 | 89.80 | 1.05 | |
| Mt27 | K145, T147, W148 | 145, 147, 148 | 111.11 | 98.07 | 65.81 | 84.40 | 1.28 | |
| Mt28 | T149, N151 | 149, 149B | 81.88 | 98.90 | 74.36 | 76.63 | 1.03 | |
| Mt29 | K154 | 149E | 88.57 | 87.07 | 118.76 | 95.47 | 0.80 | |
| Mt30 | S158 | 153 | 86.86 | 92.30 | 97.96 | 97.50 | 1.00 | |
| Mt31 | E169, K174, D175 | 164, 169, 170 | 111.22 | 205.21 | 43.97 | 69.56 | 1.58 | 32.86 |
| Mt32 | R178, R180, D183 | 173, 175, 178 | 61.62 | 58.44 | 90.35 | 102.37 | 1.13 | 56.52 |
| Mt33 | D193, K196 | 186A, 186D | 99.65 | 108.75 | 28.87 | 60.27 | 2.09 | |
| Mt34 | E202 | 192 | 40.33 | 25.40 | 37.22 | 93.81 | 2.52 | |
| Mt35 | N216, N217 | 204B, 205 | 177.29 | 92.87 | 41.64 | 77.56 | 1.86 | |
| Mt36 | E229, R233, D234 | 217, 221, 222 | | 0.75 | 0.00 | 0.00 | | |
| Mt36a | E229 | 217 | 42.70 | 23.73 | 0.58 | 13.22 | 22.91 | |
| Mt36b | R233 | 221 | 75.90 | 83.93 | 2.31 | 25.16 | 10.87 | |
| Mt36c | D234 | 222 | 51.82 | 75.33 | 27.37 | 59.64 | 2.18 | |
| Mt37 | R245, K248, Q251 | 233, 236, 239 | | 0.73 | 0.00 | 0.00 | | |
| Mt37a | R245 | 233 | 135.96 | 26.22 | 72.57 | 70.39 | 0.97 | |
| Mt37b | K248 | 236 | 143.41 | 73.41 | 76.89 | 76.86 | 1.00 | |
| Mt37c | W249 | 237 | — | — | — | — | — | |
| Mt37d | Q251 | 239 | 105.24 | 96.55 | 60.45 | 68.79 | 1.14 | |
| Mt38 | K252, D255, Q256 | 240, 243, 244 | 92.80 | 94.98 | 65.07 | 63.74 | 0.98 | |

The most salient parameter of Table 1 is the PA/FC ratio. The more this ratio varies from 1.0, the greater the segregation of procoagulant and PC activating properties in the mutants. Those with the highest arithmetic value are particularly dedicated to PC activation, while those with the lowest value are dedicated to procoagulant function. However, it is within the scope of this invention to substitute additionally any amino acid residue other than alanine at the Table 1 sites, e.g. one of the 20 naturally occurring residues disclosed below. For optimal anticoagulant therapeutic utilities the PC activating capabilities of the NP should be at least about 5%, ordinarily 10%–30%, of reference sequence thrombin, notwithstanding the PA/FC ratio, so that one can ensure that sufficient activity of the enzyme will be present to exert a physiological or diagnostic effect. In addition, the absolute fibrin clotting activity of the PCA ideally should be less than about 10% of reference thrombin, generally less than about 5% and ordinarily less than about 3% and preferably less than about 1% of wild-type, to help ensure clinical safety. It is not necessary that the NP retain the same level of protein C activating activity as reference sequence thrombin because lower potency is readily overcome in therapy by simply administering more of the enzyme. In this regard the E229 and R233 PCAs are particularly attractive.

In addition to the alanine substitutions shown in Table 1, it is within the scope of this invention to substitute other residues into the thrombin reference sequence. The residues inserted into the sequence generally are naturally occurring amino acids, commonly G, A, Y, V, L, I, S, T, D, E, Q, C, M, N, F, P, W, K, R or H (using conventional single letter code; EP 323,149). Suitable residues for insertion also include hydroxyproline, beta-hydroxyaspartic acid, gamma-carboxyglutamic acid, hydroxylysine or norleucine, to be employed as alternatives to their namesakes.

These substitutions may be conservative in that the substituting residue will be bear structural or functional similarity to the substituted residue. Other substitutions will be less conservative in that they constitute an exchange between different structural or functional classes of residues. For the purposes herein, these classes are as follows: 1. Electropositive: R, K, H; 2. Electronegative: D, E; 3. Aliphatic: V, L, I, M; 4. Aromatic: F, Y, W; 5. Small: A, S, T, G, P, C; 6. Charged: R, K, D, E, H; 7. Polar: S, T, Q, N, Y, H, W; and 8. Small Hydrophilic: C, S, T. Intergroup substitutions generally will have greater effects on protein function than conservative (intraclass) substitutions. Thus, it is particularly within the scope of this invention to introduce conservative substitutions into the Table 1 or 1b sites and, if the results are not satisfactory, to introduce non-conservative substitutions at the sites. Typically, however, proline, glycine, and cysteine substitutions or insertions into the sequence are not favored.

An object of this invention is to obtain NPs that are minimally immunogenic or non-immunogenic in humans. In this regard, substitutions or insertions of K or R residues into the sequence are not favored.

Substitutions preferably are made at Table 1 sites where alanine substitution results in a PA/FC ratio that is greater than 2.0 or less than 0.5 (W50, K52, D58, K65, H66, Y71, N74, E202, E229, R233, D234, K21, Q24, R70, R98 and K77). Four of these sites were selected for saturation mutagenesis (E229, R233, W50 and K52). In addition, double and triple mutations variously were introduced into sites W50, K52, R233, E229, E202, K106, K107, D193 and K196. These NPs were prepared and expressed in recombinant cell culture in the same fashion as the Table 1 mutants, and then assayed for expression levels, amidolytic activity, aPC and fibrinogen clotting activity. The results are shown in Table 1a ("INF"=approaches infinity; blank NPs have not yet been characterized).

TABLE 1a

| NPs Unit | Expression Level % of wild type | Sp Amidolytic Ac Western Blot % of wild type | Protein C Activation (PA) % of wild type | Fibrinogen Clotting (FC) % of wild type | PA/FC Ratio |
|---|---|---|---|---|---|
| S205A | 83.50 | 0.26 | 0.01 | 0.00 | |
| WT | 100.00 | 100.00 | 100.00 | 100.00 | 1.00 |
| W50A/K52A | 24.50 | 94.90 | 77.57 | 6.87 | 11.28 |
| W50A/E229A | 55.50 | 7.28 | 1.45 | 0.00 | INF |
| W50A/R233A | 3.90 | 267.50 | −0.13 | 0.00 | 0.00 |
| K52A/E202A | | | | | |
| K52A/E229A | 4.30 | 41.87 | 6.79 | | |
| K52A/R233A | 14.40 | 94.29 | 18.50 | 0.00 | INF |
| K52A/K106A/K107A | 2.20 | 171.02 | 15.92 | | |
| K52A/D193A/K196A | | | | | |
| E229A/R233A | 45.00 | 10.90 | 0.57 | 0.00 | INF |
| E229A | 62.50 | 33.44 | 5.25 | 0.33 | 15.81 |
| E229C | 0.00 | | | | |
| E229D | 45.00 | 185.00 | 10.21 | 0.00 | INF |
| E229F | 11.00 | 40.57 | 2.89 | 0.00 | INF |
| E229G | 100.00 | 3.48 | −2.97 | 0.00 | 0.00 |
| E229H | | | | | |
| E229I | | | | | |
| E229K | 16.00 | 23.29 | 3.95 | | |
| E229L | 22.50 | 79.20 | 44.62 | 20.98 | 2.13 |
| E229M | | | | | |
| E229N | 61.00 | 101.83 | 12.19 | | |
| E229P | 113.00 | 6.26 | 1.84 | 0.00 | INF |
| E229Q | | | | | |
| E229R | | | | | |
| E229S | 30.00 | 52.91 | 25.83 | 0.53 | 48.75 |
| E229T | 16.00 | 56.36 | 14.37 | 5.32 | 2.70 |
| E229V | 16.00 | 58.25 | 9.16 | 12.62 | 0.73 |
| E229W | 20.00 | 34.57 | 29.05 | 0.00 | INF |
| E229Y | 8.50 | 38.17 | 33.43 | 0.00 | INF |
| R233A | 81.00 | 113.71 | 55.04 | 3.04 | 18.11 |
| R233C | 52.00 | 58.06 | 6.38 | 0.00 | INF |
| R233D | 75.00 | 84.93 | 15.20 | 0.00 | INF |
| R233E | 52.00 | 229.46 | 67.61 | 1.04 | 65.10 |
| R233F | 100.00 | 59.91 | 9.24 | 0.00 | INF |
| R233G | 50.00 | 110.77 | 10.25 | 0.87 | 11.76 |
| R233H | 96.00 | 94.96 | 25.15 | 4.59 | 5.48 |
| R233I | 77.50 | 73.22 | 31.36 | 6.27 | 5.00 |
| R233K | | | | | |
| R233L | 96.00 | 79.47 | 10.82 | 7.15 | 1.51 |
| R233M | 200.00 | 46.78 | 10.04 | 1.15 | 8.69 |
| R233N | 52.00 | 242.15 | 80.61 | 1.06 | 76.12 |
| R233P | 50.00 | 5.49 | −0.74 | 0.00 | 0.00 |
| R233Q | 96.00 | 91.05 | 14.90 | 4.96 | 3.00 |
| R233S | 80.00 | 94.86 | 12.87 | 0.90 | 14.33 |
| R233T | 80.00 | 98.91 | 6.95 | 1.46 | 4.76 |
| R233V | 50.00 | 122.85 | 28.02 | 23.15 | 1.21 |
| R233W | 0.00 | | | | |

TABLE 1a-continued

| NPs Unit | Expression Level % of wild type | Sp Amidolytic Ac Western Blot % of wild type | Protein C Activation (PA) % of wild type | Fibrinogen Clotting (FC) % of wild type | PA/FC Ratio |
|---|---|---|---|---|---|
| R233Y | 106.00 | 27.46 | −0.83 | 0.00 | 0.00 |
| W50A | 53.60 | 123.04 | 50.84 | 5.17 | 9.83 |
| W50C | 25.00 | 48.63 | 20.38 | 0.00 | INF |
| W50D | 32.46 | 220.03 | 9.99 | 7.64 | 1.30 |
| W50E | 36.36 | 185.62 | 9.30 | 0.00 | INF |
| W50F | 22.08 | 112.74 | 91.55 | 49.44 | 1.85 |
| W50G | 50.00 | 160.05 | 55.51 | 6.08 | 9.13 |
| W50H | 8.05 | 222.75 | 16.47 | 39.28 | 0.42 |
| W50I | | | | | |
| W50K | 82.72 | 65.39 | 61.38 | 3.27 | 18.77 |
| W50L | 60.00 | 172.05 | 103.19 | 10.97 | 9.41 |
| W50M | 50.00 | 149.44 | 81.72 | 14.06 | 5.81 |
| W50N | 3.90 | 1078.41 | 27.48 | 3.46 | 7.94 |
| W50P | 0.00 | | | | |
| W50Q | 120.00 | 134.58 | 52.80 | 24.93 | 2.12 |
| W50R | 40.00 | 107.57 | 201.34 | 23.75 | 8.48 |
| W50S | 16.88 | 255.68 | 36.81 | 9.12 | 4.04 |
| W50T | 60.00 | 139.15 | 48.19 | 14.65 | 3.29 |
| W50V | 9.09 | 229.78 | 18.06 | 2.33 | 7.75 |
| W50Y | 40.00 | 184.77 | 195.64 | 65.05 | 3.01 |
| K52A | 41.50 | 125.60 | 151.70 | 48.77 | 3.11 |
| K52C | 40.00 | 8.92 | 5.17 | 0.00 | INF |
| K52D | 0.00 | | | | |
| K52E | 0.00 | | | | |
| K52F | 12.98 | 313.25 | 86.15 | 20.41 | 4.22 |
| K52G | 0.00 | | | | |
| K52H | 155.00 | 64.46 | 153.40 | 31.27 | 4.91 |
| K52I | 4.00 | 483.02 | 225.74 | 144.68 | 1.56 |
| K52L | 26.40 | 134.75 | 216.98 | 170.79 | 1.27 |
| K52M | 50.00 | 51.07 | 70.05 | 65.38 | 1.07 |
| K52N | 32.00 | 47.56 | 72.77 | 28.69 | 2.54 |
| K52P | 0.00 | | | | |
| K52Q | 93.50 | 74.21 | 85.14 | 64.08 | 1.33 |
| K52R | 480.00 | 41.54 | 22.31 | 9.47 | 2.36 |
| K52S | 48.00 | 71.61 | 167.01 | 48.06 | 3.48 |
| K52T | 86.00 | 66.63 | 140.99 | 70.48 | 2.00 |
| K52V | 70.00 | 72.06 | 210.17 | 87.30 | 2.41 |
| K52W | 41.00 | 124.20 | 30.24 | 6.46 | 4.68 |
| K52Y | 26.40 | 51.60 | 73.37 | 36.08 | 2.03 |

The data in Table 1a were obtained as provided in Table 1, and that the activities (protein C activation and fibrinogen clotting) were normalized by amidolytic activity, except that in Table 1a when the specific amidolytic activity of NP was less than 75% of corresponding wild type thrombin, the NP activity values for protein C activation and fibrinogen clotting were corrected by multiplying by the corresponding specific amidolytic activity of the NP (expressed as % of wild type). It will be noted that the numerical values for PA and FC activity differ between Tables 1 and 1a for NPs appearing in both Tables. This is the result of two factors. First, the Table 1a results generally represent the outcome of only 1 or 2 replicate assays, whereas those of Table 1 are based on up to 4 replicates. Since the coefficient of variation of the PA and FC assays is in the range of about 10–20%, the Table 1a results can be expected to vary from those of Table 1 for the same NPs. Second, the Table 1a results were corrected for protein concentration based on Western blotting if the amidolytic activity was less than 75% of wild-type thrombin, as described above. This allows for a more meaningful comparison among the various NPs in Table 1a since the results are corrected to the same protein concentration as determined by Western blot. Correction was largely unnecessary with the Table 1 NPs because, for the most part, the alanine mutants retained most of the proteolytic activity of reference sequence thrombin.

Particularly remarkable PCAs were identified in Table 1a; the data indicates retention of at least some aPC activity but essentially complete elimination of detectable FC activity in our assay (600 seconds without clotting). These were the double mutants W50A,E229A and E229A,R233A; and the single mutants E229D (which remarkably only differs from the wild type enzyme by a single methylene group), E229F, E229S, E229W, E229Y, R233E, R233G, R233M, R233N, R233S, W50E, W50K, W50C, and K52C.

The Table 1 and 1a PCAs are only representative of NPs in which thrombin residues are mutated in order to produce particularly safe and potent PCAs. Other such PCAs are readily identified by the methods described herein or other methods apparent to the ordinary artisan. For example, multiple sites of variation are selected by additivity of activities, and other promising sites identified by alanine scanning are subjected to saturation mutagenesis to select the optimal modification. Since it is apparent that other NPs having the desired procoagulant and anticoagulant properties can be successfully identified, it would be merely a matter of routine experimentation to identify and isolate them.

It is apparent from Tables 1 and 1a that E229 and R233 are key residues for PCAs. The modification of thrombin residues in Van der Waals contact with E229 or R233, residues near E229 or R233 and residues in contact with the domain containing R233 and the loop that contains E229 may affect fibrinogen clotting and protein C activation in a manner analogous to the direct substitution of E229 or R233 by causing the position or orientation of E229 or R233 to change, or by disrupting intramolecular interactions normally associated with E229 or R233. In order to identify residues whose substitution might mimic the substitution of E229, the residues in close proximity to E229 in the three-dimensional structure of thrombin (Bode, W. et al, *EMBO J.* 8:3467:3475 (1989)) were mapped. Residues whose Cα was within a 10 Å sphere surrounding the Cα of E229 are listed in Table 1b below.

TABLE 1b

| Residue | Distance Cα to Cα E229 (Å) | Mutation in Table 1 | PA/FC |
|---|---|---|---|
| E146 | 10.06 | — | |
| S176 | 9.93 | — | |
| T177 | 8.28 | — | |
| R178 | 10.31 | Mt 32 | 1.13 |
| I179 | 10.03 | — | |
| D199 | 10.91 | — | |
| A200 | 10.90 | — | |
| C201 | 9.74 | — | |
| E202 | 10.06 | Mt 34 | 2.52 |
| W227 | 7.27 | — | |
| G228 | 3.82 | — | |
| G230 | 3.73 | — | |
| C231 | 6.69 | — | |
| D232 | 8.88 | — | |
| R233 | 7.94 | Mt 36b | 10.87 |
| D234 | 10.64 | Mt 36c | 2.18 |
| G235 | 10.41 | — | |
| K236 | 6.96 | — | |
| Y237 | 7.75 | — | |
| G238 | 7.88 | — | |
| F239 | 9.32 | — | |

One of the sites independently identified by this analysis is R233, which is demonstrated by the results reported in Table 1a to play a significant role in PCA specificity. Three other sites had been identified in the original screen reported in Table 1 and all three of them yielded a PA/FC ratio greater than 1, again confirming the instrumental role of this domain in segregating thrombin's substrate specificity towards aPC activity. Accordingly, it is within the scope of this invention to prepare NPs in which a residue has been inserted adjacent to, substituted for or deleted at any one or more of the residues scheduled in Table 1b. In particular, residues lying within 10 Angstroms of the E229 Cα or R233 Cα are of particular interest, and those that are within 8 Angstroms even more so. However, C201 and C231 are not preferred sites as they are paired to form a disulfide bond in native thrombin. G228, G230, G235 and G238 also are not preferred. Accordingly, preferred Table 1b residues for substitution, insertion or deletion are S176, T177, W227, D232, K236, Y237, and G239. Substitutions for the Table 1b residues are preferred over deletions or insertions, and are made with class members other than the one to which the native residue belongs, or the substitutions may be by other members of the native residue's class. In general, however, cysteine, proline and glycine will not be substituted in place of any of the Table 1b residues. The residues within 10 Angstroms of R233 will overlap many of the E229 proximal residues. Additional ones that do not overlap are readily identified using the three dimensional structure of Bode (op cit).

PCA polypeptides generally are polypeptides in which residues at one or more of the following thrombin sites have been substituted for the corresponding reference sequence residues: K52, K65, Y71, N74, W50, D58, H66, E202, E229, D234 and R233. The residues K52, K106, K107, K196 and/or K65 independently preferably are substituted with a naturally occurring amino acid residue, e.g., G, A, V, L, I, S, T, D, N, E, Q, C, M, F, Y, P, W, R or H. K52 ordinarily is substituted with cysteine, glycine, alanine, glutamic acid, aspartic acid, asparagine or glutamine, in some instances with any naturally occurring amino acid residue other than glutamic acid, or in other embodiments, with a residue other than glutamic acid or aspartic acid, while K65, K106, K107 and/or K196 typically are substituted with alanine, glutamic acid, aspartic acid, asparagine, glutamine, arginine or histidine.

Y71 is substituted preferably with a naturally occurring amino acid residue, e.g., G, A, V, L, I, S, T, D, E, Q, C, M, N, F, P, W, K, R or H, typically phenylalanine, threonine, serine, isoleucine, or tryptophan.

N74 is substituted preferably with a naturally occurring amino acid residue, e.g., G, A, V, L, I, S, T, D, E, Q, C, M, F, P, W, K, R, or H, typically alanine, glutamine, glutamic acid, or aspartic acid, W50 is substituted preferably with a naturally occurring amino acid residue, e.g., G, A, V, L, I, S, T, D, E, Q, C, M, F, P, N, K, R, Y, or H, typically cysteine, alanine, phenylalanine, lysine, arginine or histidine.

D58, D193 and/or D234 independently are substituted preferably with a naturally occurring amino acid residue, e.g., G, A, V, L, I, S, T, W, E, Q, C, M, F, P, N, K, R, Y, or H, typically alanine, glutamic acid, glutamine, asparagine, tyrosine, threonine or serine.

H66 is substituted preferably with a naturally occurring amino acid residue, e.g., G, A, V, L, I, S, T, W, D, Q, C, M, F, P, N, K, Y, E or R, typically alanine, lysine, asparagine, glutamine, threonine, histidine, or serine.

E202 and/or E229 independently are substituted preferably with a naturally occurring amino acid residue, e.g., G, A, V, L, I, S, T, W, D, Q, C, M, F, P, N, K, R, Y, or H, typically alanine, aspartic acid, phenylalanine, tryptophan, glutamine, asparagine, aspartic acid, tyrosine or serine.

R233 is substituted preferably with a naturally occurring amino acid residue, e.g., G, A, V, L, I, S, T, W, D, Q, C, M, F, P, N, K, E, Y, or H, typically alanine, lysine, asparagine, glutamine, glutamic acid, threonine, histidine or serine.

NPs representing combinations of the foregoing are within the scope of this invention. 2, 3, 4, 5, or more substitutions from the foregoing are introduced into thrombin as defined herein. The results of individual amino acid substitutions are generally additive except when the residues interact with each other directly or indirectly. We expect additional PCAs to be obtained from multiple substitutions at combinations of the 11 key residues described above (W50, K52, D58, K65, H66, Y71, N74, K106, K107, D193, K196, E202, E229, R233, D234). They are readily screened using the same procedures described below in order to identify those having improved properties, in particular an enhanced reduction in procoagulant activity relative to anticoagulant activity. They include for example E229,R233, D234; E229,R233; E229,D234; R233,D234; E229,K52; R233,K52; D234,K52; E229,R233,K52; E229,D234,K52; R233,D234,K52; E229,R233,D234,K52; W50,D58; W50, K52; W50,E229; W50,R233; W50,D234; W50,E229,R233, D234; W50,E229,R233; W50,E229,D234; W50,R233, D234; W50,E229,K52; W50,R233,K52; W50,D234,K52; W50,E229,R233,K52; W50,E229,D234,K52; W50,R233, D234,K52; W50,E229,R233,D234,K52; E202,E229,R233, D234; E202,E229,R233; E202,E229,D234; E202,R233, D234; E202,E229,K52; E202,E233,K52; E202,D234,K52;

E202,E229,R233,K52; E202,E229,D234,K52; E202,R233, D234,K52; E202,E229,R233,D234,K52; E202,W50,K52; E202,W50,E229; E202,W50,R233; E202,W50,D234; E202, W50,R233,D234; E202,W50,E229,R233; E202,W50,E229, D234; E202,W50,R233,D234; E202,W50,K52; E202,W50, E229; E202,W50,R233; E202,W50,D234; W50,E202; E202,K52; E202,E229; E202,R233; E202,D234; D58,K52; D58,E229; D58,R233; D58,D234; D58,W50; D58,E202; D58,K52,E229; D58,K52,R233; D58,K52,D234; D58,K52, W50; D58,K52,E202; D58,E229,R233; D58,E229,D234; D58,E229,W50; D58,E229,E202; D58,R233,D234; D58, R233,W50; D58,R233,E202; D58,D234,W50; D58,R233, E202; D58,W50,E202; D58,W50,R233; and D58,W50, D234.

Exemplary embodiments of multiple-substituted NPs fall within the following (the class of substitution is designated by the class number above, e.g. W50.3 means W50 substituted with any of V, L, I or M): W50.1,.2,.3,.5,.6,.7 or .8,K52.2,.3,.4,.5,.6,.7 or .8; W50.1,.2,.3,.5,.6,.7 or .8,D58.1, .3,.4,.5,.6,.7 or .8; W50.1,.2,.3,.5,.6,.7 or .8,H66.2,.3,.4,.5, .6,.7 or .8; W50.1,.2,.3,.5,.6,.7 or .8,Y71.1,.2,.3,.5,.6,.7 or .8; W50.1,.2,.3,.5,.6,.7 or .8,E229.1,.3,.4,.5,.6,.7 or .8; K52.2, .3,.4,.5,.6,.7 or .8,D58.1,.3,.4,.5,.6,.7 or .8; K52.2,.3,.4,.5,.6, .7 or .8,H66.2,.3,.4,.5,.6,.7 or .8; K52.2,.3,.4,.5,.6,.7 or .8,Y71.1,.2,.3,.5,.6,.7 or .8; K52.2,.3,.4,.5,.6,.7 or .8,R233.2, .3,.4,.5,.6,.7 or .8; D58.1,.3,.4,.5,.6,.7 or .8,H66.2,.3,.4,.5,.6, .7 or .8; D58.1,.3,.4,.5,.6,.7 or .8,Y71.1,.2,.3,.5,.6,.7 or .8; D58.1,.3,.4,.5,.6,.7 or .8,E202.1,.3,.4,.5,.6,.7 or .8; D58.1,.3, .4,.5,.6,.7 or .8,R33.2,.3,.4,.5,.6,.7 or .8; H66.2,.3,.4,.5,.6,.7 or .8,Y71.1,.2,.3,.5,.6,.7 or .8; H66.2,.3,.4,.5,.6,.7 or .8,E229.1,.3,.4,.5,.6,.7 or .8; H66.2,.3,.4,.5,.6,.7 or .8,R233.2,.3,.4,.5,.6,.7 or .8; Y71.1,.2,.3,.5,.6,.7 or .8,E229.1,.3,.4,.5,.6,.7 or .8; and Y71.1,.2,.3,.5,.6,.7 or .8,R233.2,.3,.4,.5,.6,.7 or .8.

Particular multiple-substituted NPs are W50F,Y or H,D58E,N or Q; W50F,Y or H,H66F,Y or W; W50F, Y or H,Y71F, H or W; W50F, Y or H,E229D, N or Q; W50F,Y or H,R233K or H; D58E, N or Q,H66F, Y or H; D58E, N or Q,Y71F, H or W; D58E, N or Q,E229D, N or Q; D58E, N or Q,R233K or H; H66F, Y or W,Y71F, H or W; H66F, Y or W,E229D, N or Q; H66F, Y or W,R233K or H; Y71F, H or W,E229D, N or Q; Y71F, H or W,R233K or H; E229D, N or Q,R233K or H; W50A,K52A; W50A,E229A; W50A, R233A; K52A,K106A,K107A; K52A,D193A,K196A; K52A,E202A; K52A,E229A; K52A,K233A; E229L, R233E; E229L,R233N; E229L,W50K; E229L,K52W; E229A,W50L; E229L,W50M; R233E,W50G; R233E, W50K; R233E,W50K; R233E, W50L; R233E,W50M; R233E,W50R; R233E,W50T; R233E,K52W; W50L,K52A; W50L,K52W; G230C,C231G; C231D,D232C; E202C, C201E; C201A,A200C; and E229A,R233A.

Further exemplary multiple-substituted NPs are selected from the following: K52G,E229G, A, V, I, L, S, T, D, N, C, Q, M, F, Y, P, W, R, K or H; K52A,E229G, A, V, I, L, S, T, D, N, C, Q, M, F, Y, P, W, R, K or H; K52V,E229G, A, V, I, L, S, T, D, N, C, Q, M, F, Y, P, W, R, K or H; K52L,E229G, A, V, I, L, S, T, D, N, C, Q, M, F, Y, P, W, R, K or H; K52I,E229G, A, V, I, L, S, T, D, N, C, Q, M, F, Y, P, W, R, K or H; K52S,E229G, A, V, I, L, S, T, D, N, C, Q, M, F, Y, P, W, R, K or H; K52T,E229G, A, V, I, L, S, T, D, N, C, Q, M, F, Y, P, W, R, K or H; K52D,E229G, A, V, I, L, S, T, D, N, C, Q, M, F, Y, P, W, R, K or H; K52N,E229G, A, V, I, L, S, T, D, N, C, Q, M, F, Y, P, W, R, K or H; K52E,E229G, A, V, I, L, S, T, D, N, C, Q, M, F, Y, P, W, R, K or H; K52Q,E229G, A, V, I, L, S, T, D, N, C, Q, M, F, Y, P, W, R, K or H; K52M,E229G, A, V, I, L, S, T, D, N, C, Q, M, F, Y, P, W, R, K or H; K52F,E229G, A, V, I, L, S, T, D, N, C, Q, M, F, Y, P, W, R, K or H; K52Y,E229G, A, V, I, L, S, T, D, N, C, Q, M, F, Y, P, W, R, K or H; K52P,E229G, A, V, I, L, S, T, D, N, C, Q, M, F, Y, P, W, R, K or H; K52W,E229G, A, V, I, L, S, T, D, N, C, Q, M, F, Y, P, W, R, K or H; K52R,E229G, A, V, I, L, S, T, D, N, C, Q, M, F, Y, P, W, R, K or H; K52H,E229G, A, V, I, L, S, T, D, N, C, Q, M, F, Y, P, W, R, K or H; W50G,E229G, A, V, I, L, S, T, D, N, Q, C, M, F, Y, P, W, R, K or H; W50A,E229G, A, V, I, L, S, T, D, N, Q, C, M, F, Y, P, W, R, K or H; W50V,E229G, A, V, I, L, S, T, D, N, Q, C, M, F, Y, P, W, R, K or H; W50L,E229G, A, V, I, L, S, T, D, N, Q, C, M, F, Y, P, W, R, K or H; W50I,E229G, A, V, I, L, S, T, D, N, Q, C, M, F, Y, P, W, R, K or H; W50S,E229G, A, V, I, L, S, T, D, N, Q, C, M, F, Y, P, W, R, K or H; W50T,E229G, A, V, I, L, S, T, D, N, Q, C, M, F, Y, P, W, R, K or H; W50D,E229G, A, V, I, L, S, T, D, N, Q, C, M, F, Y, P, W, R, K or H; W50N,E229G, A, V, I, L, S, T, D, N, Q, C, M, F, Y, P, W, R, K or H; W50E,E229G, A, V, I, L, S, T, D, N, Q, C, M, F, Y, P, W, R, K or H; W50Q,E229G, A, V, I, L, S, T, D, N, Q, C, M, F, Y, P, W, R, K or H; W50M,E229G, A, V, I, L, S, T, D, N, Q, C, M, F, Y, P, W, R, K or H; W50F,E229G, A, V, I, L, S, T, D, N, Q, C, M, F, Y, P, W, R, K or H; W50Y,E229G, A, V, I, L, S, T, D, N, Q, C, M, F, Y, P, W, R, K or H; W50P,E229G, A, V, I, L, S, T, D, N, Q, C, M, F, Y, P, W, R, K or H; W50K,E229G, A, V, I, L, S, T, D, N, Q, C, M, F, Y, P, W, R, K or H; W50R,E229G, A, V, I, L, S, T, D, N, Q, C, M, F, Y, P, W, R, K or H; W50H,E229G, A, V, I, L, S, T, D, N, Q, C, M, F, Y, P, W, R, K or H; W50G,R233G, A, V, I, L, S, T, W, D, Q, C, M, F, Y, P, N, K, E or H; W50A,R233G, A, V, I, L, S, T, W, D, Q, C, M, F, Y, P, N, K, E or H; W50V,R233G, A, V, I, L, S, T, W, D, Q, C, M, F, Y, P, N, K, E or H; W50L,R233G, A, V, I, L, S, T, W, D, Q, C, M, F, Y, P, N, K, E or H; W50I,R233G, A, V, I, L, S, T, W, D, Q, C, M, F, Y, P, N, K, E or H; W50S,R233G, A, V, I, L, S, T, W, D, Q, C, M, F, Y, P, N, K, E or H; W50T,R233G, A, V, I, L, S, T, W, D, Q, C, M, F, Y, P, N, K, E or H; W50D,R233G, A, V, I, L, S, T, W, D, Q, C, M, F, Y, P, N, K, E or H; W50N,R233G, A, V, I, L, S, T, W, D, Q, C, M, F, Y, P, N, K, E or H; W50E,R233G, A, V, I, L, S, T, W, D, Q, C, M, F, Y, P, N, K, E or H; W50Q,R233G, A, V, I, L, S, T, W, D, Q, C, M, F, Y, P, N, K, E or H; W50M,R233G, A, V, I, L, S, T, W, D, Q, C, M, F, Y, P, N, K, E or H; W50F,R233G, A, V, I, L, S, T, W, D, Q, C, M, F, Y, P, N, K, E or H; W50Y,R233G, A, V, I, L, S, T, W, D, Q, C, M, F, Y, P, N, K, E or H; W50P,R233G, A, V, I, L, S, T, W, D, Q, C, M, F, Y, P, N, K, E or H; W50K,R233G, A, V, I, L, S, T, W, D, Q, C, M, F, Y, P, N, K, E or H; W50R,R233G, A, V, I, L, S, T, W, D, Q, C, M, F, Y, P, N, K, E or H; W50H,R233G, A, V, I, L, S, T, W, D, Q, C, M, F, Y, P, N, K, E or H; E229G,R233G, A, V, I, L, S, T, W, D, Q, C, M, F, Y, P, N, K, E or H; E229A,R233G, A, V, I, L, S, T, W, D, Q, C, M, F, Y, P, N, K, E or H; E229V,R233G, A, V, I, L, S, T, W, D, Q, C, M, F, Y, P, N, K, E or H; E229L,R233G, A, V, I, L, S, T, W, D, Q, C, M, F, Y, P, N, K, E or H; E229I,R233G, A, V, I, L, S, T, W, D, Q, C, M, F, Y, P, N, K, E or H; E229S,R233G, A, V, I, L, S, T, W, D, Q, C, M, F, Y, P, N, K, E or H; E229T,R233G, A, V, I, L, S, T, W, D, Q, C, M, F, Y, P, N, K, E or H; E229D,R233G, A, V, I, L, S, T, W, D, Q, C, M, F, Y, P, N, K, E or H; E229N,R233G, A, V, I, L, S, T, W, D, Q, C, M, F, Y, P, N, K, E or H; E229Q,R233G, A, V, I, L, S, T, W, D, Q, C, M, F, Y, P, N, K, E or H; E229M,R233G, A, V, I, L, S, T, W, D, Q, C, M, F, Y, P, N, K, E or H; E229F,R233G, A, V, I, L, S, T, W, D, Q, C, M, F, Y, P, N, K, E or H; E229Y,R233G, A, V, I, L, S, T, W, D, Q, C, M, F, Y, P, N, K, E or H; E229P,R233G, A, V, I, L, S, T, W, D, Q, C, M, F, Y, P, N, K, E or H; E229K,R233G, A, V, I, L, S, T, W, D, Q, C, M, F, Y, P, N, K, E or H; E229R,R233G, A, V, I, L, S, T, W, D, Q, C, M, F, Y, P, N, K, E or H; E229H,R233G, A, V, I, L, S, T, W, D, Q, C, M, F, Y, P, N, K, E or H; and E229W,R233G, A, V, I, L, S, T, W, D, Q, C, M, F, Y, P, N, K, E or H.

Included within the scope of this invention are NPs having one or more amino acids inserted immediately adjacent to a thrombin amino acid at any of the designated Table 1, 1a or 1b positions in the reference sequence. Insertional NPs generally will have a polypeptide structure comprising the sequence $NH_2$—PP—A—$(X)_{n1}$—B—PP—COOH, wherein X is the inserted residue(s) (which may be the same or different), n1 is an integer, either A or B are the designated residue sites for insertion and PP represents the remainder of the NP or a bond at the N or C terminus of the NP. Examples include K52AA, R233RA, K52KA, K52AK, E229AE, E229EW, E229WE, E229EY, E229YE, G228GE, G228GA, G228GS, G228GAA, G228GAE, G228GSE, G230GA, G230GS, G230GAA, and E229EA (reading in the N to C terminal direction). Insertions typically are found within about 10 Angstroms of E229 and adjacent to any Table 1b residue. Insertions include thrombin or non-thrombin polypeptides ranging from 1 to about 1000 or more residues, although these are typically introduced at the N or C-terminal ends of the NP A and/or B chains. These polypeptides include prothrombin sequences or fragments thereof (whether from humans or animals), antigenic sequences for immunoaffinity purification of the NP products from cell culture, signal sequences and the like as are more fully described below.

Also included within the scope of this invention are NPs in which a glycosylation site is introduced or removed from the reference sequence, whether by substitution, insertion or deletion of one or more amino acid residues. Such changes will result in the installation or removal of the sequence NXS or NXT, where X can be any residue. Thus, asparagine can be substituted for any residue located 2 residues N-terminal to serine or threonine to introduce a glycosylation site. Alternatively, the single glycosylation site of wild-type thrombin at N53 can be omitted by substituting N53 with any residue, deleting F54, substituting any residue other than serine for T55 or inserting at least one residue between N53 and T55.

Also included within the scope of this invention are deletional NPs, i.e., NPs in which one or more amino acid residues of the reference sequence have been removed at a designated site, whereby flanking residues are now joined by a peptide bond in the ordinary fashion. Any of the sites set forth in Tables 1 or 1b are suitable for deletion, although it generally is not preferred to delete P, C or G residues. In addition, the thrombin A chain in its entirety optionally is deleted in some NP embodiments. In embodiments of this invention, deletions are made within about 10 Angstroms of E229 and include any of the residues in Table 1b, preferably A200, E202, Y237, I179, R178, E146, as well as S226.

Typically, deletions or insertions are relatively small, on the order of 1 to 10 residues and generally no more than 2, although deletions or insertions can be quite large if they are not in portions of the reference sequence required for procoagulant or anticoagulant activity as the case may be, or the additional sequence is to be removed at some point during post-translational or post-recovery processing. The number of residues that are deleted or inserted in part will depend upon whether or not they are found in secondary structural components such as helices or sheets (whereupon only 1 or, preferably 2 residues are inserted or deleted), or are in less structurally confined domains such as loops, where larger numbers of residues may be deleted or inserted without unduly perturbing the structure of thrombin.

Also included within the scope of this invention are NPs having combinations of deletions, insertions and/or substitutions. Typically, a deletion of a single residue will be accompanied by an insertion within 1 to about 3 residues of the deletion site; deletions of larger domains not necessary for procoagulant or aPC activity, as the case may be, need not be accompanied by an insertion. The thrombin A chain optionally is deleted from NPs, in which case the B chain cysteine residue that ordinarily forms a disulfide bond with the A chain (C119) is substituted or deleted from the B chain. Typical substitutions at C119 would be any of R, G, A, V, I, L, S, T, W, D, Q, M, F, Y, P, N, K, E or H, but ordinarily would be S, M or A. Most insertions employed for purposes of facilitating the expression or recovery of NPs will naturally be accompanied by other modifications in the reference sequence that confer the desired properties on the NPs, e.g. as to anticoagulant or procoagulant effect.

The NPs of this invention may be subject to post-translational covalent modification, e.g. deamidation of asparagine or glutamine, or oxidation of cysteine residues, and absent or variant glycosylation at N53 depending upon the host cell used to express the variant. NPs containing such modifications are included within the scope of this invention. If N53 is glycosylated, it preferably is glycosylated with carbohydrates characteristic of mammalian cells, although it also may bear fungal (such as yeast) glycosylation patterns. Glycosylation characteristic of expression of the NP from fibroblast, kidney, lung, skin, neural, liver or bone marrow cells or cell lines, or of any mammalian cell line such as CHO or embryonic kidney cells, is acceptable.

One major mechanism of thrombin clearance in vivo is the formation of a thrombin-AT-III complex, which is largely dependent on cell surface heparin-like molecules. We expect that mutating thrombin's heparin-binding site will prevent heparin binding and thereby prolong the plasma half-life of the protein. Clinically, this will reduce the amount of protein required to achieve an anti-thrombotic effect. In this embodiment the heparin binding site is mutagenized so that the NP no longer is capable of substantially binding to heparin. This is accomplished by deletion, substitution or insertion of one or more residues in at least the known heparin binding domain (including R89, R180, R245, K248 and K252). Resistant NPs include substitutions or insertions that result in the introduction of a novel O- or N-linked glycosylation site (NXS/T) into the binding region (for example R180N).

Table 1 shows that two mutants, each involving triple alanine substitutions, were resistant to heparin-mediated inhibition by AT-III, exhibiting greater than 50% of fibrinogen clotting activity in the presence of heparin compared to 18% for wild-type thrombin. One of these mutants, involving the simultaneous substitution of R178, R180 and D183, displayed no reduction in procoagulant or anticoagulant activity. Optimal mutants are identified by screening for those that are most resistant to heparin-mediated inhibition, particularly in the presence of antithrombin III. Mutations of this type optionally are combined with variations described above, e.g., those that display a reduction in procoagulant activity relative to anticoagulant activity. Such NPs are administered in combination with heparin to achieve a potent anticoagulant effect where the anticoagulant pathway is activated by the NP and the procoagulant activity of the endogenous thrombin is inhibited by heparin-mediated inhibition by AT-III.

Preparation and Selection of NPs

Optimal NPs which exhibit modulate fibrinogen clotting or aPC, reduced heparin inhibition, modified ability to cleave the platelet thrombin receptor, and other desired properties, are identified by screening candidates against the relevant in vitro assays as described herein, then testing in animals as desired followed by determination of efficacy in thrombosis or bleeding models. Exogenous aPC may be used as a positive control. The selected NPs optionally then are directly tested in animal models in which aPC infusion has been shown to be efficacious, e.g. in rabbit, guinea pig, or baboon septic shock or arterial thrombosis models. Additionally, the anticoagulant potency of such NPs can be tested in cardiopulmonary bypass models. These assays are conventional and widely known in the art. It would not require undue experimentation to make and test other NPs than those specifically disclosed herein.

The NPs of this invention are readily prepared by methods known in the art. In general, nucleic acid encoding the NP is prepared by PCR, in vitro synthesis, cloning or combinations of the three, including if necessary the site directed mutagenesis of thrombin-encoding nucleic acid. It is expressed in in vitro systems or in recombinant host cells. One method for expression is ribosome based synthesis using dedicated tRNAs (Benner, "TIBTECH" 12:158–163 [1994] and Robertson et al., "J. Am. Chem. Soc." 113: 2722–2729 [1991]), but ordinarily, the NP-encoding nucleic acid (generally DNA) is inserted into an appropriate expression vector, host cells are transfected with the recombinant vector, the recombinant host cells are grown in suitable culture medium, and the desired amino acid sequence NP is recovered from the recombinant cell culture by chromatographic or other purification methods. It is also within the scope of this invention to partially synthesize the NP in recombinant cell culture or by in vitro methods and then ligate the polypeptide fragments by peptide ligase (reverse proteolytic synthesis).

The nucleic acid for expression of the NP typically encodes a preprothrombin containing the desired mutation since this permits facile expression and processing by methods heretofore used with thrombin. In addition, known methods for the recombinant expression of "gla-domainless" prothrombin are readily adapted to the preparation of the NPs of this invention. It is within the scope of this invention to express nucleic acid that encodes NP analogues of any of (a) prethrombin-2 (alpha thrombin) or prethrombin-1, (b) the sequence of both chains of meizothrombin des 1 (which are either expressed as a single chain extending from S156 [Degen et al.] to the 3' end of the nucleic acid encoding the B-chain, or are coexpressed as nucleic acids separately encoding the S156 fragment and the thrombin B chain), (c) thrombin (which is expressed as a single chain encoding both of the A and B chains, or is coexpressed in the same cell as nucleic acids separately encoding the A and B chains) or (d) the thrombin B chain free of the A chain. By "separately encoding" is meant that the A and B chain-encoding nucleic acids are separated by at least a stop codon and, if necessary, the downstream nucleic acid (usually B chain) commences with a start codon. Note, however, that bacterial polycistronic expression cassettes may not require a start codon for the downstream coding sequence. Suitable vectors and host cells for expression of the two chains independently are described in U.S. Pat. No. 4,923,805. Such heterodimeric expression systems generally are mammalian.

Polycistronic expression systems are useful for single cell coexpression of sequences comprising the two thrombin chains described above. These systems are known per se, and are particularly useful where, as here, it is desired to make the NP A and B chains independently in the cell culture and thereby avoid any need for post-translational processing. In this instance both chains generally are expressed under the direction of the same expression control sequence (which chains and expression control sequences can be on the same or a different vector). However, the nucleic acid encoding each chain contains its own start codon as required and, preferably, each nucleic acid encodes its own signal sequence.

The NP optionally is expressed as a preprotein of α-thrombin or the A or B chains separately, whereby the NP is expressed as a precursor that is processed to the mature NP and secreted from the host cell. The presequences or signal sequences for use herein include the native presequence normally associated with the source of the thrombin gene, e.g. the human presequence for preprothrombin, or presequences that have amino acid sequences that are heterologous by sequence or origin to the prothrombin signal. Suitable presequences include those of (a) microbial proteases such as subtilisin, (b) mammalian proteases such as trypsin, chymotrypsin, fibrinolytic enzymes including urokinase or tPA, and blood clotting factors such as Factors V, X, IX, VII, VIII or fibrinogen, (c) cytokines such as gamma interferon or an interleukin, (d) growth factors such as growth hormone or TGF-alpha, (e) polypeptides or proteins having N-terminal mature sequences that are homologous to human thrombin A or B chains, (f) immunoglobulins, (g) receptors, (h) other presequences of secreted or cell membrane bound proteins or (i) known presequences used to direct the secretion of gla domainless prothrombin (pages 11, line 30—page 12, line 21 of WO 93/13208). Signal sequences optionally are derived from or are homologous to the host cell, or at least the phylogenetic branch to which the host cell belongs. For example, one ordinarily would use a presequence of a yeast protein, such as mating factor, in a yeast expression system, or of a bacterium, such as ST-II or beta-lactamase, in bacterial cell culture systems. It would be desirable to select signals from heterologous polypeptides that have mature N-terminal residue(s) that are the same as the mature thrombin A or B chains, and to use those signals with the N-terminally-homologous thrombin chain. A wide variety of suitable signal sequences are known and can be used in methods for the preparation of the NPs described herein.

The nucleic acid constructs encoding the secreted NP generally will encode the thrombin A or B chains fused at their N-termini to the normal C-terminus of the same or different signal sequences. They are spliced into expression vectors under the control of expression control sequences such as promoters, operators, enhancers and polyadenylation sequences as is generally known in the art. Constructing suitable expression vectors for secreted or protoplasmically expressed NPs of this invention is a matter of routine for those skilled in the art, and will be accomplished using the conventional tools of molecular biology, including nucleic acid synthesis in vitro, PCR, adapters, ligases, restriction enzymes, expression and shuttle plasmids, transfection aids and the like, all of which are publicly (and for the most part commercially) available.

Suitable promoters or enhancers, termination sequences and other functionalities for use in the expression of NP in given recombinant host cells are well known, as are suitable host cells for transfection with nucleic acid encoding the desired NP, some of which are mentioned above while others are described in WO 93/13208 at page 12, line 21—page 19, line 5, and EP 319,312 B1, page 16, lines 10–18 and Table II thereof. It may be optimal to use host cells that are capable of glycosylating the NPs, which typically include mammalian cells such as embryonic kidney 293 cells, COS cells, CHO, BHK-21 cells and the like. In addition, host cells are suitable that have been used heretofore to express proteolytic enzymes or zymogens in recombinant cell culture, or which are known to already express high levels of such enzymes or zymogens in non-recombinant culture. In the latter case, if the endogenous enzyme or zymogen is difficult to separate from the NP then the endogenous gene should be removed by homologous recombination or its expression suppressed by cotransfecting the host cell with nucleic acid encoding an anti-sense sequence that is complementary to the RNA encoding the undesired polypeptide. In this case the expression control sequences (e.g., promoter, enhancers, etc.) used by the endogenous highly expressed gene optimally are used to control the expression of the NP.

The host-vector system should be selected so as to yield substantially homogeneous NP, thereby avoiding the need to purify a single molecular species from other isoforms of the NP. Thus, if the cell is capable of glycosylation, essentially all of the NP molecules should be glycosylated. In addition, host cells optimally will be selected that are devoid (in the relevant cell compartment) of proteolytic activity that is capable of intrachain cleavage of the thrombin A or B chains. Cells can be selected that contain no protease, e.g., in the periplasm, that will cleave after thrombin B R62, R123, R73, or K154, all of which are known to be sites of B chain degradation. For example, *E. coli* and other microbial strains are known that possess little or no extracellular or periplasmic proteolytic activity (other than signal peptidases). Such cells optimally would be used in expression systems in which the A and B chains are expressed in the same host cell fused to the same or different signal sequences. The A and B chains are co-secreted into the periplasm or extracellular medium where they become disulfide bonded. The absence of deleterious proteases helps to ensure that the product is not rendered microheterogenous as to chain length by host-endogenous proteases acting on the product NP, but of course independent A and B chain secretion is not dependent upon the use of such cells. In addition, or alternatively, the basic residues of the A or B chains that are sites for proteolytic cleavage are substituted with residues other than K or R. For example, K154 has been reported to be one of the sites cleaved in the conversion of gamma thrombin (Colman et al., "Hemostasis and Thrombosis", p. 154 (1987)). Table 1 above shows that K154 can be substituted with A without significant change in activity. Thus, K154 can be substituted with another residue other than R in order to confer resistance to proteolytic degradation (in addition to whatever other variations are desired). This also may extend the in vivo life of the NP.

The recombinant cells are cultured under conventional conditions and using conventional culture media heretofore employed with the cells in question. These conditions and media are widely known. Freshly transfected cells may only transiently express the NPs, but stable transformants readily are obtained in accord with conventional practice using cotransformation with a selection gene such as DHFR or glutamine synthetase and serial culture in the presence of a selection agent such as methotrexate or methionine sulfoximine, respectively. Yields of NPs can differ substantially despite minor differences in the character of substituents or insertions. In such cases, it is desirable to screen for an expression system that will yield a quantity of thrombin that is at least about 75% of that obtained with the reference thrombin in the same expression system. It occasionally is useful to culture the cells at lower than the usual 37° C., typically about from 10° C. to 30® C., optimally about from 15° C. to 27° C. This is the case with either microbial or mammalian cells.

The NP preferably is expressed as a properly assembled, disulfide bonded thrombin A and B chain analogue, or as the B chain analogue alone. In general, the NP will be water soluble. It may be expressed in bacteria in the form of refractile bodies, in which case the insoluble NP is recovered and refolded using known methods, e.g. dissolution in guanidinium hydrochloride followed by gradual removal of the denaturant. Directly expressed NPs of this invention may have an extra N-terminal methionine or blocked methionine residue, although host cells can be employed that will cleave away such extraneous N-terminal methionine residues.

If the A and B chains are fused, for example when the NP is expressed as the α-thrombin analogue, then post-translational proteolytic processing may be required in order to activate the precusor zymogen to the proteolytically active NP. Such precursors are analogous to naturally occurring prothrombins or may be fusions of one or both NP chains with a thrombin-heterologous polypeptide, as in the case of signal sequences. Proteolytic activation and/or processing is accomplished in the host cell culture itself, or can be done after recovery of the NP precursor (with or without intervening purification of the NP precursor). Post-translational proteolytic processing (either within the host cell culture or after initial recovery of the NP precursor) is used to remove any prothrombin (or prothrombin-heterologous) sequences that may be fused N-terminal to the A or B chain NPs, or that is inserted elsewhere within an NP precursor (e.g., antigen tags used to facilitate purification). The NP precursors are hydrolyzed by an enzyme or enzymes that is capable of making the correct cleavages without excessive or undesirable hydrolysis within the NP A or B chains. A generally suitable enzyme for removing pro sequence and activating native prothrombin is found in Echis carinatus (saw-scaled viper) venom. Factor Xa also is useful to activate NP precursors. Proteolytic activation is not required by NP mature B chain or coexpressed individual mature A and B chains.

Proteolytic activation of NP precursor is facilitated by substitution of the thrombin activation domain (the Factor Xa cleavage site) with another sequence recognized and cleaved by a different protease or by thrombin itself. Suitable substituted activation sites for use with the NPs of this invention are described in WO93/13208, page 9, line 21—page 10, line 17. As noted in WO93/13208, substitution of the thrombin activation site in prothrombin with the yeast KEX2 site is attractive because yeast can express KEX2 and therefore endogenously cleave thrombin precursors at the activation site. Other sequences that are suitably substituted for the thrombin activation domain are disclosed in Table 1 of EP 319,312 B1. These are cleaved by cell membrane-associated proteases as part of cell culture processing of NPs or their precursors.

Proteolytic activation can be accomplished at any point in the expression or purification of NP or its precursors, but typically is done after purification of NP precursors from the cells and/or cell culture supernatant. It will be noted that NPs containing a new dibasic site resulting from an insertion or substitution of an R or K residue into the thrombin sequence may be susceptible to hydrolysis by enzymes that otherwise would not cleave native thrombin, thereby reducing yields somewhat during expression or activation. In this case, it may be desirable to select an expression system and/or an activating enzyme having different substrate specificity so as to reduce adventitious cleavage.

The yields of NP from recombinant host cell culture will vary, depending upon a number of factors including the culture conditions and the nature of the NP. Optimally, the yield of NP by weight from the culture should be greater than about half (and preferably greater than 75%) that of reference thrombin.

It is possible to diagnostically use the NP-containing, activated, concentrated conditioned medium of the recombinant cells without further purification. However, NPs intended for therapeutic use should be isolated or purified by methods heretofore employed for thrombin or other proteins, e.g., native or reducing/SDS electrophoresis, isoelectric focusing, immobilized pH gradient electrophoresis, salt precipitation, solvent fractionation (using ethanol for example) and chromatography such as gel filtration, ion exchange (cation or anion), ligand affinity (cibacron blue F3GA or p-aminobenzamidine), immunoaffinity, chromatofocusing, reverse phase or hydrophobic interaction chromatography. Suitable methods are disclosed in Colman et al., "Hemostasis and Thrombosis", p. 148 (1987) and references cited therein, in WO 93/13208 page 19, line 33—page 21, line 25, and other conventional sources. The activating enzyme (if any) can be immobilized or is removed in subsequent purification steps. Typically, the NP will be isolated so as to be >95% pure by weight of protein, and preferably greater than 99% pure.

The NPs or their fragments also are prepared in vitro, especially if they are relatively small, e.g. on the order of about 30 residues or less. However, larger and intact NPs also are prepared by in vitro processes. For example, smaller NPs are prepared by synthesis using standard solid-phase peptide synthesis procedures as described by Merrifield "J. Am. Chem. Soc." 85:2149 (1963). These then are ligated together by the use of peptide ligase (reverse proteolysis). In vitro methods of protein synthesis also are used to prepare NPs without the need for recombinant cell culture. Such methods are useful for small-scale preparations, and have the advantage of reducing the possible effect on yields of host cell proteases. In vitro NP protein synthesis has one additional quite substantial advantage in that it permits the site-specific introduction into the NP of a non-naturally occurring amino acid residue (Benner, and Robertson et al., cited above). Accordingly, when the term "amino acid residue" is used herein (in connection with thrombin modification by substitution or insertion, especially by a single amino acid) it will be understood that the amino acid is not limited to the naturally occurring residues associated with native tRNAs. As noted by Robertson et al., aminoacyl tRNA is efficiently prepared using a variety of non-naturally occurring amino acid residues ("non-naturally occurring" means not naturally found in proteins, although the amino acid might be found in biological systems in nature). Since the tRNA is selected to be incorporated at a codon not recognized by any of the common tRNAs involved in protein synthesis, the selected non-naturally occurring amino acid residue is incorporated only at the particular site in the NP sequence chosen for the unique codon. Thus, in these cases the NP is encoded by a nucleic acid having a nonsense codon, e.g., UAG, at the desired unique insertion or substitution site. The non-naturally occurring amino acids that are suitably incorporated are described for example in Greenstein et al., "Chemistry of the Amino Acids" Vols. 1–3, 1986. In general, one will use pharmaceutically innocuous L-amino acids that are found in nature but ordinarily not incorporated into proteins. Such amino acids typically will be structurally related to a naturally occurring residue that produces the desired effect at a given site and will be used to further resolve and optimize the desired property of the NP.

The NPs of this invention also include thrombins that have been substituted by a non-peptidyl moiety, either for purposes of preparing the NP to begin with or as a subsequent modification of the NP prepared by amino acid substitution, insertion or deletion as described elsewhere herein. NPs per se are prepared by covalent modification of thrombin or its component chains or subfragments. Since we have determined a number of the key residues involved in the procoagulant and anticoagulant function of thrombin it is within the scope of this invention to introduce a covalent modification at such sites that accomplishes essentially the same objective as the corresponding site-directed mutant with a naturally occurring residue. For example, carboxyl-containing side chains of residues such as E229 are derivatized by reaction with carbodiimides (R'—N=C=N—R' where R and R' are different alkyl groups), or are amidated by reaction with ammonia or substituted amines.

Basic side chains such as those of R233 and K52 also are derivatized. For example, R233D and E are very good PCAs in which a positively charged side chain has been substituted with a negatively charged side chain. Similar charge reversals are accomplished by substituting a thrombin R233 or K52 with chloroacetic acid. Lysine residues are acetylated with acetic anhydride.

Tryptophan is a relatively rare amino acid in thrombin. Accordingly, W50 is an attractive site for post-translational covalent modification because substitution at other sites is expected to be less than may be the case with more common residues. Reaction of W50 with an oxidant such as a halogen donor, e.g. bromine, will yield the side chain structure

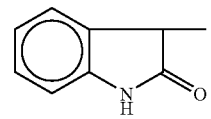

This reaction should be conducted in aqueous solvent and at low halogen concentrations.

Other covalent modifications of NPs, or of thrombin to obtain the NPs of this invention, will be apparent to the artisan. Side chains where reaction is undesired are protected by masking them with antibodies directed against an epitope that includes the residue to be protected. Reagents for accomplishing such modifications are well-known and have been widely used in the diagnostic and preparative fields. See T. Creighton, *Proteins: Structure and Molecular Properties*, 1983.

Covalent modifications also are useful to accomplish objectives other than the preparation of NPs having segregated substrate specificity. For example, NPs are rendered insoluble by cross-linking them to a water insoluble matrix. This is accomplished by reacting the NP and matrix with a bifunctional agent that forms the covalent crosslink. Examples of suitable agents are 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, NP is immobilized on reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440.

NPs also are covalently modified by linking the NP to various nonproteinaceous polymers, e.g., polyethylene glycol, polypropylene glycol or polyoxyalkylenes, in the manner set forth for example in U.S. Pat. Nos. 4,640,835; 4,496,689; 4,301,144; 4,670,417; 4,791,192 or 4,179,337.

The in vivo circulating half-life of NP is lengthened by conjugating the NP to a polymer that confers extended half-life, such as polyethylene glycol (PEG). PEG is a non-immunogenic, linear, uncharged polymer with three water molecules per ethylene oxide unit. (Maxfield, et al., "Polymer" 16:505–509 (1975); Bailey, F. E. et al., in "Non-ionic Surfactants", Schick, M. J., ed, pp. 794–821 (1967)). Several therapeutic enzymes have been conjugated to PEG to increase their in vivo half-life (Abuchowski, A. et al., "J. Biol. Chem." 252:3582–3586 (1977); Abuchowski, A. et al., "Cancer Biochem. Biophys." 7:175–186 (1984). An IL-2 (interleukin-2)-PEG conjugate has been reported to increase circulatory life and potency (Katre, N. V. et al., "Proc. Natl. Acad. Sci." 84:1487–1491 (1987); Goodson, R. et al., "Bio/Technology" 8:343–346 (1990)). See also Abuchowski, A. et al., "J. Biol. Chem." 252:3578–3581 (1977). Any of the methods for PEG conjugation used in these citations is acceptable for use with the NPs of this invention.

Finally, NPs are covalently modified for use in diagnostic applications by cross-linking them to detectable groups heretofore employed in diagnostic assays as is more fully described below.

Uses for the NPs of this Invention

The NPs of this invention are useful in therapeutic, diagnostic and preparatory methods. Their use will depend upon the properties that they possess, as will be apparent to the ordinary artisan. For the most part, all of the NPs will retain immune epitopes of thrombin, so they are useful in place of thrombin in immunoassays for thrombin, whether or not they fall within the definition of PCA or FCP used herein and whether or not they possess any proteolytic activity. In addition, PCAs and FCPs have specialized therapeutic uses.

Anticoagulant NPs, in particular PCAs, are useful to ameliorate or prevent undesired clotting. They are effective in activating the endogenous protein C pathway, serving as a potent anticoagulant by generating endogenous aPC to inactivate FVa and FVIIIa, and enhancing tPA mediated fibrinolysis by inactivating PAI-1. The clinical indications for such NPs, and particularly PCAs, include thrombotic diseases or conditions such as septic shock, adjunctive therapy in coronary thrombolysis and angioplasty, pulmonary embolism, transient ischemic attacks and strokes, unstable angina, M.I., deep venous thrombosis and a variety of arterial and venous thromboses. In a method for treating septic shock the anticoagulant NP is administered to patients in advanced sepsis (gram negative, gram positive or fungal), e.g. who exhibit symptoms of high fever, hypotension, disseminated intravascular coagulation, renal insufficiency and/or ARDS. Anticoagulant NPs especially PCAs are useful for any of the utilities heretofore proposed for aPC. In this regard, see EP 191 606 B1, page 13, line 52, page 15, line 32. Thus, for therapeutic applications, anticoagulant NPs and especially PCAs are administered to a mammal, preferably a human, in a pharmaceutically acceptable dosage form and in a therapeutically effective dosage. The anticoagulant NP is administered intravenously as a bolus or by continuous infusion over a period of time, or by intramuscular, subcutaneous, intra-articular, intrasynovial, intrathecal, topical, or inhalation routes. The anticoagulant NPs also are suitably administered by catheter to exert primarily local anticoagulation.

Anticoagulant NPs also are useful in the diagnosis of clotting disorders. A substantial portion of hypercoagulation states found in patients cannot be ascribed to a particular molecular defect. Many patients prone to bouts of thrombosis may suffer from an inborn error in a component of the protein C activation pathway, but it is presently difficult to diagnose such patients. PCA especially are useful to provide a diagnosis of a defective activated protein C pathway and the component of the pathway that is deficient. In this embodiment the subject does not need to be in immediate need of anticoagulant therapy but may be known to have been subject to excessive thrombosis of unknown origin. Anticoagulant NP such as PCA is administered to the patient and the anticoagulant state of the patient's blood is determined after the PCA has had time to act. The dose of PCA is substantially the same as the amount of PCA effective in normal patients in inducing detectable anticoagulation. The anticoagulation state of the subject is measured at substantially the same time points as those at which detectable anticoagulation is induced in normal patients. Any assay for blood clotting is suitable, e.g. aPTT and the like. If the PCA is not successful in detectably anticoagulating the subject's blood it is likely that the patient suffers from a defect in the thrombomodulin-protein C anticoagulation pathway. In a further embodiment, administering soluble TM together with PCA and determining whether either protein resolves the defect will yield information on the location of the deficiency, i.e., if TM and the NP induce anticoagulation, but protein C and the NP do not, one can conclude that the subject's TM is responsible for the defect.

Procoagulant NPs are useful therapeutically as procoagulants for any purpose. For example, they are impregnated into dressings, bandages and the like, or otherwise included in dosage forms intended for topical administration. FCP also are effective as thrombosis accelerants in the thrombotic treatment of large solid tumors. The FCP are used in place of C4b binding protein, or anti-aPC antibodies as described in U.S. Pat. No. 5,147,638, optimally in combination with a cytokine such as TNF-α or TNF-β, gamma interferon, IL-1, IL-2 and/or GM-CSF. The dose of FCP will be titered to induce clotting in tumors, but not produce clinically significant clotting elsewhere. Proforms of NPs which are dependent upon endogenous activation also can be used in this method.

Dosage forms of the NPs of this invention are those conventionally used with other protein therapeutics. The NPS will be sterile, typically will be disposed into containers suitable for sterile access (vials, for example, sealed with elastomeric stoppers), and encompass pharmaceutically acceptable carriers that are nontoxic, including salts and solvates. Examples of such carriers include ion exchangers, alumina, aluminum stearate, lecithin, serum proteins such as human serum albumin, buffers such as phosphates, glycine, arginine, lysine, sorbic acid, potassium sorbate, partial glyceride mixtures of saturated vegetable fatty acids, water, alkali metal salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of the NPs include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms may be used and include, for example, microcapsules, nano-capsules, liposomes, plasters, inhalation forms, nose sprays, and sublingual tablets. The NP typically will be formulated in such vehicles at a concentration of about 1–150 micromolar or 1–200 mg/mL. It will be desirable to include an antioxidant such as ascorbate, particularly if, as will generally be the case, the NP includes a disulfide bond joining the A and B chains or a disulfide bond found within the B chain. The pH of the formulation should be selected to minimize deamidation and autolysis, and generally will be about from 5 to 8. The formulations preferably will be lyophilized, but can be prepared and stored as aqueous solutions.

The appropriate dosage of anticoagulant NP for the prevention or treatment of thrombosis will depend on the amount of residual procoagulant activity (if any), location and nature of the thrombosis or expected thrombosis to be treated, the severity and course of the clotting disorder, whether the anticoagulant NP is administered for prophylaxis or therapy, the nature and course of previous treatment, the half-life of the NP in the circulation, the use of other therapeutics or anticoagulants, the locality of NP administration (local doses will be lower than systemic doses), the patient's response to the NP, whether the NP requires activation by endogenous prothrombin activation pathways (i.e., whether the thrombin NP is supplied as the corresponding prothrombin or unactivated fragment thereof) and other considerations within the discretion of the attending physician. Since PCA is an active enzyme, the amount required for anti-thrombotic effect is quite small, in the 5–10 nM range (final concentration in plasma), and in fact our studies in rabbits show that the K52A PCA produces therapeutic anticoagulation at plasma levels ranging from about 3–9 nM, with similar results for E229A PCA. This compares quite favorably with other anticoagulant macromolecules such as hirudin (100–800 nM) or GS-522, a thrombin-binding DNA aptamer (2000–4000 nM; PCT US 92/01367). Our preliminary monkey studies suggest that the dose of PCA in primates will range about from 0.05 U/kg/min to 20 U/kg/min, depending primarily on the amount of residual fibrinogen cleavage activity (which will militate in favor of lower doses to prevent fibrinogen consumption and platelet activation) and the potency of the aPC activity (PCA that retain a substantial proportion of wild-type aPC activity will be used in the lower dose range). 1 U is equal to the amount of S-2238 amidolytic activity in 1 NIH Unit (clotting activity) of wild-type thrombin (cf Example 4).

The NPs of this invention are not expected to be immunogenic since in preferred embodiments only a few critical residues are modified (less than about 5), or are masked with glycosylation. This is particularly the case with single substitutions (e.g. E229D) that are highly conservative. The half-life of certain NPs may be very short, requiring them to be used as a continuous infusion (the plasma half-life of wild type thrombin in vivo is probably extremely short, in the range of seconds). This, however, may be clinically advantageous in some circumstances since it would dispense with the need for a thrombin inhibitor should a bleeding episode develop in the patient. PCAs have an anticoagulant effect in subhuman primates and other animals for about from 90 to 180 minutes following administration at adequate doses, so it is feasible to administer PCAs by a single injection or a brief (e.g., 10 minutes) infusion. However, administration by continuous infusion is also within the scope of this invention.

Procoagulant or anticoagulant NPs suitably are administered to the patient at one time or over a series of treatments. For repeated administrations over several days or longer, depending on the condition, the treatment is continued until the desired anticoagulant or procoagulant effect is achieved.

According to another embodiment of the invention, the effectiveness of the compounds of this invention as procoagulants or anticoagulants is improved by administering the compounds serially or simultaneously with another agent or medical procedure that is effective for the relevant purposes. PCA is useful in conjunction with known anticoagulants such as heparin, Factor X inhibitors, platelet aggregation inhibitors, and the like. It also is useful in conjunction with thrombolytic therapies using for example tPA, urokinase or streptokinase, or with balloon angioplasty or other procedures that entail the lysis of clots, treatment of atherosclerotic plaques or manipulation of or contact with the vascular endothelium.

The NPs of this invention are useful in identifying substances that bind to target sites on thrombin (thrombin binding partners, or "TBP"). Of particular interest are substances that bind to the PC activating domain of thrombin but not to the procoagulant domain, or vice-versa. In preferred embodiments they are capable of binding to thrombin and substantially inhibit the procoagulant activity of thrombin without comparatively inhibiting its PC activating function. This does not mean that the TBP need leave the thrombin PC activating function entirely uninhibited. All that is necessary in this instance is that the degree of inhibition of PC activation be less than that of the procoagulant function. Typically, the TBP will inhibit the target thrombin proteolytic activity such that the ratio of PC activation to procoagulant activity is less than about 0.5 or greater than about 2.0. TBPs in general are polymers falling into two classes: polypeptides and oligonucleotides, but are essentially unlimited and can include any substance, including molecules of less than about 1500 molecular weight. TBPs are used in diagnostic procedures, to indirectly label thrombin or to separate thrombin from other substances present in test samples. TBP's ability to bind to thrombin also is useful in methods for recovering thrombin from contaminated mixtures such as cell culture supernatants of recombinant thrombin-expressing cells (including the thrombin amino acid sequence NPs herein). Typically, NPs can be used in place of thrombin standards in immunoassays for thrombin if they possess at least one thrombin epitope recognized by the antibody used in the thrombin immunoassay in question, while the TBPs are used in place of antibodies for thrombin. The NPs also are useful, as appropriate, in functional assays for certain individual properties of thrombin, for example its procoagulant activity provided that the NP retains procoagulant activity.

Polypeptide TBPs typically are peptides or proteins which are capable of specifically binding FCP but are not capable of binding substantially to PCA, and vice-versa. They thus are highly specific inhibitors of either the procoagulant or aPC function of thrombin.

Peptide TBPs are obtained by the use of in vitro directed evolutionary methods such as those employing filamentous phage to present candidate sequences (otherwise known as phage display) and similar methods known per se which rely on the systematic generation and screening of peptides for activity. These typically are rather small molecules, containing on the order of about 5 to 20 residues. The FCP and PCA polypeptides of this invention are useful in screening for such peptide TBPs in the same general fashion as they are in screening for oligonucleotide TBPs.

Antibody TBPs are immunoglobulins, ordinarily monoclonal antibodies, which are capable of specifically inhibiting the procoagulant or aPC function of thrombin. Antibodies are raised against a protein composition comprising a reference sequence thrombin. In order to obtain an anticoagulant antibody the antibody pool is adsorbed onto an PCA, whereby antibodies that do not substantially bind (but which do demonstrate clotting inhibition) are recovered. These antibodies necessarily will be directed to fibrinogen cleavage epitopes. An analogous strategy is used to prepare a procoagulant antibody.

The term "monoclonal antibody" as used herein refers to an antibody obtained from a population of substantially homogeneous antibodies, i.e., the individual antibodies comprising the population are essentially identical in specificity and affinity. Monoclonal antibodies include hybrid and recombinant antibodies (e.g. "humanized" antibodies) regardless of species of origin or immunoglobulin class or subclass designation, as well as antibody fragments (e.g., Fab, F(ab')$_2$, and Fv). Thus, "monoclonal" antibodies are produced by any particular method that will yield a substantially homogeneous population. For example, monoclonal antibodies may be made using the methods described by Kohler & Milstein, "Nature" 256:495 (1975), Goding, *Monoclonal Antibodies: Principles and Practice* pp. 59–103 (1986), Kozbor, "J. Immunol." 133:3001 (1984), or Brodeur, et. al., *Monoclonal Antibody Production Techniques and Applications*, pp. 51–63 (1987), or may be made by recombinant DNA methods. Cabilly, et al., U.S. Pat. No. 4,816,567.

In a preferred embodiment of the invention, the monoclonal antibody will have an affinity for reference sequence thrombin of at least about $10^9$ moles/liter, as determined, for example, by the Scatchard analysis of Munson & Pollard, "Anal. Biochem." 107:220 (1980). Also, the monoclonal antibody typically will inhibit the procoagulant or anticoagulant activity of thrombin at least about 50%, preferably greater than 80%, and most preferably greater than 90%, as determined, for example, by the PC activation assay or thrombin time determinations disclosed herein.

DNA encoding the monoclonal antibodies is readily isolated and sequenced using conventional procedures (e.g., by using oligonucleotide probes that are capable of binding specifically to genes encoding the heavy and light chains of murine antibodies). Hybridoma cells serve as a preferred source of such DNA. Once isolated, the DNA may be placed into expression vectors, which are then transfected into host cells such as simian COS cells, Chinese Hamster ovary (CHO) cells, or myeloma cells that do not otherwise produce immunoglobulin protein, to obtain the synthesis of monoclonal antibodies in the recombinant host cells.

The DNA optionally may be modified in order to change the character of the immunoglobulin produced by its expression. For example, humanized forms of murine antibodies are produced by substituting a complementarity determining region (CDR) of the murine antibody variable domain for the corresponding region of a human antibody. In some embodiments, selected framework region (FR) amino acid residues of the murine antibody also are substituted for the corresponding amino acid residues in the human antibody. Humanized forms of murine antibodies also may be produced by substituting the coding sequence for human heavy and light constant chain domains in place of the homologous murine sequences. Morrison, et al., "PNAS" 81:6851 (1984).

Evolutionary selection methods for oligonucleotides that bind to target proteins are well known (WO 92/14843; Ellington et al., "Nature" 355:850 (1992); Bock et al., "Nature" 355:564 (1992); Ellington et al., "Nature" 346:818 (1990); Tuerk et al., "Science" 249:505 (1990). These oligonucleotides, commonly known as aptamers, generally contain the usual A, T, G, C or U bases or derivatives thereof, and comprise sequences that bind to a predetermined site on a target protein. In this case, the FCP and the PCA are used in negative (absence of binding) and positive (binding) selection protocols to yield TBPs such as aptamers that are specific for the inhibition of either clotting or aPC activity. A selection method for TBPs that inhibit the procoagulant function of thrombin (but do not substantially interfere with its anticoagulant activity) comprises (a) preparing a pool of candidates (oligonucleotides, peptides, extracts, proteins, etc.), (b) contacting the candidates with thrombin having procoagulant activity (typically reference sequence thrombin) (c) isolating from the thrombin those candidates that are able to bind to thrombin, (d) contacting the candidates from step c) with an NP in which the thrombin procoagulant function has been mutated substantially out of the NP, i.e., a PCA, and (e) recovering those candidates that do not bind to PCA. This ensures that any candidate so selected is capable of binding to the amino acid site(s) that were varied in arriving at the PCA polypeptide, i.e., the residues instrumental in thrombin's procoagulant function. Alternatively, a candidate or a pool enriched in potential anticoagulant TBP is selected by (a) preparing a pool of candidate binding partners (as above), (b) contacting the candidates with thrombin having procoagulant activity (typically reference sequence thrombin), (c) isolating from the thrombin those candidates that are able to bind to thrombin, (d) contacting the candidates from step c) with a thrombin NP in which the PC activating function has been mutated substantially out of the NP, i.e., a FCP, and (e) recovering those candidates that bind to FCP. The resulting candidate pool thus has been specifically enriched in candidates, or a candidate has been selected, that does not bind to thrombin at the mutated residues in the PC activation site. This candidate pool is then selected for anticoagulant activity, e.g., by further selecting for TBPs that do not bind to PCA. In the end, this will enrich the pool or select for candidate TBPs that do not bind the PC activation site but which do bind to the procoagulant residues of thrombin. Steps c) and d) optionally are reversed in either alternative.

TBPs that inhibit the protein C activating function of thrombin are selected by a process analogous to the enrichment of TBPs having the ability to inhibit the procoagulant function as described above, e.g., TBPs are selected that bind to thrombin but which do not bind to FCP.

The binding steps are accomplished in most cases using immobilized NP, typically NP that has been absorbed through its glycosyl substituents or its N- or C-terminus to an insoluble carrier in accordance with known methods (e.g., concanavalin A agarose immobilization followed by elution with alpha-methyl mannoside; Bock et al., op cit).

When the candidates are replicable moieties, e.g., filamentous display phage or oligonucleotides, one may optionally interpose one or more steps of amplification of the selected or isolated candidate pool between steps c) and d). Ordinarily, the candidates are not amplified between these steps. In addition, it is desirable to repeat steps a)–e) and, in most instances, to interpose an amplification step between steps e) and a). Amplification (usually accomplished by PCR in the case of oligonucleotide candidates), is useful in enriching the pools capable of demonstrating the selected-for function.

FCP and PCA are particularly useful as intermediates in the preparation of TBPs.

For diagnostic applications, TBPs or the NPs of this invention optionally are labeled with a detectable moiety. The detectable moiety can be any substituent which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; a radioactive isotopic label, such as, $^{125}I$, $^{32}P$, $^{14}C$, or $^3H$, or an enzyme, such as alkaline phosphatase, beta-galactosidase or horseradish peroxidase.

Any method known in the art per se can be used to conjugate the TBP or NP to the detectable moiety. See the methods described supra and Hunter, et al., "Nature" 144: 945 (1962); David, et al., "Biochemistry" 13:1014 (1974); Pain, et al., "J. Immunol. Meth." 40:219 (1981); and Nygren, J. "Histochem. and Cytochem." 30:407 (1982). Oligonucleotide TBPs are labeled in the conventional fashion heretofore employed in the diagnostic probe art.

The labeled NPs are employed in the detection for example of proteins that bind to thrombin, e.g. antibodies. In addition, the unlabeled NPs are linked to anti-analyte antibodies (either covalently or by immunoadsorption) or to analyte-binding receptors and are themselves used as labels by virtue of their ability to cleave labeled peptides that are readily detected by fluorescent or calorimetric methods. Typical receptors to which the unlabeled NPs are linked include cell surface macromolecules, e.g., LFA-1, VLA-4, mac-1, I-CAM1, I-CAM2, I-CAM3 or V-CAM1. Typical antibodies to which the unlabeled NPs are linked include antibodies directed against proteins participating in the blood clotting cascade as well as endothelial cell antigens, tumor antigens or other cell surface macromolecules. Suitable methods for conjugating proteins or for labeling proteins are well known and are conveniently applied to conjugating or labeling NPs. For example, NP B-chain is fused at its N-terminus to the C-terminus of an immunoglobulin heavy chain or to the C-terminus of the extracellular domain of a cell surface receptor.

The TBPs or NPs of the present invention optionally are employed in known immunoassay techniques, such as competitive binding assays, direct and indirect sandwich assays, and immunoprecipitation assays. Zola, *Monoclonal Antibodies: A Manual of Techniques*, pp. 147–158 (1987).

Competitive binding assays rely on the ability of a labeled standard (which may be thrombin, or an immunologically reactive portion thereof such as a labeled NP of this invention) to compete with the test sample thrombin for binding with a limited amount of TBP. The amount of thrombin in the test sample is inversely proportional to the amount of standard that becomes bound to the TBP. To facilitate determining the amount of standard that becomes bound, the TBP generally is insolubilized before or after the competition, so that the standard and analyte that are bound to the TBP conveniently are separated from the standard and analyte which remain unbound.

Sandwich assays involve the use of two TBPs, each capable of binding to a different target portion, or epitope, of thrombin. In a sandwich assay, the test sample analyte is bound by a first TBP which is immobilized on a solid support, and thereafter a second TBP binds to the analyte, thus forming an insoluble three part complex. David & Greene, U.S. Pat. No. 4,376,110. The second antibody may itself be labeled with a detectable moiety (direct sandwich assays) or may be measured using an anti-TBP antibody that is labeled with a detectable moiety (indirect sandwich assay). For example, one type of sandwich assay is an ELISA assay, in which case the detectable moiety is an enzyme.

The TBPs and NPs of the invention also are useful for in vivo imaging, wherein a TBP or NP labeled with a detectable moiety is administered to a host, preferably into the bloodstream, and the presence and location of the labeled TBP or NP in the host is assayed.

The following exemplary material is offered by way of illustration only and is not intended to limit the invention in any manner. All patent and literature references cited herein are expressly incorporated by reference.

EXAMPLE 1

1.1 Construction of Expression Vectors for the Production of Recombinant Human Prothrombin The entire 1869 base pairs of sequence encoding human prothrombin plus 12 base pairs of 5' untranslated sequence and 97 bases of 3' untranslated sequence were isolated on a SmaI to XbaI fragment from a cDNA clone of human prothrombin, BS(KS)-hFII (obtained from Ross T. A. MacGillivray, Dept of Biochemistry, Univ of British Columbia, Vancouver, Canada). This fragment was cloned into the eukaryotic expression vector, pRc/CMV (Invitrogen Corp, San Diego, Calif.). pRc/CMV was digested with Hind III and the 3' recessed ends were made blunt by filling in with the Klenow fragment of *E. coli* DNA polymerase I. The vector was further digested with XbaI and ligated with the SmaI to XbaI fragment containing the prothrombin coding sequence. The resulting construct, pRc/CMV-hPT, contains the prothrombin coding sequence flanked by sequences required for high level transcription in mammalian cells: the promoter from the immediate early gene of human cytomegalovirus and transcription termination sequences and polyadenylation signals from the bovine growth hormone gene. This clone also contains the β-lactamase gene conferring ampicillin resistance and the ColE1 origin of replication for propagation and maintenance in *E. coli*. Also present is the origin of replication of filamentous bacteriophage, f1 for production of single-stranded DNA in *E. coli* infected with the defective helper phage, M13KO7 (Vieira and Messing, 1987). This vector can be used for expression of human prothrombin in transiently transfected mammalian cells, however the presence of the neomycin phosphotransferase gene means that permanently transfected cell-lines for large scale expression can be selected by resistance to the antibiotic, G418.

1.2 Mutagenesis Strategy to Identify Functional Residues on the Surface of Thrombin Our mutagenesis strategy was designed to systematically scan the surface of human α-thrombin to identify residues important for fibrinogen clotting, thrombomodulin-dependent protein C activation and inhibition of clotting by heparin/antithrombin III and the thrombin aptamer. The strategy was designed to maximize the chances of identifying functional residues while minimizing the opportunities for the non-specific disruption of protein conformation. The charged and polar (R, K, D, E, H, S, T, Q, N, Y, W) amino acids were of particular interest for mutation as these residues are capable of participating in hydrogen bonds and electrostatic interactions that are likely to be important for the binding of charged ligands. Secondly, only the charged and polar residues that are highly exposed to solvent on the surface of α-thrombin were selected for mutation. The solvent accessible surface residues were targeted as these residues are available for interactions with ligands and are more tolerant of sequence variation (Bowie et al., 1990). The fractional accessibility (Rose et al., 1985) to a solvent probe of radius 1.4 Å was determined for each residue in thrombin in the 2.3 Å crystal structure of human α-thrombin complexed with the inhibitor hirudin (Rydel et al., 1990) and the 70 charged and polar residues with a fractional accessibility of >35% were selected for mutation. Only a single residue, R36a, was excluded from this list. R36a is located at the junction between the A and B chains of α-thrombin and is required for the processing of prothrombin to mature, two chain, α-thrombin. However, several residues were added to the list, including five residues (R20, K65, H66, R68, K77) located in the presumed fibrinogen-binding exosite and two residues (R98, W249) in the putative heparin-binding site. Thus, a total of 76 residues were replaced with alanine by oligonucleotide-directed mutagenesis. Alanine was used for all substitutions because alanine is compatible with both α- and β-secondary structures (Klapper, 1977), tolerated in both buried and exposed locations in proteins (Klapper, 1977; Rose et al., 1985) and the nonpolarity and small size of its side chain ensures that substitution with alanine is less likely to disrupt protein conformation. Multiple substitutions were made simultaneously when two or three targeted residues were clustered together. If such multiple mutants displayed a functional phenotype then the individual residues were subsequently substituted individually. The complete list of alanine replacement mutants is included in Table 1. The numbering system for residues in human α-thrombin is that used previously (Wu et al., 1991), where the residues in the B-chain are numbered consecutively (1–259). The residues in the A-chain are also numbered consecutively (1a–36a) but are suffixed with lower case 'a' to indicate identity with the A-chain.

1.3 Construction of Alanine Substitutions in Human Prothrombin By Oligonucleotide-Directed Mutagenesis Alanine substitutions were introduced into the human prothrombin gene by oligonucleotide-directed mutagenesis on a single-stranded DNA template (Zoller and Smith, 1982). A uracil-containing single-stranded DNA template was generated in a dut-ung- strain of *E. Coli* (CJ236) (Kunkel et al., 1987) allowing selection against the non-mutant template strand in ung+ strains of *E. coli* following extension and ligation of the mutagenic oligonucleotide primer. Synthetic oligonucleotide primers encoding alanine substitutions flanked by regions of 12 nucleotides complementary to the prothrombin coding strand were synthesized on an Applied Biosystems Inc. solid phase synthesizer using phosphoamidite chemistry. Phosphorylated primers were hybridized with the pRc/CMV-hPT template, extended by T7 DNA polymerase and ligated to the newly synthesized strand by T4 DNA ligase. The heteroduplex DNA was used to transform dut$^+$ung$^+$ *E. coli* strain, XL1-Blue, to select against the uracil-containing parental strand. Single-stranded DNA from individual transformants was sequenced using dideoxy-chain-termination and Sequenase 2.0 (United States Biochemical) to confirm the identity of each mutation. 500 ml cultures of each pRc/CMV-hPT mutant in XL1-Blue were used to produce plasmid DNA for transfection of cultured COS-7 cells. Approximately 1 mg of closed circular plasmid DNA was isolated using the QIAGEN Maxi plasmid preparation kit. DNA encoding the other NPs described herein is made in the same fashion using an appropriate template.

EXAMPLE 2

2.1 Expression and Activation of Recombinant Prothrombins for Transient Expression Assays Recombinant prothrombin constructs (10–20 µg) containing the unmodified prothrombin cDNA (for wild-type thrombin), thrombin mutated at S205A (for a negative control), and the various mutants were separately introduced into $10^6$ COS-7 cells grown in a 35 mm well, by the DEAE-dextran method of transfection (Adams and Rose, 1985). Two days post-transfection, the cell monolayer was washed twice with PBS and 1 ml of serum free DME medium was added back to the monolayer and incubated at 37° C. for 24 h (occasionally it was advantageous to culture at temperatures below about 30° C., in particular 27° C., when expression is not detected or is poor at 37° C., i.e. Mt 11, 12, 13, 34, 35, 14.5 and 37c). The conditioned medium was then harvested, centrifuged to remove any cell debris and concentrated 20-fold by ultrafiltration with Centricon-30. 50 µl of this concentrated medium were activated with 1.5 µg of Echis carinatus venom at 37° C. for 45 min. 12.5 µl of concentrated conditioned medium before and after venom activation were analyzed by Western blotting using monoclonal antibody (labeled with alkaline phosphatase) directed against human thrombin. The protein level was estimated by comparing the intensity of the band with a serially diluted plasma thrombin standard. The expression level of the thrombins varies from 0.12 to 2.0 µg of thrombin per $10^6$ cells, as estimated by both Western analysis and amidolytic assay.

2.1a Quantitation of Recombinant Prothrombins in Conditioned Cell Culture Medium by Slot Blot Thrombin protein concentration was determined by quantitative Western blotting using a Schleicher and Schuell Minifold II vacuum slot-blot apparatus. Prothrombin in 20-fold concentrated conditioned medium and purified prothrombin standards (American Diagnostica) was activated as described above. Samples and standards were diluted with PBS and adjusted to the same concentration of conditioned medium from mock transfected cells. Duplicate 100 µl aliquots containing approximately 50 ng activated prothrombin and duplicate aliquots of purified, activated prothrombin standards (1–200 ng) were aspirated through a 0.45 µm nitrocellulose filter in the slot-blot apparatus. Each slot was washed twice with 200 µl aliquots of PBS. The filter was washed twice with PBS and blocked with 5% non-fat skim milk (Carnation) in PBS. The blot was incubated with 11 µg/ml rabbit polyclonal immunoglobulins against human prothrombin (Dako) in 5% non-fat skim milk in PBS. The blot was washed with PBS containing 0.05% Tween-20 and incubated with 1 µCi/ml $^{35}$S-labeled donkey F(ab')$_2$ directed against rabbit immunoglobulins (Amersham). The blot was washed with PBS containing 0.05% Tween-20 and the radioactivity at each position was determined by scanning using an Ambis 4000 radioanalytic imaging detector. The thrombin concentration in each sample was determined from the standard curve which was linear over the range 1–200 ng prothrombin.

2.2 Amidolytic Assay

The hydrolysis by thrombin of the chromogenic substrate S-2238 was performed as previously described (Wu et al., 1991). A standard curve was constructed with plasma thrombin where 1 µg of thrombin gives a rate of hydrolysis of 1220.5 mOD/min in 300 µl of 100 µM S-2238. 20 µl of a one third dilution of venom activated conditioned medium were used for the measurement of the rate of hydrolysis of 300 µl of 100 µM S-2238.

2.3 Fibrinogen Clotting

The amount of venom activated conditioned medium that gives 335 mOD/min (equivalent to 0.27 µg of plasma thrombin) in the amidolytic assay of Example 2.2 was used in fibrinogen clotting. The reaction mixture contained 20 µl conditioned medium and 180 µl selection buffer containing 20 mM Tris acetate pH 7.5, 140 mM NaCl, 5 mM KCl, 1 mM MgCl2, 1 mM $CaCl_2$. Reaction was initiated by addition of 50 µl of human fibrinogen at 2 mg/ml freshly diluted in selection buffer from a stock of 10 mg/ml made in calcium free PBS. Time in seconds from addition of fibrinogen to clot formation was measured with a fibrometer. A plasma thrombin standard clotting curve was used to convert the clotting times into mg/ml equivalent of plasma thrombin. Results are expressed as % of wild type activity.

2.4 Protein C Activation

Cell lysates were prepared from TMnc cell expressing recombinant human thrombomodulin at the level of 504±34 fmoles/$10^6$ cells (Tsiang et al., 1992) as previously described (Tsiang et al., 1990). About 8×$10^6$ cells were lysed in 800 µl, giving a thrombomodulin concentration of ~5 nM in the lysate. Control lysates were similarly prepared from the untransfected parent CV-1 cell line which does not express TM. Commercially available human plasma protein C contains for each pmole of protein C ~0.005–0.02 pmoles of contaminating prothrombin. To circumvent this problem, 444 pmoles of protein C were first treated with 10 µg of Echis carinatus venom for 30 min at 37° C. to convert the contaminating prothrombin into thrombin which was then inactivated by titration with the thrombin inhibitor PPACK (D-Phe-Pro-Arg-Chloromethyl Ketone). This venom-processed and PPACK-titrated protein C was then used in the protein C activation assay (Tsiang et al., 1990). The assay mixture contained an amount of venom-activated conditioned medium corresponding to a standard amount of S-2238 amidolytic activity (8.5 mOD/min), 20 µl of TMnc cell lysate and 887 nM protein C in a total volume of 50 µl. This mixture was incubated at 37° C. for 1 h and stopped by addition of antithrombin III and heparin. For thrombomodulin-independent protein C activation, TMnc lysate was omitted and 2 mM $CaCl_2$ was replaced with 5 mM $Na_2EDTA$ in the assay mixture. The activated protein C generated was assayed by hydrolysis of chromogenic substrate S-2366. The raw scores of Table 1a reflect correction in the same fashion as in Example 2.3. The protein C activation activity was expressed as % of wild type activity.

2.5 Heparin-Dependent Antithrombin III Inhibition of Clotting

An amount of venom activated medium equivalent to a rate of S-2238 hydrolysis of 370 mOD/min was used in each assay. The volume of the sample was adjusted to 15 µl with mock transfected 20-fold concentrated medium, mixed with 135 µl selection buffer and pre-warmed at 37° C. Clotting time was measured immediately after simultaneous addition of 50 µl of 2 mg/ml fibrinogen and 50 µl of 650 nM AT-III with or without 0.1 U/ml heparin, to the sample mixture. Sensitivity of AT-III inhibition of clotting to heparin was expressed in % residual clotting activity in the presence of heparin relative to no heparin control.

EXAMPLE 3

3.1 Stable Expression of Recombinant Thrombins

Linearized recombinant prothrombin constructs from Example 1 (10 µg) were introduced into BHK-21 cells using the calcium phosphate method of transfection (Graham and Van der Eb, 1973; Parker and Stark, 1979). Clones were selected in culture medium containing the antibiotic, G418 and the expression levels were determined by amidolytic activity and Western blotting.

3.2 Production of Conditioned Medium for Protein Purification

Each desired BHK-21 clone expressing recombinant prothrombin was seeded into 850 $cm^2$ roller bottles and grown in complete DMEM containing 10% FCS (5×$10^6$ cell per 200 mL per roller bottle). Two days later, after the cells reached confluency, microcarrier beads, Cytodex 2 (Pharmacia LKB, Piscataway, N.J.) were added to coat the cell monolayer. Three days later, after the beads were covered by cells growing on them, the cells were washed with PBS and serum free DMEM containing 5 µg/mL insulin, 5 µg/mL transferrin, 5 µg/mL fetuin and 10 µg/mL vitamin K was added back to the cells for prothrombin secretion. Conditioned medium was harvested once 3 days later and once more 6 days later.

In an alternative procedure, instead of using microcarrier beads to expand the growth surface area, each desired BHK-21 clone was seeded into 1700 $cm^2$ expanded surface roller bottles in the same culture medium as described above (5×$10^6$ cells per 200 mL per roller bottle). Four days later, after the cells reached confluency, the cells were washed twice with PBS (instead of 3 times) and the same serum free medium (150 mL) was added back to the cells for prothrombin expression. Conditioned medium was harvested 3 times, once 4 days (150 mL) later, a second time 8 days later (150 mL) and a third time 11 days later (100 mL). Conditioned medium was filtered through a Whatman N° 1 paper using a Buckner funnel to remove cell debris and, in the first method, detached beads.

3.3 Medium Concentration and Dialysis

Conditioned serum-free medium containing prothrombin was concentrated with a tangential flow filtration system (Pellicon$^R$, Millipore, Bedlford, Mass.). The low protein binding cellulose membrane of the tangential flow filter (type PLGC, 5 square feet, MWCO. 10 000) was preconditioned following the manufacturer's instruction. During concentration, a pressure of 20–25 psi was used on the feeding-side, and a pressure of 3–4 psi was used on the retentate-side. The permeate flow rate was 150–200 mL/min. When the medium (retentate) was concentrated to ~500–600 mL, it was dialyzed 7–8 times against 1000–1200 mL of dialysis buffer (0.1 M potassium phosphate, pH 7.5) through the same filter. Briefly, the dialysis buffer was added to the medium concentrate with gentle mixing by circulating the mixture in the filtration system for about 2–3 min (permeation off. The mixture was then concentrated to 500–600 mL. After repeating the above dialysis 7–8 times, greater then 99.9% of the medium was replaced by the dialysis buffer.

3.4 Prothrombin Purification

The final dialysate (600–800 mL) was then filtered through a 0.45 μm sterile disposable filter (Nalgene, Rochester, N.Y.) and loaded onto a (2.6×7)cm DEAE-sepharose fast flow anion-exchange column (Pharmacia, Piscataway, N.J.). The prothrombin peak was eluted between 0.35–0.45 M potassium phosphate using a 0.1–0.7 M gradient. Aliquots of fractions containing prothrombin were determined by both amidolytic assay after soluble Echis carinatus venom activation (Sigma, St. Louis, Mo.) and SDS-PAGE. The active fractions were pooled and dialyzed against 0.02 M HEPES, 0.1 M NaCl, pH 8.0 at 4° C. over night. After dialysis the pooled prothrombin fractions were concentrated to 10–15 ml through a PM30 membrane using a stirred cell (Amicon, Beverly, Mass.).

3.5 Purification of NPs

Prothrombin NP in the concentrate was processed to NP by Echis carinatus venom that was pre-adsorbed on Amberlite CG50 (ICN Biomedicals, Irvine, Calif.) and optionally immobilized to Affi-Gel 10 beads (Bio Rad, Richmond, Calif.). Venom activation of the prothrombin NP was done with gentle rotation for 50 min at 37° C. The venom-beads were removed by centrifugation followed by filtration through a 0.45 μm filter. The filtrate was immediately loaded onto a (2.6×7) cm Amberlite CG50 (200–400 mesh) cation-exchange column. NP was eluted at 0.4 M as a single peak using a 0.1–1.0 M NaCl gradient. NP fractions were pooled based on amidolytic activity and SDS-PAGE (stained gel and Western blot). Pooled NP fractions were then concentrated to 8–10 mL by using a stirred cell with a PM30 membrane, and dialyzed against 0.1M NaCl, 0.02 M HEPES, pH 8.0. The purified NP was characterized with respect to amidolytic activity plasma clotting time, protein C activation, and platelet aggregation. Its purity and specific activity was also determined. Finally the NP preparation was stored at −80° C. in aliquots of 0.5 mL in sterile polypropylene tube.

3.6 Anticoagulation In Vivo Using NP

The formulations tested are specified below.

| Formulation | Article | Description |
| --- | --- | --- |
| A | control | Sterile, isotonic saline, USP. |
| B | test | A sterile, isotonic aqueous solution of wild-type human thrombin (Hematologic Technologies human thrombin from human plasma, prothrombinase activated) containing approximately 0.25 mg/mL thrombin. |
| C | control | Recombinant reference sequence prothrombin activated with Echis venom in the same fashion as the test NP (FIG. 2A). |
| D | test | A sterile, isotonic aqueous solution of recombinant NP K52A containing approximately 0.25 mg/mL NP (FIG. 2B) |
| E | control | A sterile, isotonic solution of rabbit brain thromboplastin (containing tissue factor). |

The formulations were each administered by intravenous administration to N.Z. white rabbits via an in-dwelling cannula placed in a central vein at a rate of infusion of about 13 mL/hour (14.3 U/kg 4 min for wild-type and 11.7 U/kg/min for K52A). Because of the potential thrombotic nature of the test formulations, it was thought that infusion in a peripheral vein (e.g., the marginal ear vein) might cause local thrombosis and ischemia due to a high local concentration of the test article. By accessing the central circulation (e.g., the SVC via the jugular vein) this complication would be minimized due to the high intravascular flow rates and rapid distribution of an infused compound. This approach has been previously used in baboons using human thrombin (J. Clin. Invest., 92:2003–12, 1993).

Infusion of formulation E was via a marginal ear vein as this route of administration has been shown to be safe and effective.

Figure 2B:
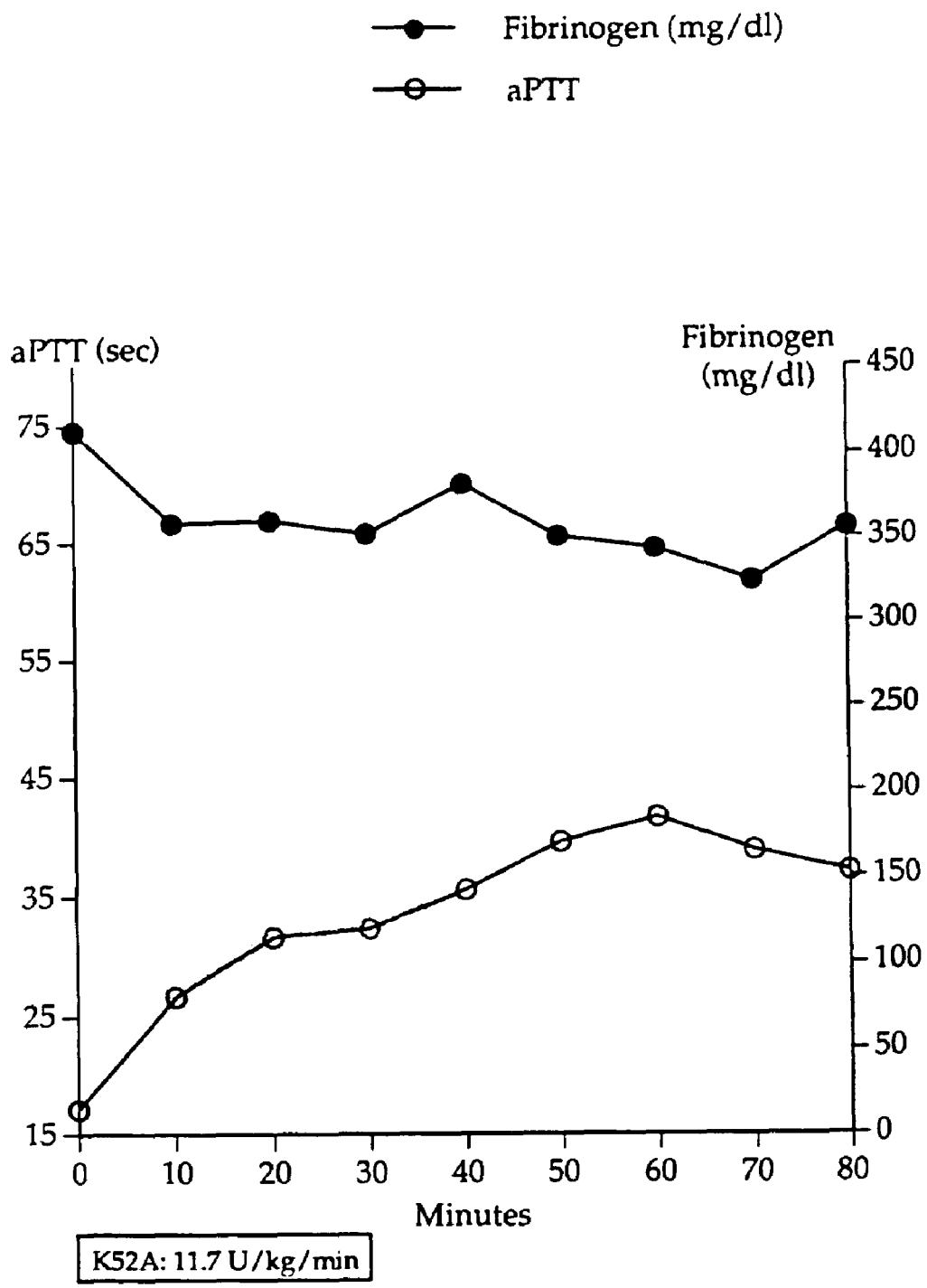
Figure 3:
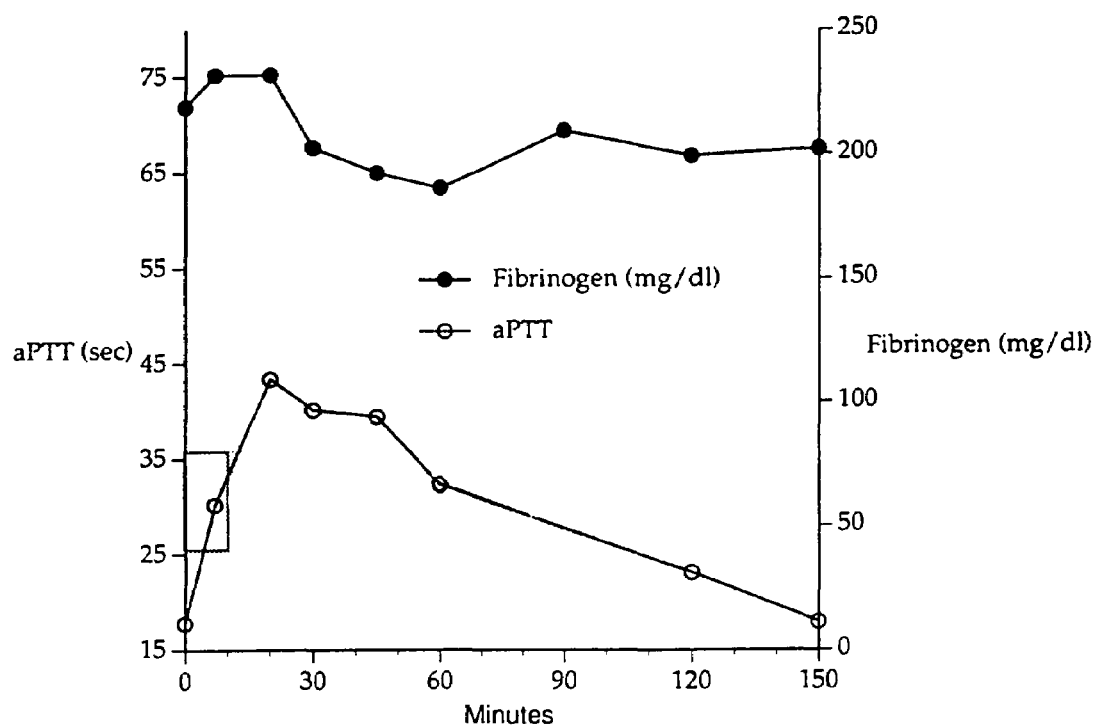
FIG. 3 shows that the K52A PCA has a significant half-life in vivo, conferring anticoagulant activity for up to about 150 minutes after administration.

The results are shown in FIGS. 2A, 2B and 3. Each figure represents the results with one rabbit. FIG. 2A shows that wild-type thrombin causes substantial fibrinogen consumption and excessive anticoagulation. In contrast, FIG. 2B demonstrates that K52A PCA is capable of anticoagulant activity in the normal range (the shaded area in the Figures), that it possesses clinically useful persistance of action, and that it does not cause fibrinogen consumption. FIG. 3 depicts elimination half-life and reversibility.

3.7 Protein C Activation by PCAs in Presence or Absence of TM

Figure 6:
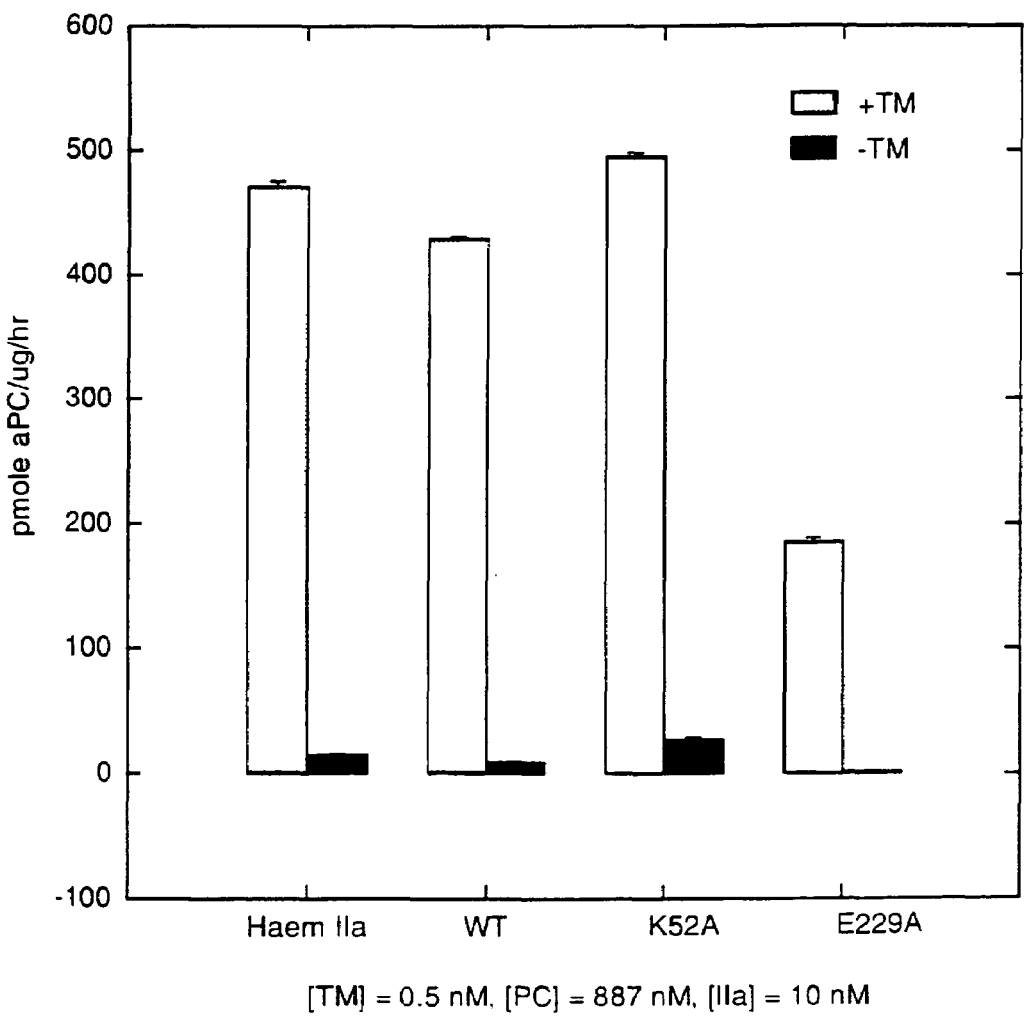
FIG. 6 demonstrates the continuing thrombomodulin dependence of two NPs of this invention, K52A and E229A.

The protein C activation assay is described in Example 2.4. Unlike Example 2.4, there is no need to pretreat the protein C stock with venom and PPACK because there is no venom in purified recombinant thrombin to activate the contaminant prothrombin in the protein C stock. Thrombin, thrombomodulin and protein C were used at concentrations indicated in FIG. 6. The reaction was incubated for 1 h at 37° C. and assayed for aPC activity using chromogenic substrate S-2366. This experiment demonstrates that the PCAs K52A and E229A remain thrombomodulin dependent.

EXAMPLE 4

Demonstration of Reversible Anticoagulation in Cynomolgus Monkeys Using Protein C Activator 2 (PCA 2) (E229A) and K52A PCA PCA 2 prepared as described in Example 3.4 and 3.5 was formulated in sterile isotonic aqueous solution in a total volume of 10 mL. The PCA 2 solution was intravenously infused continuously for 10 min into a peripheral vein of adult male cynomolgus monkeys at a rate of 60 mL/hr in a total volume of 10 mL. The infusion rate was controlled by use of an infusion pump. Two concentrations were administered: (1) 1.5 μg/kg/min (2 U/kg/min) and (2) 4.5 μg/kg/min (6 U/kg/min). (1 U is defined in text above).

Blood samples were collected by puncture of a peripheral vein at the following time points: immediately prior to the start of infusion t=0 and at intervals following the start of infusion t=5, 10, 20, 30, 45, 60, 90, 120, 150 min. Samples were approximately 2 mL in volume and collected into citrate. Plasma was obtained from whole blood within 10 minutes. Anticoagulation was monitored by measuring the aPTT in a fibrometer. Fibrinogen levels were determined from clotting assays using fibrinogen deficient plasma.

FIG. 4 illustrates the results of infusing individual monkeys with the two doses of PCA 2. Both doses resulted in prolongation of the clotting time beyond the anticipated therapeutic range (shaded region) without consumption of fibrinogen indicating that PCA 2 was devoid of detectable procoagulant activity in vivo. The effect was reversible, with the aPTT returning to normal approximately 170 minutes after the infusion was stopped. The reversibility of the effect suggested that coagulation factors were not consumed during the infusion, another indication that PCA 2 had no detectable procoagulant activity in vivo. Analysis of the kinetics of the reversal suggests a half-life for clearance of approximately 50 minutes. This degree of persistence is believed to be clinically useful.

Figure 5:
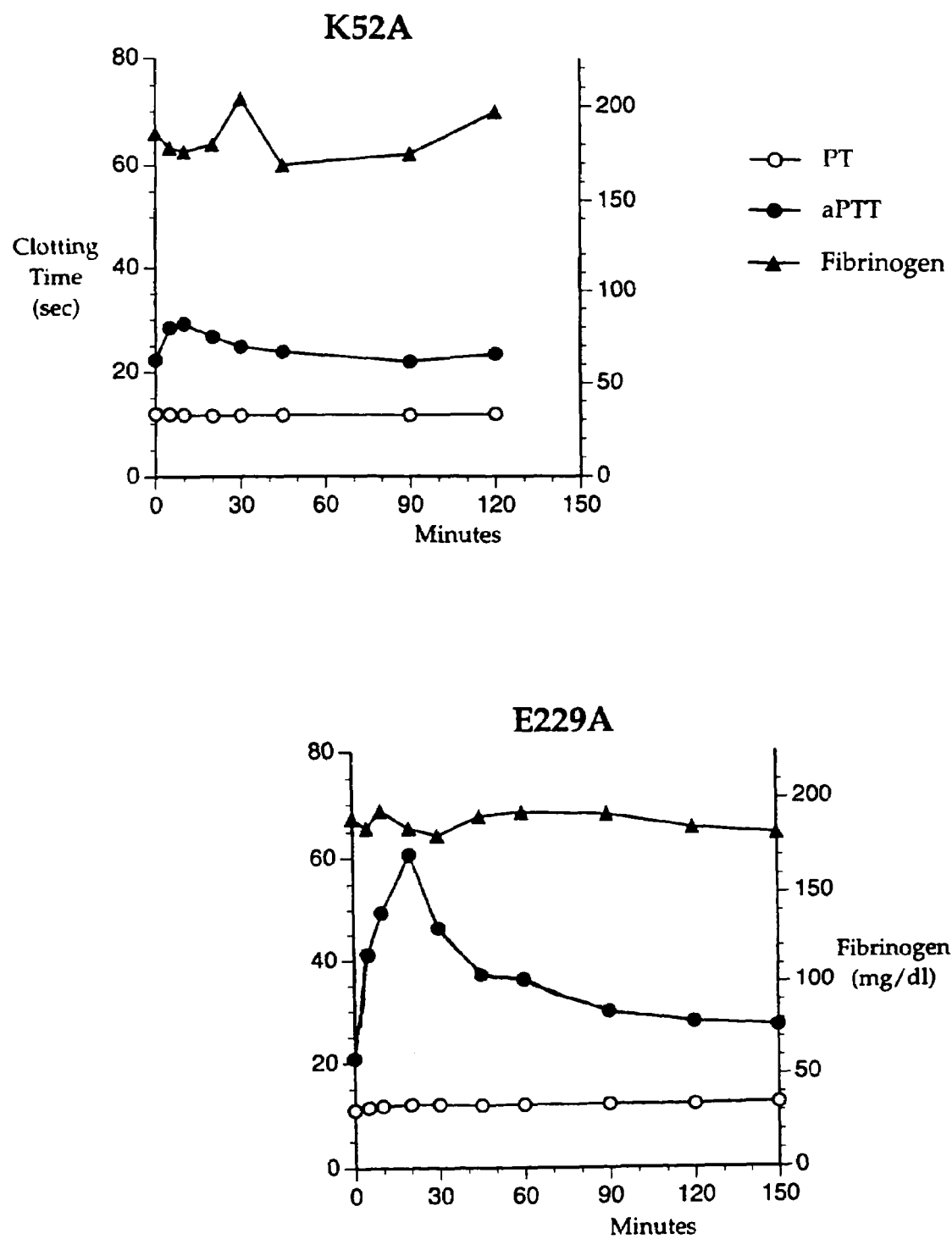
FIG. 5 compares the anticoagulant activities of two PCAs of this invention (K52 and E229A) in cynomolgus monkeys.

In a separate study, 2 U/kg/min of K52A PCA was prepared and infused over 10 minutes as described above and compared with a 2 U/kg/min E229A PCA in the above Example. The results are shown in FIG. 5. Although fibrinogen levels with K52A PCA at 2 U/kg/min were not changed, K52A PCA infused under substantially the same conditions, but at an overdose of 12 U/kg/min, resulted in an aPTT >10× control and a fall in fibrinogen to <10%. 12 U/kg/min was an overdose for monkeys despite the fact that it was well tolerated by rabbits at this dose (supra). Thus, doses in monkeys will generally be lower than in rabbits.

Platelet consumption and bleeding times were assayed and the results are shown in Table 2.

TABLE 2

|  | E229A (2 U/kg/min) | | | E229A (6 U/kg/min) | | | K52A (2 U/kg/min) | | |
|---|---|---|---|---|---|---|---|---|---|
| Time (post-infusion) (min) | 0 | 60 | 150 | 0 | 60 | 180 | 0 | | 120 |
| Platelets | 345 | | 352 | 400 | | 341 | 458 | | 471 |
| Bleeding Time (mm) | 2 | | 2 | | 2 | 2 | | | |

This data demonstrates that platelet function was preserved and bleeding times unchanged, in contrast to the results seen with gpIIb/IIIa inhibitors or thrombin inhibitors.

EXAMPLE 5

5.1 Expression and Use of B-chain NP Alone

In view of our observations that substitutions in the A chain of thrombin had negligible effect on S-2238 hydrolysis, FC or PA it will be useful to use the PCA B-chain alone as an anticoagulant or the FCP B-chain alone as a procoagulant. FCP or PCA B-chain is obtained from the two chain parent by reduction of the linking disulfide bond and refolding (Hageman et al, *Arch. Biochem. Biophys.* 171:327–336 [1975]). Preferably, however, the B-chain is obtained by expression of nucleic acid encoding the NP B-chain alone. An expression vector for B-chain PCA or FCP is derived from vectors constructed for the expression of prothrombin, prethrombin 1, prethrombin 2 (single chain α-thrombin) by deletion of the intervening sequence between the codon encoding the carboxyl terminus of the signal peptide and the amino terminal residue of the thrombin B chain (I1). Deletions are achieved by oligonucleotide-directed mutagenesis using chemically synthesized oligonucleotides that encode the deletion as primers on a single-stranded DNA template as described for construction of the ala substitution NPs. Optionally, the codon for C44 is mutagenized to encode A or S.

5.2 Expression of Prethrombin-1 and Prethrombin-2 as GST Fusion Proteins in *E. coli*

Prethrombin-1 (amino terminal residue S156, Degen et al. residue numbers) and prethrombin-2 (amino terminal residue T272, Degen et al. residue numbers) were expressed as soluble fusion proteins with glutathione S-transferase (GST) in the cytoplasmic compartment of *E. coli*. The expression vector used was pGEX-5X-1 (Pharmacia LKB Biotechnology) which contains the pBR322 origin of replication for propagation in *E. coli*, the β-lactamase gene encoding for resistance to the antibiotic ampicillin for maintaining the presence of the plasmid and the lac I9 gene encoding the lac repressor protein for dampening basal expression of the fusion protein. Expression is mediated by the tac promoter, which is inducible by IPTG, proximal to the ribosome binding site and translation start codon of the GST gene. The sequence encoding the 221 amino acids of GST is followed by a sequence (IEGR) encoding a proteolytic cleavage site for Factor Xa or Echis carinatus venom that can be used to cleave the GST moiety from the fusion protein, and a polylinker sequence containing unique restriction enzyme sites for the insertion of coding sequences to be fused to the GST coding sequence.

For Prethrombin-1, PCR primers were designed to amplify the nucleotide sequence encoding prethrombin-1 from S156 (Degen et al. residue numbers) to the carboxyl terminus of the thrombin B chain. The 5' end of the prethrombin-1 coding sequence was modified by the addition of a sequence encoding six consecutive histidine residues that can be used as an affinity tag for purification of fusion proteins on $Ni^{2+}$ chelation matrices and the addition of a sequence encoding an EcoRI restriction endonuclease site. The 3' primer was modified to insert a sequence encoding an XhoI restriction endonuclease site on the 3' side of the stop codon. For prethrombin-2, the same 3' PCR primer was used however the 5' PCR primer was designed to fuse the prethrombin-2 sequence starting at residue T272 (Degen et al. residue numbers) to the six histidine affinity tag and EcoRI restriction site. PCR primers were used to amplify the modified sequences encoding prethrombin-1 and prethrombin-2 using the prothrombin cDNA clone, BS(KS)-hFII as a template. The amplified fragments were cloned into the EcoRI and XhoI sites in pGEX-5X-1 in frame with the GST coding sequence. The resulting constructs were used to transform *E. coli* strain JM 105 (ATCC 47016).

Stationary phase cultures of JM 105 containing GST-prethrombin-1 and GST-prethrombin-2 were grown overnight at 37° C. in 25 ml Luria-Bertani medium (LB) containing 200 μg/ml ampicillin with shaking at 250 rpm. 200 ml of medium was inoculated with 4 ml of stationary phase culture and incubated at 37° C. with shaking at 250 rpm until cells reached exponential phase growth (O.D. at 600 nm=0.6–1.2). The incubation temperature was lowered to 17° C. and after 1 hour, IPTG was added to a final concentration of 1 mM and the incubation was continued for 24 hours. Bacterial cells were harvested by centrifugation at 5000 g, washed with 50 mM Tris Cl, 150 mM NaCl, pH 7.5. Cels were suspended in 20 ml 50 mM Tris Cl, 150 mM NaCl, pH 7.5, disrupted by sonication for 3–4 minutes (50% duty cycle), Triton X-100 was added to a final concentration of 1% and the extract was mixed at 80 rpm for 60 minutes at 4° C. Insoluble material was removed by centrifugation at 10,000 g. GST-prethrombin-1 and GST-prethrombin-2 were expressed in the soluble fraction at a yield of approximately 5 mg/liter of culture as assessed by Western blotting using a monoclonal antibody (EST-1) directed against human α-thrombin. GST-prethrombin-1 and GST-prethrombin-2 fusion proteins were processed to mature α-thrombin by incubation with 30 μg/ml Echis carinatus venom in 50 mM Tris Cl, 150 mM NaCl, pH 7.5 at 37° C. for 30 minutes or longer. Processing of the fusion proteins to fragments of the same size as the A- and B-chains of human α-thrombin was visualized by Western blotting following SDS-PAGE under reducing conditions. Upon processing, amidolytic activity towards the thrombin-specific chromogenic peptidyl substrate (S-2238) was assessed by incubating 200 ng of processed GST-prethrombin-1 or GST-prethrombin-2 fusion proteins with 100 μM S-2238 in 50 mM Tris Cl, 150 mM NaCl, pH 7.5 at 37° C. for 10 minutes. Amidolytic activity was only detected in samples after processing with Echis carinatus venom.

GST-prethrombin-1 and GST-prethrombin-2 fusion proteins were purified by affinity chromatography on glutathione-sepharose 4B (Pharmacia). Bacterial extracts were applied to a 1 ml column of glutathione-sepharose 4B, the column was sealed and mixed for 40 minutes. The column was drained and washed with 50 mM Tris Cl, 150 mM NaCl, pH 7.5 plus 1% Triton X-100, washed with 50 mM Tris Cl, 150 mM NaCl, pH 7.5 and eluted with 1 ml aliquots of 50 mM Tris Cl, pH 8.0 containing 10 mM glutathione. GST-prethrombin-1 and GST-prethrombin-2 fusion proteins eluted by 10 mM glutathione were approximately 50% pure as assessed by SDS-PAGE stained with coomassie blue.

The NPs of this invention are produced in the same fashion as the prethrombin-1 or prethrombin-2 in this example, and are processed to mature, activated NP as described herein, except that the constructs are mutagenized to introduce the desired sequence change into the expression vector prior to expression in JM 105.

EXAMPLE 6

Platelet Aggregation by PCA 2 (E229A) and Wild-type Thrombin

Although PCA 2 was demonstrated to be defective in fibrinogen clotting, another important procoagulant function of thrombin is the stimulation of platelet aggregation as a result of cleavage of a transmembrane receptor on the platelet surface. In order to demonstrate that PCA 2 is also defective in this procoagulant function of thrombin, platelet aggregation studies were performed comparing different concentrations of PCA 2 and wild-type thrombin.

Figure 7:
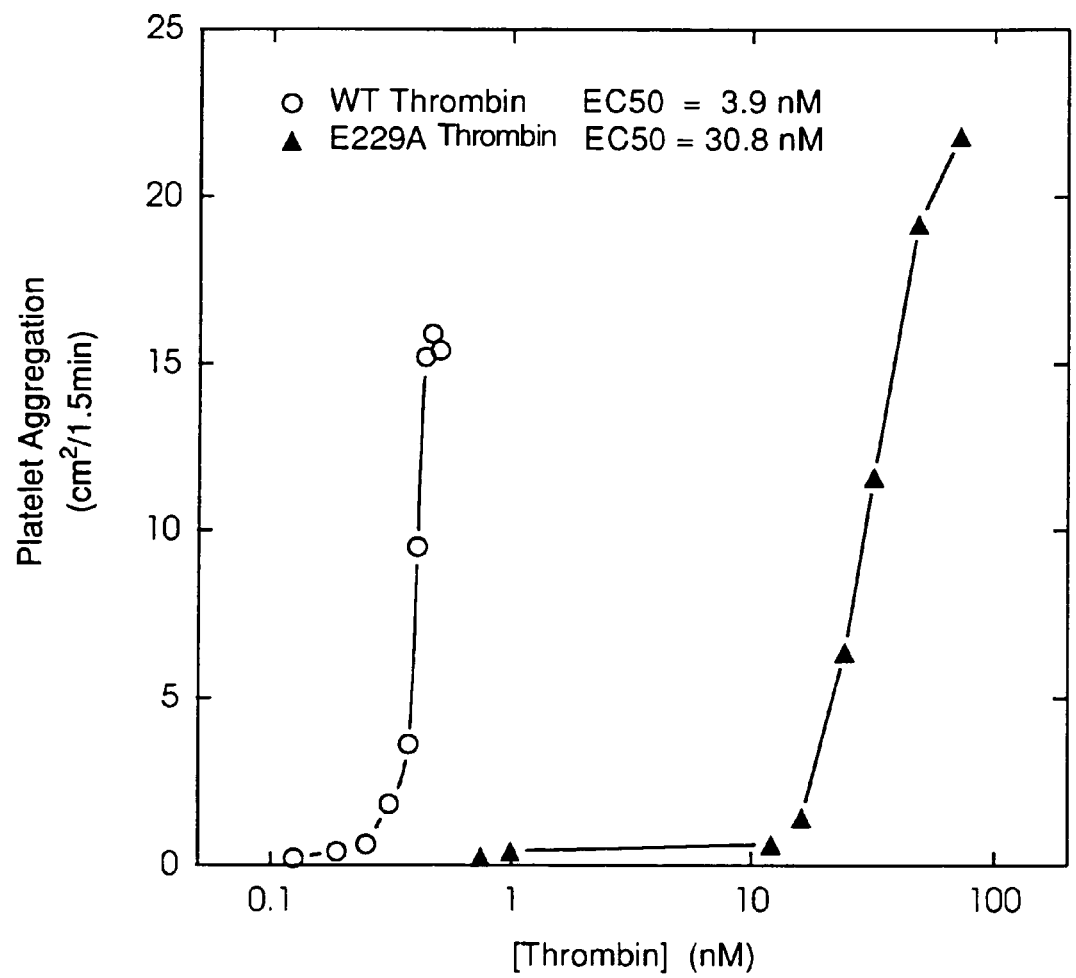
FIG. 7 illustrates the substantially reduced potency for platelet activation of two of the NPs of this invention as compared to wild-type thrombin.

Platelet aggregation studies comparing wild-type and PCA-2 thrombin were performed with citrated human platelet-rich plasma (PRP) using a Chrono-Log dual channel aggregometer (model 560-VS, Chrono-Log Corp, Havertown Pa.). Fresh human whole blood (4.5 mL) was collected in sterile Vacutainer tubes (Becton Dickenson, Rutherford, N.J.) containing 0.5 mL of 129 mM sodium citrate. PRP was separated from the citrated blood by centrifugation. The aggregometer was set according to the manufacturer's instructions. Recombinant human α-thrombin was added to pre-warmed (37° C. for 2 min) PRP at final concentrations ranging from 0.12 nM–0.49 nM for wild type and 0.74 nM–71.89 nM for PCA 2. The platelet aggregation stimulated by the thrombin addition to PRP was monitored by the increase in light transmission recorded on a chart recorder for up to 5 minutes. The extent of platelet aggregation was quantitated by measuring the area under the tracing 1.5 min after the addition of thrombin. The extent of platelet aggregation ($cm^2$) was plotted against thrombin concentration (FIG. 7).

The EC50 (concentration required for half-maximal stimulation) for stimulation of platelet aggregation by wild type thrombin and PCA 2 was estimated from the plot. PCA 2 (EC50=30.8 nM) is 8-times less effective than wild-type thrombin (EC50=3.9 nM) in stimulating platelet aggregation and thus is defective in this procoagulant activity as well as in clotting fibrinogen.

BIBLIOGRAPHY

Adams, G. A. et al., Mol. Cell. Biol. 5, 1442–1448, 1985.
Bowie J. U. et al., Science. 247, 1306–1310, 1990.
Dreyfus, M., et al., N. Eng. J. Med. 325, 1565–1568, 1991.
Graham, F. L., and Vand der Eb, A., J. Virology. 52, 456–467, 1973.
Gruber, A., et al., Circulation. 82, 578–585, 1991.
Gruber, A., et al., Circulation. 84, 2454–2462, 1991a.
Hirsh, J., N. Eng. J. Med. 324, 1865–1875, 1991.
Hirsh, J., N. Eng. J. Med. 324, 1565–1574, 1991a.
Klapper, M. H., Biochem. Biophys. Res. Comm. 78, 1018–1024, 1977.
Kunkel T. A. et al., Meth. Enzymol. 154, 367–382, 1987.
LaVallie, E. R., et al., Biotechnology, 11, 187–193, 1993.
Maggi, A., et al., Haemostasis. 17, 329–335, 1987.
Parker, B. A. and Stark, G. R., J. Virol. 31, 360–369, 1979.
Pescador, R., et al., Thrombosis Res. 53, 197–201, 1989.
Rose G. D. et al., Science. 229, 834–838, 1985.
Rydel T. J. et al., Science. 249, 277–280, 1990.
Smith, D. B. et al., Gene, 67, 31–40, 1988.
Stader, J. A. et al., Meth. Enzymol. 185,166–187, 1990.
Studier, F. W. et al., Meth. Enzymol. 185, 60–89, 1990.
Tabor, S. and Richardson, C. C., Proc. Natl. Acad. Sci. USA. 84, 4767–4771, 1987.
Taylor et al., J. Clin. Invest. 79, 918–925, 1987.
Tsiang, M., et al., Biochemistry 29, 10602–10612, 1990.
Tsiang, M., Lentz, S. R., and Sadler, J. E. J. Biol. Chem. 267, 6164–6170, 1992.
Vieira, J. and Messing, J., Meth. Enzymol. 153, 3–11, 1987.
Wells, J. A. Biochemistry, 29, 8509–8517, 1990.
Wu, Q., et al., Proc. Natl. Acad. Sci. USA 88, 6775–6779, 1991.
Zoller, M. J. and Smith, M., Nucleic Acids Res. 10, 6487–6493, 1982.

What is claimed is:

1. Isolated nucleic acid encoding a novel polypeptide (NP) having the amino acid sequence of reference sequence thrombin of SEQ. ID. NO. 2, in which at least one amino acid residue has been substituted for at least for one of the following thrombin amino acid residues, or at least one of the following thrombin amino acid residues has been deleted, or an amino acid residue has been inserted immediately adjacent to at least one of the following thrombin amino acid residues: R56, S58, Q60, E61, D71, W86, D87, N89, F90, T91, N93, D94, K101, H102, Y107, N110, E118, K119, R129, E130, R134, D149, D158, R159, E160, S164, Q167, K181, N187, K190, S194, E205, K210, D211, S212, T213, D219, D229, K232, A236, N252, N253, W263, E265, R269, D276, G271, K272, Y273, F275, Q287, W285, D291, or Q292, provided, however, that the nucleic acid does not encode thrombin K190A, thrombin K210E, thrombin E61K, thrombin N187D K190E, thrombin desP84P85W86, thrombin in which at least one amino acid residue within the thrombin activation site has been substituted or deleted, or a residue inserted adjacent to such an amino acid residue, or thrombin in which loop F55-E61 is replaced by the equivalent loop from tissue plasminogen activator.

2. The nucleic acid of claim 1 wherein the encoded NP has a ratio of protein C activating activity to fibrinogen clotting activity that is less than about half of, or greater than about twice that of reference sequence thrombin.

3. The nucleic acid of claim 1 wherein the encoded NP is selected from a thrombin wherein one or more of residues W86, K101, H102, Y107, S212, T213, E265, R269, K232, D270, K272, Y273 or F275 have been substituted, deleted or another residue inserted adjacent thereto.

4. The nucleic acid of claim 3 wherein W86 of the encoded NP is deleted or another residue selected from the following group has been substituted therefor or inserted immediately adjacent thereto: G, A, V, I, L, S, T, D, N, E, Q, C, K, M, F, Y, P, R, and H.

5. The nucleic acid of claim 3 wherein K101 or K232 of the encoded NP is deleted or another residue selected from the following group has been substituted therefor or inserted immediately adjacent thereto: G, A, V, I, L, S, T, D, N, E, Q, C, M, F, Y, P, W, R, and H.

6. The nucleic acid of claim 3 wherein D270 of the encoded NP is deleted or another residue selected from the following group has been substituted therefor or inserted immediately adjacent thereto: G, A, V, I, L, S, T, N, E, Q, C, K, M, F, P, W, R, and H.

7. The nucleic acid of claim 3 wherein residues E265 and W86, or R269 and E265 of the encoded NP are substituted or deleted.

8. The nucleic acid of claim 3 wherein H102 of the encoded NP is deleted or another residue selected from the following group has been substituted therefor or inserted immediately adjacent thereto: G, A, V, I, L, S, T, D, N, E, Q, C, K, M, F, Y, P, W and R.

9. The nucleic acid of claim 3 wherein Y107 of the encoded NP is deleted or another residue selected from the following group has been substituted therefor or inserted immediately adjacent thereto: G, A, V, I, L, S, T, D, N, E, Q, C, K, M, F, P, W, R, and H.

10. The nucleic acid of claim 3 wherein Y273 of the encoded NP is deleted or another residue selected from the following group has been substituted therefor or inserted immediately adjacent thereto: G, A, V, I, L, S, T, D, E, Q, C, K, M, N, F, P, W, R, and H.

11. The nucleic acid of claim 3 wherein E265 of the encoded NP is deleted or another residue selected from the following group has been substituted therefor or inserted immediately adjacent thereto: G, A, V, I, L, S, T, D, N, Q, C, K, M, F, Y, P, W, R, and H.

12. The nucleic acid of claim 3 wherein the substitution, deletion or insertion of the encoded NP is made only in the A or B chain.

13. The nucleic acid of claim 3 wherein R269 of the encoded NP is deleted or another residue selected from the following group has been substituted therefor or inserted immediately adjacent thereto: G, A, V, I, L, S, T, D, N, E, Q, C, K, M, F, Y, P, W, and H.

14. The nucleic acid of claim 3 wherein the residue of the encoded NP is substituted and the substitution is with alanine.

15. The nucleic acid of claim 3 wherein 2 or 3 of the residues of the encoded NP are substituted.

16. The nucleic acid of claim 3 which the encoded NP comprises B chain free of A chain.

17. The nucleic acid of claim 3 which the encoded NP comprises A and B chain.

18. The nucleic acid of claim 2 which the encoded NP possesses greater than about 2 times the residual proteolytic activity of reference thrombin when measured by hydrolysis of S-2238 in the presence of heparin-dependent AT-III inhibition.

19. The nucleic acid of claim 3 wherein a heparin binding site residue of the encoded NP is substituted.

20. The nucleic acid of claim 3 of the encoded NP which is E265D NP, E265F NP, E265S NP, E265W NP, E265Y NP, R269N NP, R269D NP, R269F NP, W86C NP, W86E NP or W86K NP.

21. The nucleic acid of claim 2 wherein the thrombin of the encoded NP has been substituted at residues Q60 or R134, one or more of such residues have been deleted or another residue has been inserted immediately adjacent to one or more of such residues.

22. The nucleic acid of claim 3 wherein the residue of the encoded NP is E265 or R269.

23. The nucleic acid of claim 1 wherein a residue of the encoded NP selected from the following group has been substituted for E265: G, A, V, I, L, S, T, D, N, Q, C, K, M, F, Y, P, W, R and H.

24. The nucleic acid of claim 1 of the encoded NP comprising E265K, E265D, E265A, E265W or E265Y.

25. The nucleic acid of claim 24 of the encoded NP comprising E265K or E265W.

26. The nucleic acid of claim 1 wherein both residues of the encoded NP selected from one of the following 6 groups have been substituted by another amino acid: E265,R269; E265,D270; W86,E265; and D94,E265.

27. The nucleic acid of claim 1 wherein the residue of the encoded NP is S212, T213, A236, E265, R269, D270, K272, Y273 or F275.

28. The nucleic acid of claim 27 wherein the residue of the encoded NP is S212, T213, K272, Y273 or F275.

29. The nucleic acid of claim 1 wherein W86 of the encoded NP has been substituted by G, A, V, L, I, S, T, D, E, Q, C, M, F, P, N, K, R or H.

30. The nucleic acid of claim 1 which, aside from the substitution, insertion or deletion of at least one of the defined thrombin of SEQ. ID NO. 2 residues of the encoded NP, is an allelic variation.

31. The nucleic acid of claim 1 in which from 1 to 5 of the enumerated residues of the encoded NP have been substituted.

32. The nucleic acid of claim 1 wherein W86 of the encoded NP is deleted, an amino acid residue inserted adjacent thereto, or W86 is substituted with A, C, E, G, I, K, L, M, N, P, Q, R, S, T, V or Y.

33. The nucleic acid of claim 32 wherein W86 of the encoded NP is substituted with A, C, E, G, K, L, M, N, Q, R, S, T, V or Y.

34. The nucleic acid of claim 1 wherein the amino acid residue substituted into thrombin of the encoded NP is hydroxyproline, betahydroxyaspartic acid, gamma-carboxyglutamic acid, hydroxylysine or norleucine.

35. The nucleic acid of claim 1 wherein the encoded NP also comprises desE182T183W184.

36. The nucleic acid of claim 1 wherein W263 of the encoded NP is deleted, an amino acid residue inserted adjacent thereto, or W263 is substituted with A, C, E, G, I, K, L, M, N, P, Q, R, S, T, V or Y.

37. Isolated nucleic acid encoding a novel polypeptide (NP) having the amino acid sequence of reference sequence thrombin of SEQ. ID. NO. 2, the improvement comprising substituting or deleting a codon for at least one of the following thrombin amino acid residues, or inserting a codon for at least one amino acid residue immediately adjacent to a codon for at least one of the following thrombin amino acid residues: R56, S58 Q60, E61, D71, W86, D87, K88, N89, F90, T91, N93, D94, K101, H102, Y107, N110, E118, K119, R129, E130, R134, D149, D158, R159, E160, S164, Q167, K181, N187, K190, S194, E205, K210, D211, S212, T213, D219, D229, K232, A236, N252, N253, W263, E265, R269, D270, G271, K272, Y273, G274, F275, Q287, K284, W285, D291, or Q292, provided, however, that the NP is not thrombin K88E, thrombin K190A, thrombin K210E, thrombin E61K, thrombin N187D, K190E, thrombin desP84P85QW86, thrombin in which at least one amino acid residue within the thrombin activation site has been substituted or deleted, or a residue inserted adjacent to such an amino acid residue, or thrombin in which loop F55-E61 is replaced by the equivalent loop from tissue plasminogen activator.

38. Isolated nucleic acid encoding a novel polypeptide (NP) having the amino acid sequence of reference sequence thrombin of SEQ. ID. NO. 2, wherein an alanine, serine, threonine, glycine, proline or cysteine amino acid residue has been substituted for at least one of the following thrombin amino acid residues or at least one of the following thrombin amino acid residues has been deleted, or an amino acid residue has been inserted immediately adjacent to at least one of the following thrombin residues: R56, K57, S58, Q60, E61, D71, W86, D87, K88, N89, F90, T91, N93, D94, K101, H102, R104, T105, R106, Y107, R109, N110, K113, E118, K119, R129, E130, R134, D149, D158, R159, E160, S164, Q167, K181, N187, K190, S194, E205, K210, D211, S212, T213, D219, D229, K232, A236, E238, N252, N253, W263, E265, R269, D270, G271, K272, Y273, G274, F275, Q287, K284, W285, D291, or Q292, provided, however, that the NP is not thrombin K88E, thrombin K190A, thrombin K210E, thrombin E61K, thrombin N187D, K190E, thrombin desP84P85QW86, thrombin in which at least one amino acid residue within the thrombin activation site has been substituted or deleted, or a residue inserted adjacent to such an amino acid, or thrombin in which loop F55-E61 is replaced by the equivalent loop from tissue plasminogen activator.

39. The nucleic acid of claim 38 wherein an alanine, serine or threonine residue of the encoded NP has been substituted for one of the enumerated thrombin residues.

40. Isolated nucleic acid encoding a novel polypeptide (NP) having the amino acid sequence of reference sequence thrombin of SEQ. ID. NO. 2 in which K88 has been deleted, an amino acid residue has been inserted immediately adjacent to K88, or K88 has been substituted by V, L, I, M, F, Y, W, A, S, T, G, P, C, Q or N.

41. The nucleic acid of claim 40 wherein residue K88 of the encoded NP is substituted or deleted.

42. The nucleic acid of claim 40 wherein K88 of the encoded NP is substituted with V, L, I, M, F, Y, W, C, S or T.

43. Isolated nucleic acid encoding a novel polypeptide (NP) having the amino acid sequence of reference sequence thrombin of SEQ. ID. NO. 2, and (2) in which at least one amino acid residue has been substituted for at least for one of the following thrombin amino acid residues, or at least one of the following thrombin amino acid residues has been deleted, or an amino acid residue has been inserted immediately adjacent to at least one of the following thrombin amino acid residues: D61, D87, N89, F90, T91, N93, D94, K101, H102, Y107, N110, E118, K119, R129, E130, R134, D149, D158, R159, E160, S164, Q167, K181, S194, E205, D211, S212, T213, D219, D229, K232, A236, N252, N253, W263, E265, R269, D270, G271, K272, Y273, F275, Q287, W285, D291, or Q292.

44. In a nucleic acid selected from the group consisting of thrombin-encoding nucleic acids comprising at least reference sequence thrombin having the nucleic acid sequence of SEQ. ID. NO. 2, the improvement comprising substituting a codon for at least one of the following thrombin amino acid residues, deleting a codon for at least one of the following thrombin amino acid residues, or inserting a codon for another at least one amino acid residue immediately adjacent to a codon for at least one of the following thrombin amino acid residues: R56, S58, Q60, E61, D71, W86, D87, N89, F90, T91, N93, D94, K101, H102, Y107, N110, E118, K119, R129, E130, R134, D149, D158, R159, E160, S164, Q167, K181, N187, K190, S194, E205, K210, D211, S212, T213, D219, D229, K232, A236, N252, N253, W263, E265, R269, D276, G271, K272, Y273, F275, Q287, W285, D291, or Q292, provided, however, that the nucleic acid does not encode thrombin K190A, thrombin K210E, thrombin E61K, thrombin N187D K190E, thrombin desP84P85W86, thrombin in which at least one amino acid residue within the thrombin activation site has been substituted or deleted, or a residue inserted adjacent to such an amino acid residue, or thrombin in which loop F55-E61 is replaced by the equivalent loop from tissue plasminogen activator.

45. The nucleic acid of claim 44, which prior to substitution, insertion or deletion, has SEQ. ID. NO. 2.

46. The nucleic acid of claim 44 wherein the E265 codon of the encoded NP is deleted or a codon for another residue selected from the following group has been substituted therefor or inserted immediately adjacent thereto: G, A, V, I, L, S, T, D, N, Q, C, K, M, F, Y, P, W, R, and H.

47. The nucleic acid of claim 44 wherein the W263 codon of the encoded NP is deleted, a codon for an amino acid residue inserted adjacent thereto, or the W263 codon is substituted with a codon for A, C, E, G, I, K, L, M, N, P, Q, R, S, T, V or Y.

48. A replicable vector comprising the nucleic acid of claims 1, 37, 38, 40 or 44.

49. A recombinant cell comprising the nucleic acid of claims 1, 37, 38, 40 or 44.

50. A method comprising culturing the cell of claim 49 and recovering the NP from the cell culture.

51. The method of claim 50 wherein the NP is expressed in the cell culture as a soluble polypeptide.

52. The method of claim 50 wherein the NP is expressed in the cell culture as the B chain alone.

53. The method of claim 50 wherein the nucleic acid encodes A and B sequences each one of which is independently ligated to nucleic acid encoding a signal sequence and the nucleic acid is coexpressed in the same host cell.

* * * * *